United States Patent
Broekema et al.

(10) Patent No.: US 9,174,965 B2
(45) Date of Patent: Nov. 3, 2015

(54) PYRIMIDINYLPIPERIDINYLOXYPYRIDONE ANALOGUES AS GPR119 MODULATORS

(71) Applicant: BRISTOL-MYERS SQUIBB COMPANY, Princeton, NJ (US)

(72) Inventors: Matthias Broekema, New Hope, PA (US); Gang Wu, Princeton, NJ (US); Dean A. Wacker, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/400,758

(22) PCT Filed: May 13, 2013

(86) PCT No.: PCT/US2013/040692
§ 371 (c)(1),
(2) Date: Nov. 12, 2014

(87) PCT Pub. No.: WO2013/173198
PCT Pub. Date: Nov. 21, 2013

(65) Prior Publication Data
US 2015/0133479 A1     May 14, 2015

Related U.S. Application Data

(60) Provisional application No. 61/647,772, filed on May 16, 2012.

(51) Int. Cl.
| | | |
|---|---|---|
| *C07D 401/14* | (2006.01) | |
| *A61K 31/506* | (2006.01) | |
| *A61K 31/403* | (2006.01) | |

(52) U.S. Cl.
CPC ............ *C07D 401/14* (2013.01); *A61K 31/403* (2013.01); *A61K 31/506* (2013.01)

(58) Field of Classification Search
CPC ............................ C07D 401/14; A61K 31/506
USPC .......................................... 544/331; 514/275
See application file for complete search history.

(56) References Cited

U.S. PATENT DOCUMENTS

| | | | |
|---|---|---|---|
| 5,488,064 A | 1/1996 | Sher | |
| 5,491,134 A | 2/1996 | Sher et al. | |
| 5,541,204 A | 7/1996 | Sher et al. | |
| 5,612,359 A | 3/1997 | Murugesan | |
| 5,770,615 A | 6/1998 | Cheng et al. | |
| 5,776,983 A | 7/1998 | Washburn et al. | |
| 6,043,265 A | 3/2000 | Murugesan et al. | |
| 2005/0080111 A1 | 4/2005 | Bayne et al. | |
| 2005/0245515 A1 | 11/2005 | Dehmlow et al. | |
| 2011/0251221 A1 | 10/2011 | Wacker et al. | |

FOREIGN PATENT DOCUMENTS

| | | |
|---|---|---|
| EP | 1 338 651 A1 | 8/2003 |
| WO | WO 96/38144 | 12/1996 |
| WO | WO 97/12613 | 4/1997 |
| WO | WO 97/12615 | 4/1997 |
| WO | WO 99/26659 | 6/1999 |
| WO | WO 00/01389 | 1/2000 |
| WO | WO 2004/065380 | 8/2004 |
| WO | WO 2004/076413 | 9/2004 |
| WO | WO 2005/007647 | 1/2005 |
| WO | WO 2005/007658 | 1/2005 |
| WO | WO 2005/025504 | 3/2005 |
| WO | WO 2005/089786 | 9/2005 |
| WO | WO 2005/121121 | 12/2005 |
| WO | WO 2006/083491 | 8/2006 |

(Continued)

OTHER PUBLICATIONS

Layzer, Degenerative Diseases of the Nervous System, Cecil Textbook of Medicine, 20th Edition, vol. 2, pp. 2050-2057 (1996).*
Damasio, Alzheimer's Disease and Related Dementias, Cecil Textbook of Medicine, 20th Edition, vol. 2, pp. 1992-1996 (1996).*
Jones et al., GPR119 agonists for the treatment of type 2 diabetes, Expert Opin. Ther. Patents, 19(10), pp. 1339-1359 (2009).*
Ahrén, B., "Autonomic regulation of islet hormone secretion—Implications for health and disease", Diabetologia, vol. 43, pp. 393-410 (2000).

(Continued)

*Primary Examiner* — Deepak Rao
(74) *Attorney, Agent, or Firm* — Barry H. Jacobsen

(57) ABSTRACT

Novel compounds of structure Formula I: (I) or an enantiomer, a diastereomer, or a pharmaceutically acceptable salt thereof, wherein R1, R2 and R3 are defined herein, are provided which are GPR119 G protein-coupled receptor modulators. GPR119 G protein-coupled receptor modulators are useful in treating, preventing, or slowing the progression of diseases requiring GPR119 G protein-coupled receptor modulator therapy. Thus, the disclosure also concerns compositions comprising these novel compounds and methods of treating diseases or conditions related to the activity of the GPR119 G protein-coupled receptor by using any of these novel compounds or a composition comprising any of such novel compounds.

(I)

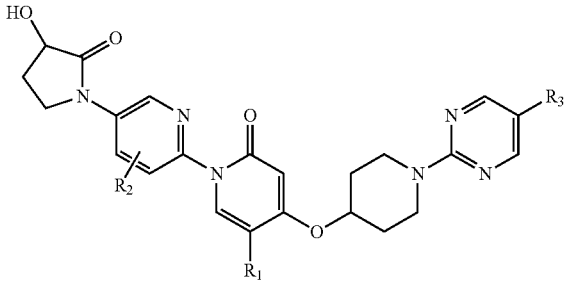

13 Claims, 11 Drawing Sheets

(56) References Cited

FOREIGN PATENT DOCUMENTS

| WO | WO 2008/137435 | 11/2008 |
|---|---|---|
| WO | WO 2008/137436 | 11/2008 |
| WO | WO 2009/012275 | 1/2009 |
| WO | WO 2009/012277 | 1/2009 |
| WO | WO 2010/009183 | 1/2010 |
| WO | WO 2011/127106 | 10/2011 |

OTHER PUBLICATIONS

Arbeeny, C. et al., "The Metabolic Syndrome: From Pathophysiology to Novel Treatment Strategies", Curr. Med. Chem.-Imm., Endoc. & Metab. Agents, vol. 1, No. 1, pp. 1-24 (2001).

Bernatowicz, M.S. et al., "1$H$-Pyrazole-1-carboxamidine Hydrochloride: An Attractive Reagent for Guanylation of Amines and Its Application to Peptide Synthesis", J. Org. Chem., vol. 57, No. 8, pp. 2497-2502 (1992).

Brancati, F.L. et al., "Body Weight Patterns from 20 to 49 Years of Age and Subsequent Risk for Diabetes Mellitus", Arch. Intern. Med., vol. 159, pp. 957-963 (1999).

Butler, A.E. et al., "β-Cell Deficit and Increased β-Cell Apoptosis in Humans with Type 2 Diabetes", Diabetes, vol. 52, pp. 102-110 (2003).

Chu, Z.-L. et al., "A Role for β-Cell-Expressed G Protein-Coupled Receptor 119 in Glycemic Control by Enhancing Glucose-Dependent Insulin Release", Endocrinology, vol. 148, No. 6, pp. 2601-2609 (2007).

Cornicelli, J.A. et al., "15-Lipoxygenase and Its Inhibition: A Novel Therapeutic Target for Vascular Disease", Current Pharmaceutical Design, vol. 5, No. 1, pp. 11-20 (1999).

Cosier, J. et al., "A Nitrogen-Gas Stream Cryostat for General X-ray Diffraction Studies", J. Appl. Cryst., vol. 19, pp. 105-107 (1986).

Dresser, G.K. et al., "Pharmacokinetic-Pharmacodynamic Consequences and Clinical Relevance of Cytochrome P450 3A4 Inhibition", Clin. Pharmacokinet., vol. 38, No. 1, pp. 41-57 (2000).

Ford, E.S. et al., "Prevalence of the Metabolic Syndrome Among US Adults", JAMA, vol. 287, No. 3, pp. 356-359 (2002).

Fredriksson, R. et al., "Seven evolutionarily conserved human rhodopsin G protein-coupled receptors lacking close relatives" FEBS Letters, vol. 554, pp. 381-388 (2003).

Hara, S., "Ileal Na$^+$/bile acid cotransporter inhibitors", Drugs of the Future, vol. 24, No. 4, pp. 425-430 (1999).

Hertzog, D.L., "Recent advances in the cannabinoids", Expert Opin. Ther. Patents, vol. 14, No. 10, pp. 1435-1452 (2004).

Hill, J.O. et al., "Environmental Contributions to the Obesity Epidemic", Science, vol. 280, pp. 1371-1374 (1998).

Le Stunff, C. et al., "Early Changes in Postprandial Insulin Secretion, Not in Insulin Sensitivity, Characterize Juvenile Obesity", Diabetes, vol. 43, pp. 696-702 (1994).

Mullin, J.W. et al., "Programmed cooling of batch crystallizers", Chemical Engineering Science, vol. 26, pp. 369-377 (1971).

Overton, H.A. et al., "Deorphanization of a G protein-coupled receptor for oleoylethanolamide and its use in the discovery of small-molecule hypophagic agents", Cell Metabolism, vol. 3, pp. 167-175 (2006).

Pedersen, O., "The Impact of Obesity on the Pathogenesis of Non-Insulin-Dependent Diabetes Mellitus: A Review of Current Hypotheses", Diabetes/Metabolism Reviews, vol. 5, No. 6, pp. 495-509 (1989).

Perry, I.J. et al., "Prospective study of risk factors for development of non-insulin dependent diabetes in middle aged British men", BMJ, vol. 310, pp. 560-564 (1995).

Prentki, M. et al., "Islet β cell failure in type 2 diabetes", J. Clin. Invest., vol. 116, No. 7, pp. 1802-1812 (2006).

Sendobry, S.M. et al., "Attenuation of diet-induced atherosclerosis in rabbits with a highly selective 15-lipoxygenase inhibitor lacking significant antioxidant properties", British Journal of Pharmacology, vol. 120, pp. 1199-1206 (1997).

Soga, T. et al., "Lysophosphatidylcholine enhances glucose-dependent insulin secretion via an orphan G-protein-coupled receptor", Biochemical and Biophysical Research Communications, vol. 326, pp. 744-751 (2005).

Yamanaka, H. et al., "Preparation of Novel β-Trifluoromethyl Vinamidinium Salt and Its Synthetic Application to Trifluoromethylated Heterocycles", Tetrahedron Letters, vol. 37, No. 11, pp. 1829-1832 (1996).

Yin, S. et al., "Simulated PXRD Patterns in Studies of the Phase Composition and Thermal Behavior of Bulk Crystalline Solids", American Pharmaceutical Review, vol. 6, No. 2, pp. 80-85 (2003).

Young, S.D. et al., "L-743,726 (DMP-266): a Novel, Highly Potent Nonnucleoside Inhibitor of the Human Immunodeficiency Virus Type 1 Reverse Transcriptase", Antimicrobial Agents and Chemotherapy, vol. 39, vol. 12, pp. 2602-2605 (1995).

\* cited by examiner

Experimental and simulated powder patterns of (R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one, free base, Form N-1.

Experimental and simulated powder patterns of (R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one, free base, Form N-2.

Experimental and simulated powder patterns of (R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one, free base, Form H2-3.

DSC of (R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one, free base, Form N-1

DSC of (R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one, free base, Form N-2

DSC of (R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one, free base, Form H2-3

TGA of (R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one, free base, Form N-1

TGA of (R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one, free base, Form N-2

TGA of (R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one, free base, Form H2-3 ssNMR of (R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one, free base, Form N-1

Spinning side bands are marked with an * ssNMR of (R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one, free base, Form H2-3

Spinning side bands are marked with an *.

PYRIMIDINYLPIPERIDINYLOXYPYRIDONE ANALOGUES AS GPR119 MODULATORS

CROSS REFERENCES TO RELATED APPLICATIONS

This application is a 371 of International Application No. PCT/US2013/040692 filed on May 13, 2013, which claims the benefit of U.S. Provisional Application Ser. No. 61/647,772, filed on May 16, 2012; each of which is fully incorporated by reference in its entirety.

FIELD OF THE INVENTION

The present invention provides novel pyridone compounds and analogues, which are modulators of the GPR119 G protein-coupled receptor, compositions containing them, and methods of using them, for example, for the prevention and/or treatment of diseases or disorders associated with the activity of the GPR119 G protein-coupled receptor, e.g., diabetes and obesity.

BACKGROUND OF THE INVENTION

Diabetes mellitus is a serious disease afflicting over 100 million people worldwide. In the United States, there are more than 12 million diabetics, with 600,000 new cases diagnosed each year. Diabetes mellitus is a diagnostic term for a group of disorders characterized by abnormal glucose homeostasis resulting in elevated blood sugar. There are many types of diabetes, but the two most common are Type 1 (also referred to as insulin-dependent diabetes mellitus or IDDM) and Type 2 (also referred to as non-insulin-dependent diabetes mellitus or NIDDM).

The etiology of the different types of diabetes is not the same; however, everyone with diabetes has two things in common: overproduction of glucose by the liver and little or no ability to move glucose out of the blood into the cells where it becomes the body's primary fuel.

People who do not have diabetes rely on insulin, a hormone made in the pancreas, to move glucose from the blood into the cells of the body. However, people who have diabetes either do not produce insulin or cannot efficiently use the insulin they produce; therefore, they cannot move glucose efficiently into their cells. Glucose accumulates in the blood creating a condition called hyperglycemia, and over time, can cause serious health problems.

Diabetes is a syndrome with interrelated metabolic, vascular, and neuropathic components. The metabolic syndrome, generally characterized by hyperglycemia, comprises alterations in carbohydrate, fat and protein metabolism caused by absent or markedly reduced insulin secretion and/or ineffective insulin action. The vascular syndrome consists of abnormalities in the blood vessels leading to cardiovascular, retinal and renal complications. Abnormalities in the peripheral and autonomic nervous systems are also part of the diabetic syndrome.

Diabetes has also been implicated in the development of kidney disease, eye diseases and nervous-system problems. Kidney disease, also called nephropathy, occurs when the kidney's "filter mechanism" is damaged and protein leaks into urine in excessive amounts and eventually the kidney fails. Diabetes is also a leading cause of damage to the retina at the back of the eye and increases risk of cataracts and glaucoma. Finally, diabetes is associated with nerve damage, especially in the legs and feet, which interferes with the ability to sense pain and contributes to serious infections. Taken together, diabetes complications are one of the nation's leading causes of death.

Many people with NIDDM have sedentary lifestyles and are obese; they weigh approximately 20% more than the recommended weight for their height and build. Furthermore, obesity is characterized by hyperinsulinemia and insulin resistance, a feature shared with NIDDM, hypertension and atherosclerosis.

Obesity, which is the result of an imbalance between caloric intake and energy expenditure, is highly correlated with insulin resistance and diabetes in experimental animals and human. However, the molecular mechanisms that are involved in obesity-diabetes syndromes are not clear. During early development of obesity, increased insulin secretion balances insulin resistance and protects patients from hyperglycemia (Le Stunff et al., *Diabetes*, 43:696-702 (1989)). However, over time, β-cell function deteriorates and non-insulin-dependent diabetes develops in about 20% of the obese population ((Pederson, P., *Diab. Metab. Rev.*, 5:505-509 (1989))) and (Brancati, F. L. et al., *Arch. Intern. Med.*, 159: 957-963 (1999)). Given its high prevalence in modern societies, obesity has thus become the leading risk factor for NIDDM (Hill, J. O. et al., *Science*, 280:1371-1374 (1998)). However, the factors which predispose a fraction of patients to alteration of insulin secretion in response to fat accumulation remain unknown. The most common diseases with obesity are cardiovascular disease (particularly hypertension), diabetes (obesity aggravates the development of diabetes), gall bladder disease (particularly cancer) and diseases of reproduction. Research has shown that even a modest reduction in body weight can correspond to a significant reduction in the risk of developing coronary heart disease.

Obesity considerably increases the risk of developing cardiovascular diseases as well. Coronary insufficiency, atheromatous disease, and cardiac insufficiency are at the forefront of the cardiovascular complication induced by obesity. It is estimated that if the entire population had an ideal weight, the risk of coronary insufficiency would decrease by 25% and the risk of cardiac insufficiency and of cerebral vascular accidents by 35%. The incidence of coronary diseases is doubled in subjects less than 50 years of age who are 30% overweight. The diabetes patient faces a 30% reduced lifespan. After age 45, people with diabetes are about three times more likely than people without diabetes to have significant heart disease and up to five times more likely to have a stroke. These findings emphasize the inter-relations between risks factors for NIDDM, obesity and coronary heart disease as well as the potential value of an integrated approach involving the treatment of both obesity and diabetes (Perry, I. J. et al., *BMJ*, 310:560-564 (1995)).

Type 2 diabetes results from the progressive loss of pancreatic β-cell function in the presence of insulin resistance, leading to an overall reduction in insulin output (Prentki, M. et al., "Islet failure in type 2 diabetes", *J. Clin. Invest.*, 116: 1802-1812 (2006)). β-cells are the cell type that store and release insulin in response to an elevation in plasma glucose or in response to hormonal signals from the gut following the ingestion of food. Evidence suggests that in type 2 diabetics the rate of β-cell cell death (apoptosis) exceeds that of new β-cell development, yielding an overall loss in β-cell number (Butler, A. E. et al., "β-cell deficit and increased β-cell apoptosis in humans with type 2 diabetes", *Diabetes*, 52:102-110 (2003)). β-cell apoptosis may arise from persistent elevations in plasma glucose levels (glucotoxicity) and/or plasma lipid levels (lipotoxicity).

G-protein coupled receptors (GPCRs) expressed on β-cells are known to modulate the release of insulin in response to changes in plasma glucose levels (Ahren, B., "Autonomic regulation of islet hormone secretion—Implications for health and disease", *Diabetologia*, 43:393-410 (2003)). Those GPCRs specifically coupled to the elevation of cAMP via the $G_s$ alpha subunit of G-protein, have been shown to enhance glucose-stimulated insulin release from β-cells. Cyclic AMP-stimulating GPCRs on β-cells include the GLP-1, GIP, β2-adrenergic receptors and GPR119. Increasing cAMP concentration in β-cells is known to lead to the activation of PKA which is thought to prevent the opening of potassium channels on the surface of the β-cell. The reduction in $K^-$ efflux depolarizes the β-cell leading to an influx of $Ca^{+-}$ which promotes the release of insulin.

GPR119 (e.g., human GPR119, GENBANK® Accession No. AAP72125 and alleles thereof; e.g., mouse GPR119, GENBANK® Accession No. AY288423 and alleles thereof) is a GPCR located at chromosome position Xp26.1 (Fredricksson, R. et al., "Seven evolutionarily conserved human rhodopsin G protein-coupled receptors lacking close relatives", *FEBS Lett.*, 554:381-388 (2003)). The receptor is coupled to Gs, and when stimulated, produces an elevation in cAMP in a variety of cell types including β-cell-derived insulinomas (Soga, T. et al., "Lysophosphatidylcholine enhances glucose-dependent insulin secretion via an orphan G-protein-coupled receptor", *Biochem. Biophys. Res. Comm.*, 326:744-751 (2005), PCT Publication Nos. WO 04/065380, WO 04/076413, WO 05/007647, WO 05/007658, WO 05/121121 and WO 06/083491, and EP 1338651). The receptor has been shown to be localized to the β-cells of the pancreas in a number of species as well as in specific cell types of the gastrointestinal tract. Activation of GPR119, with agonist ligands such as lysophosphatidylcholine, produce a glucose dependent increase in insulin secretion from primary mouse islets and various insulinoma cell lines such as NIT-1 and HIT-T15 (Soga, T. et al., "Lysophosphatidylcholine enhances glucose-dependent insulin secretion via an orphan G-protein-coupled receptor", *Biochem. Biophys. Res. Comm.*, 326:744-751 (2005); Chu, Z. L. et al., "A role for β-cell-expressed GPR119 in glycemic control by enhancing glucose-dependent insulin release", *Endocrinology*, doi: 10.1210/en.2006-1608 (2007)).

When activators of GPR119 are administered to either normal mice or mice that are prone to diabetes due to genetic mutation, prior to an oral glucose tolerance test, improvements in glucose tolerance are observed. A short-lived increase in plasma glucagon-like peptide-1 and plasma insulin levels are also observed in these treated animals (Chu, Z. L. et al., "A role for β-cell-expressed GPR119 in glycemic control by enhancing glucose-dependent insulin release", *Endocrinology*, doi:10.1210/en.2006-1608 (2007)). In addition to effects on plasma glucose levels, GPR119 activators have also been demonstrated to produce reductions in acute food intake and to reduce body weight in rats following chronic administration (Overton, H. A. et al., "Deorphanization of a G protein-coupled receptor for oleoylethanolamide and its use in the discovery of small-molecule hypophagic agents", *Cell Metabolism*, 3:167-175 (2006), and PCT Publication Nos. WO 05/007647 and WO 05/007658).

Accordingly, compounds that activate GPR119 could demonstrate a wide range of utilities in treating inflammatory, allergic, autoimmune, metabolic, cancer and/or cardiovascular diseases. PCT Publication Nos. WO 2008/137435 A1, WO 2008/137436 A1, WO 2009/012277 A1, WO 2009/012275 A1 (incorporated herein by reference and assigned to present applicant), WO 2010/009183 A1 and WO WO2011/127106 A1 (incorporated herein by reference and assigned to present applicant), disclose compounds that activate GPR119. The references also disclose various processes to prepare these compounds.

It is desirable to find new compounds with improved pharmacological characteristics compared with known GPR119 activators. For example, it is desirable to find new compounds with an improved amount of which the compound is accessible to the body (i.e. improved bioavailability). Additionally, it is desirable to find new compounds with improved GPR119 activity and selectivity for GPR119 versus other G protein-coupled receptors (i.e., 5HT2A receptor). Furthermore, it is also desirable to find compounds with advantageous and improved characteristics in one or more of the following categories:

(a) pharmaceutical properties (i.e., solubility, permeability, amenability to sustained release formulations);

(b) dosage requirements (e.g., lower dosages and/or once-daily dosing);

(c) factors which decrease blood concentration peak-to-trough characteristics (i.e., clearance and/or volume of distribution);

(d) factors that increase the concentration of active drug at the receptor (i.e., protein binding, volume of distribution);

(e) factors that decrease the liability for clinical drug-drug interactions (cytochrome P450 enzyme inhibition or induction, such as CYP 2D6 inhibition, see Dresser, G. K. et al., *Clin. Pharmacokinet.*, 38:41-57 (2000), which is hereby incorporated by reference); and (f) factors that decrease the potential for adverse side-effects (e.g., pharmacological selectivity beyond G protein-coupled receptors, potential chemical or metabolic reactivity, limited CNS penetration, ion-channel selectivity). It is especially desirable to find compounds having a desirable combination of the aforementioned pharmacological characteristics.

SUMMARY OF THE INVENTION

In accordance with the present invention, compounds are provided that have the general structure of Formula I:

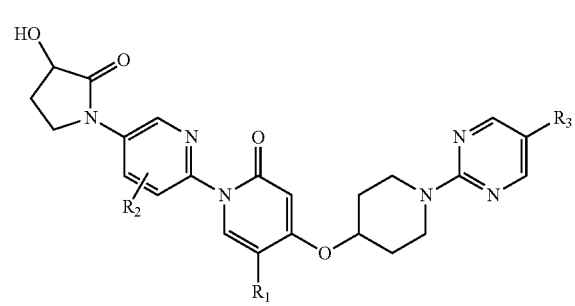

or an enantiomer, a diastereomer, or a pharmaceutically acceptable salt thereof, wherein $R^1$, $R^3$ and $R^4$ are defined below.

Compounds of the present invention modulate the activity of G protein-coupled receptors. Preferably, compounds of the present invention modulate the activity of the GPR119 G protein-coupled receptor ("GPR119"). Consequently, the compounds of the present invention may be used in the treatment of multiple diseases or disorders associated with GPR119, such as diabetes and related conditions, microvascular complications associated with diabetes, the macrovascular complications associated with diabetes, cardiovascular diseases, Metabolic Syndrome and its component conditions, obesity and other maladies. Examples of diseases or disorders associated with the modulation of the GPR119 G protein-coupled receptor that can be prevented, modulated, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dislipidemia, dyslipidemia, hyperlipidemia, hypertriglyceridemia, hypercholesterolemia, low HDL, high LDL, non-cardiac ischemia, vascular restenosis, pancreatitis, neurodegenerative disease, lipid disorders, cognitive impairment and dementia, bone disease, HIV protease associated lipodystrophy and glaucoma.

In addition, the present invention relates to a formulated product wherein the selected formulation is made by using a compound of Formula I as the only active ingredient or by combining (a) a compound of Formula I (using any of the compound embodiments listed herein) and (b) an additional active ingredient, for example, dipeptidyl peptidase-IV (DPP4) inhibitor (for example a member selected from saxagliptin, sitagliptin, vildagliptin, linagliptin, dutogliptin and alogliptin).

In addition, the present invention relates to a formulated product wherein the selected formulation is made by using a compound of Formula I as the only active ingredient or by combining (a) a compound of Formula I (using any of the compound embodiments listed herein) and (b) a dipeptidyl peptidase-IV (DPP4) inhibitor, wherein the DPP4 inhibitor is saxagliptin.

Therefore, in another embodiment of the present invention provides for compounds of Formula I, pharmaceutical compositions containing such compounds, and for methods of using such compounds. In particular, the present invention provides a pharmaceutical composition comprising a therapeutically effective amount of a compound of Formula I, alone or in combination with a pharmaceutically acceptable carrier.

Further, in another embodiment of the present invention provides a method for preventing, modulating, or treating the progression or onset of diseases or disorders associated with the activity of the GPR119 G protein-coupled receptor, such as defined above and hereinafter, wherein a therapeutically effective amount of a compound of Formula I is administered to a mammalian, i.e., human, patient in need of treatment.

The compounds of the invention can be used alone, in combination with other compounds of the present invention, or in combination with one or more other agent(s).

Further, the present invention provides a method for preventing, modulating, or treating the diseases as defined above and hereinafter, wherein a therapeutically effective amount of a combination of a compound of Formula I and another compound of Formula I and/or at least one other type of therapeutic agent, is administered to a mammalian, i.e., human, patient in need of treatment.

Additionally, the present invention describes compounds that have a beneficial, preferably a two-fold, more preferably, a three-fold, improvement in bioavailability in comparison to compounds previously disclosed in the art, such as those disclosed in PCT Publication No. WO 2011/127106 A1.

The present invention also describes compounds that have a beneficial improvement in solubility (aqueous, FaSSIF and/or both) in comparison to compounds previously disclosed in the art, such as those disclosed in PCT Publication No. WO 2011/127106 A1.

The present invention also describes compounds which are believed to have a decrease in the potential for adverse side-effects, for example, cardiac channel liability, in comparison to compounds previously disclosed in the art, such as those disclosed in PCT Publication No. WO 2011/127106 A1.

Additionally, the present invention describes compounds that have equivalent or a beneficial, preferably a two-fold, more preferably, a three-fold, improvement in GPR119 activity, in particular, in vivo glucose reduction, in comparison to compounds previously disclosed in the art, such as those disclosed in PCT Publication No. WO 2009/012275 A1.

The present invention also describes compounds that have equivalent or a beneficial improvement in metabolic stability, in particular, metabolic stability in human liver microsomes, in comparison to compounds previously disclosed in the art, such as those disclosed in PCT Publication No. WO 2009/012275 A1.

Compounds of the present invention also show unexpected advantages over compounds previously disclosed in the art, such as those disclosed in PCT Publication No. WO 2009/012275 A1 and/or WO 2011/127106 A1. The present compounds have been shown in an assay(s) to have a desirable combination of improvement in bioavailability and solubility. Such compounds should be more useful in the treatment, inhibition or amelioration of one or more diseases or disorders that are discussed herein.

Compounds of the present invention show additional unexpected advantages over compounds previously disclosed in the art, such as those disclosed in PCT Publication No. WO 2009/012275 A1 and/or WO 2011/127106 A1. The present compounds have been shown in an assay(s) to have a desirable combination of improvement in bioavailability, solubility and a decrease in the potential for adverse side-effects, for example, cardiac channel liability. As indicated above, such compounds should be more useful in the treatment, inhibition or amelioration of one or more diseases or disorders that are discussed herein.

Furthermore, compounds of the present invention show even more unexpected advantages over compounds previously disclosed in the art, such as those disclosed in PCT Publication No. WO 2009/012275 A1 and/or WO 2011/127106 A1. The present compounds have been shown in an assay(s) to have a desirable combination of improvement in bioavailability, solubility, a decrease in the potential for adverse side-effects, for example, cardiac channel liability and in vivo glucose reduction. Similar to above, such compounds should be more useful in the treatment, inhibition or amelioration of one or more diseases or disorders that are discussed herein.

Compounds of the present invention also show yet even more unexpected advantages over compounds previously disclosed in the art, such as those disclosed in PCT Publication No. WO 2009/012275 A1 and/or WO 2011/127106 A1. Similar to above, the present compounds have been shown in an assay(s) to have a desirable combination of improvement in bioavailability, solubility, a decrease in the potential for adverse side-effects, for example, cardiac channel liability, in vivo glucose reduction and metabolic stability in a human liver microsomal assay. Similar to above, such compounds should be more useful in the treatment, inhibition or amelioration of one or more diseases or disorders that are discussed herein.

piperidin-4-yl)oxy)-5'-(3-hydroxy-2-oxopyrrolidin-1-yl)-6'-methyl-2H-[1,2'-bipyridin]-2-one, free base, Form N-1.

Figure 2:
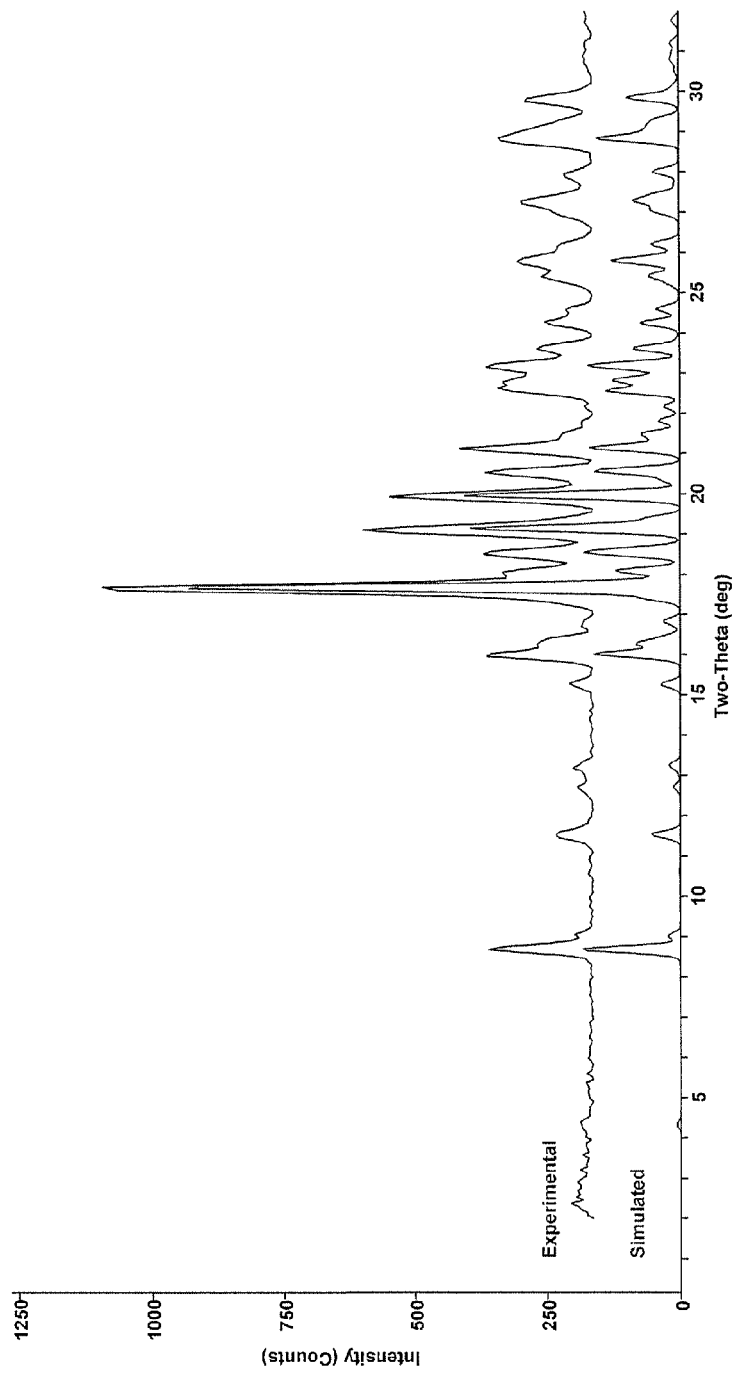

FIG. 2. Experimental and simulated powder X-ray diffraction patterns of (R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one, Form N-2.

Figure 3:
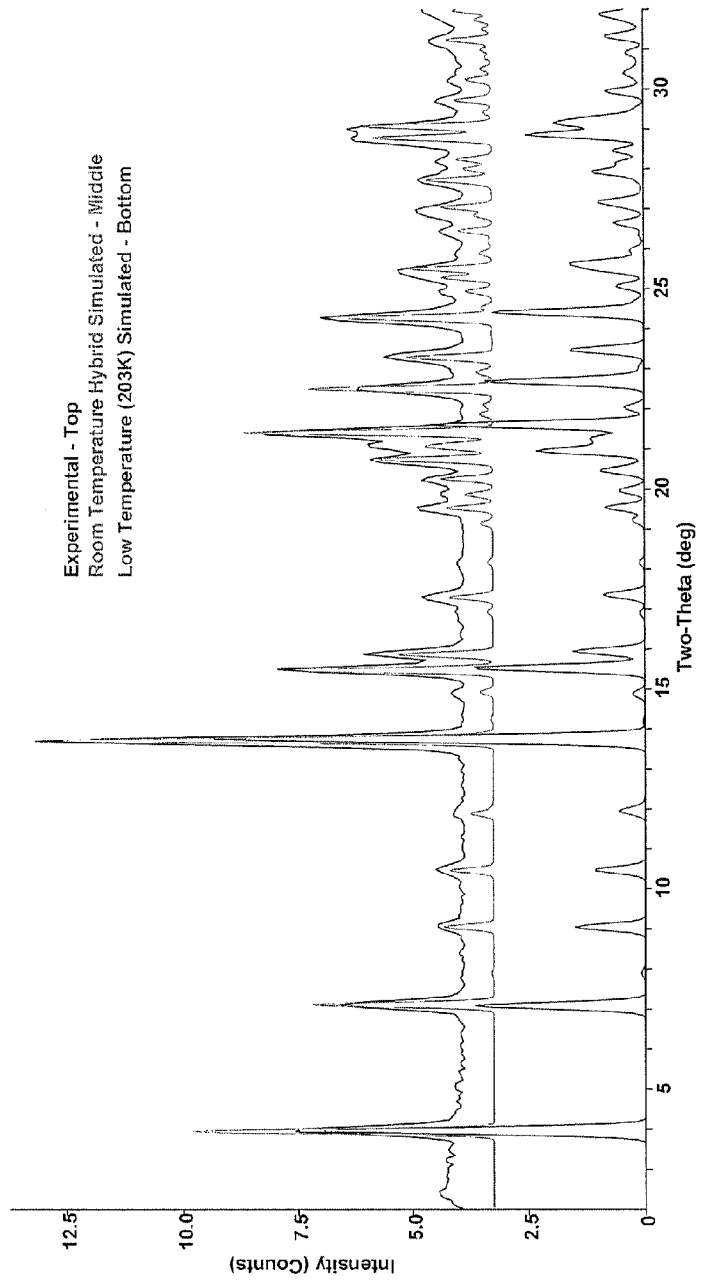

FIG. 3. Experimental and simulated powder X-ray diffraction patterns of (R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one, free base, Form H2-3.

Figure 4:
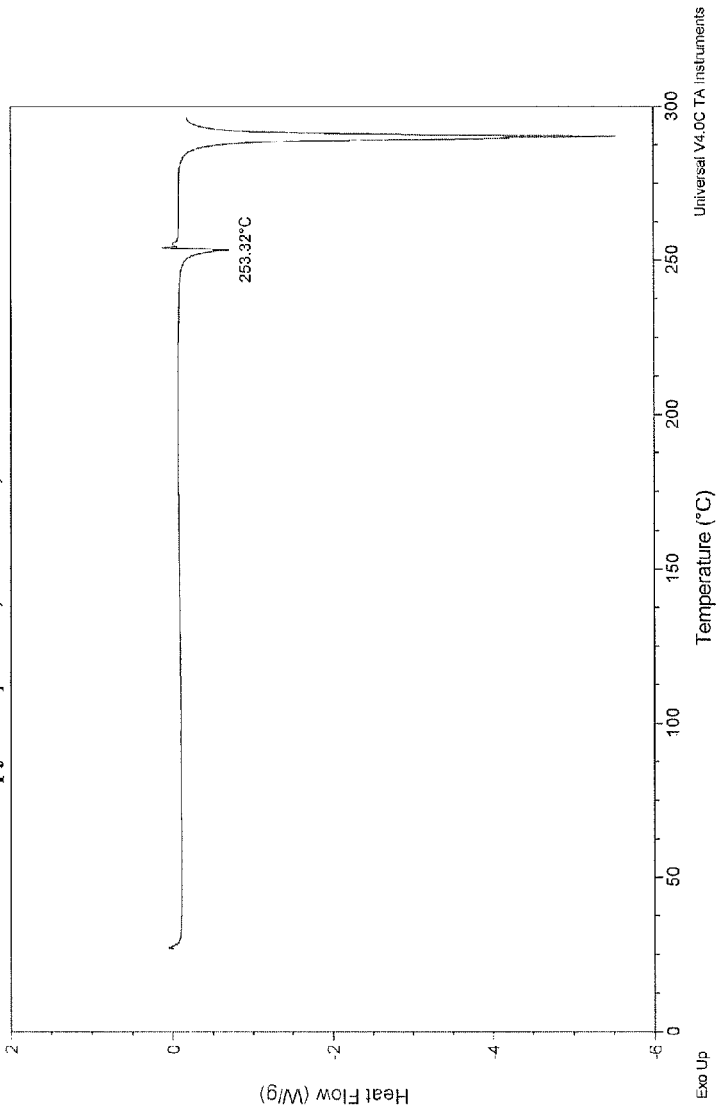

FIG. 4. Differential scanning calorimetry of (R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one, Form N-1.

Figure 5:
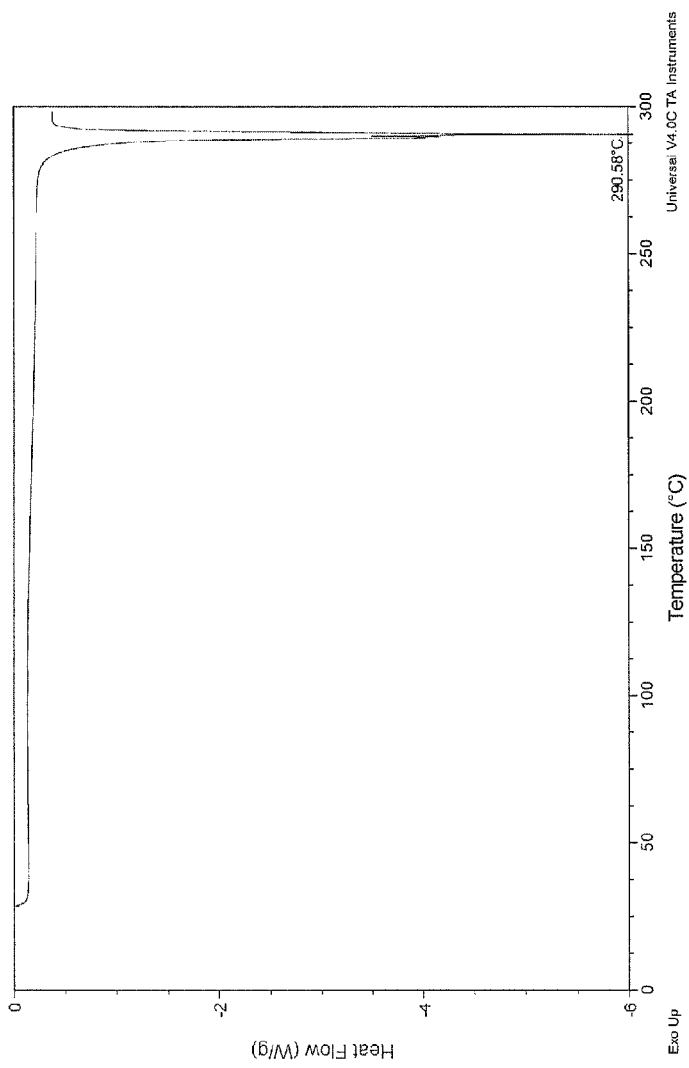

FIG. 5. Differential scanning calorimetry of (R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one, Form N-2.

Figure 6:
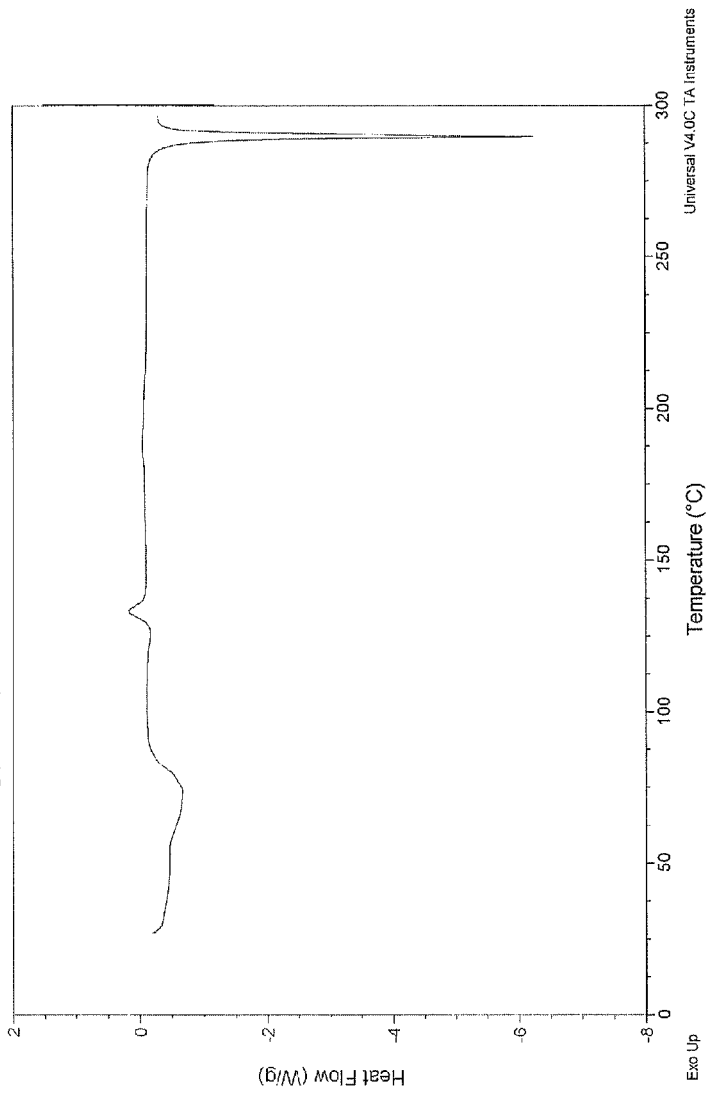

FIG. 6. Differential scanning calorimetry of (R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one, Form H2-3.

Figure 7:
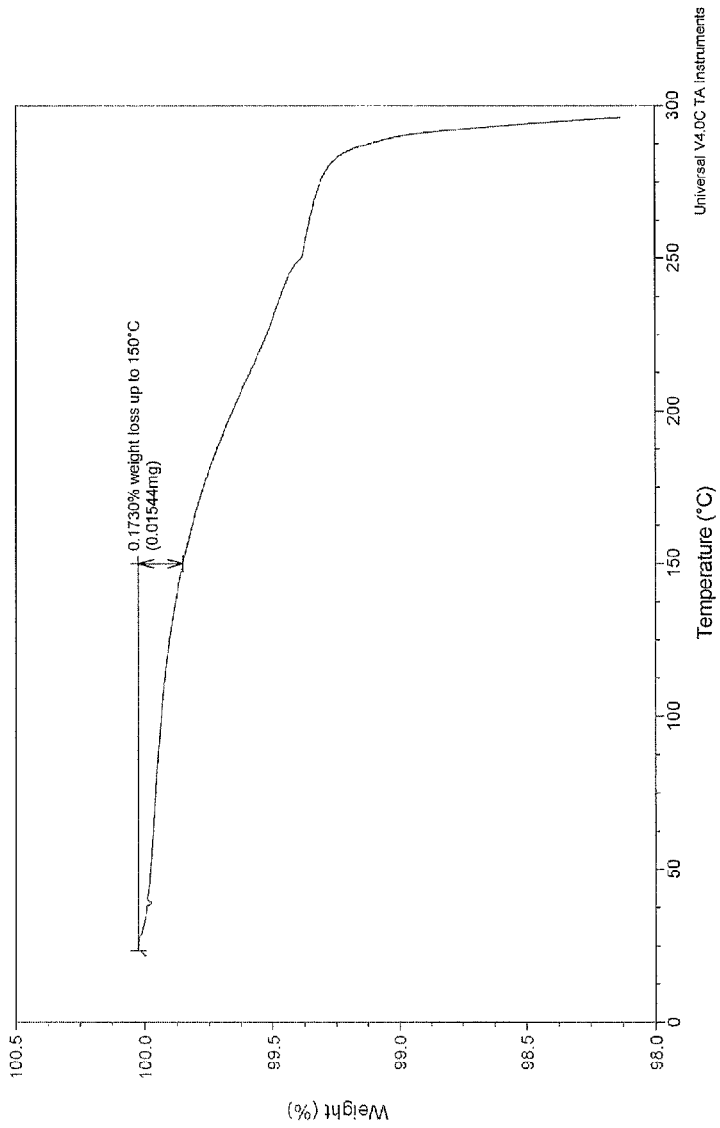

FIG. 7. Thermogravimetric analysis of (R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one, Form N-1.

Figure 8:
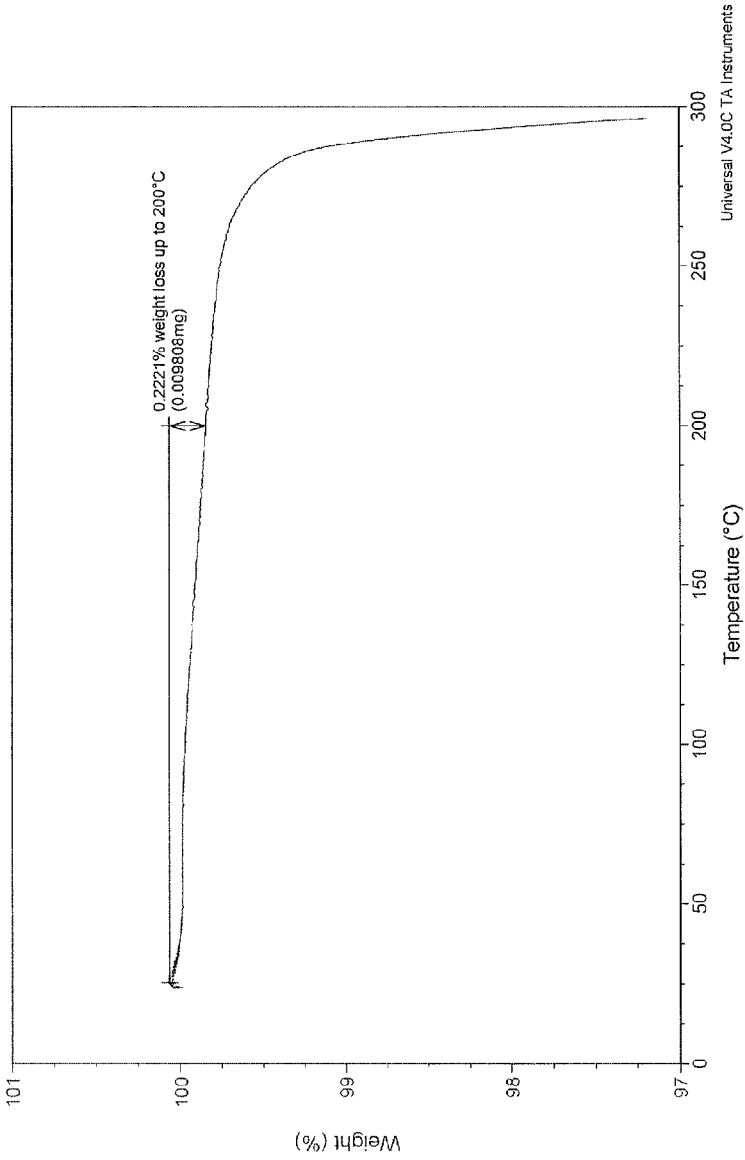

FIG. 8. Thermogravimetric analysis of (R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one, Form N-2.

Figure 9:
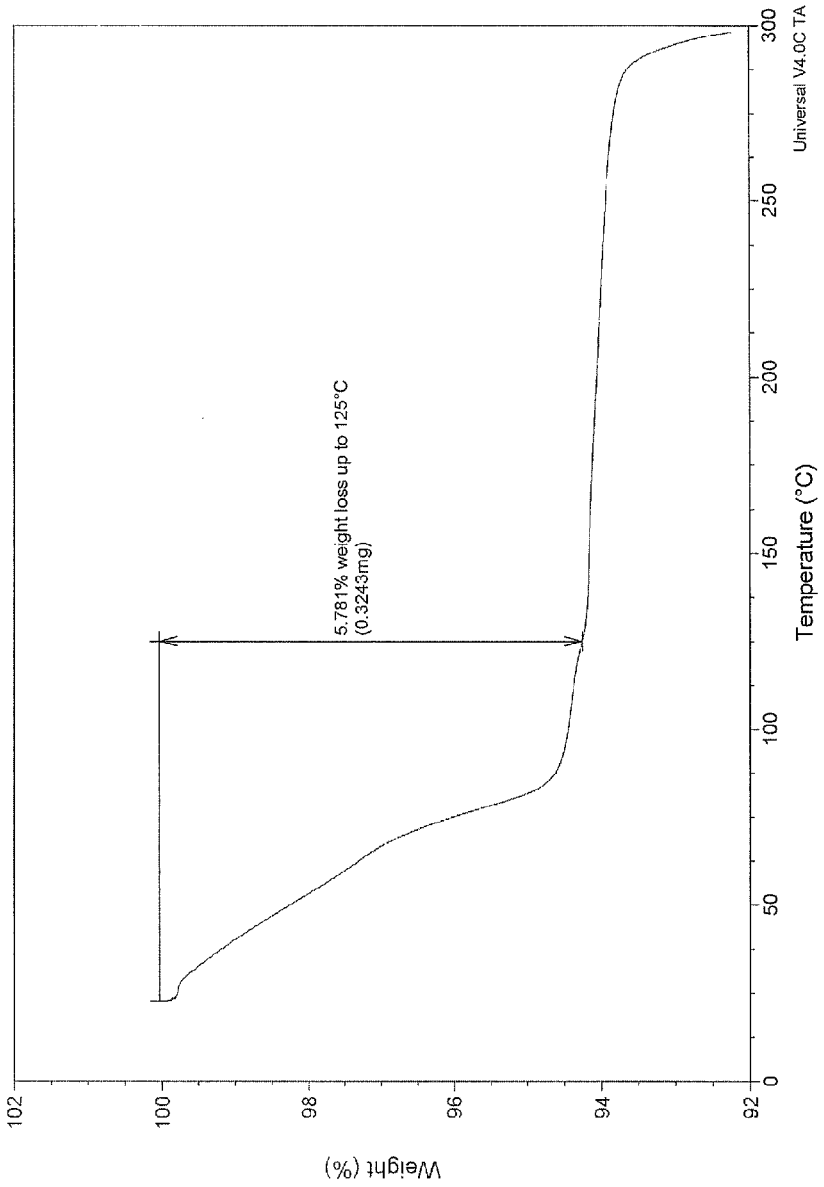

FIG. 9. Thermogravimetric analysis of (R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one, Form H2-3.

Figure 10:
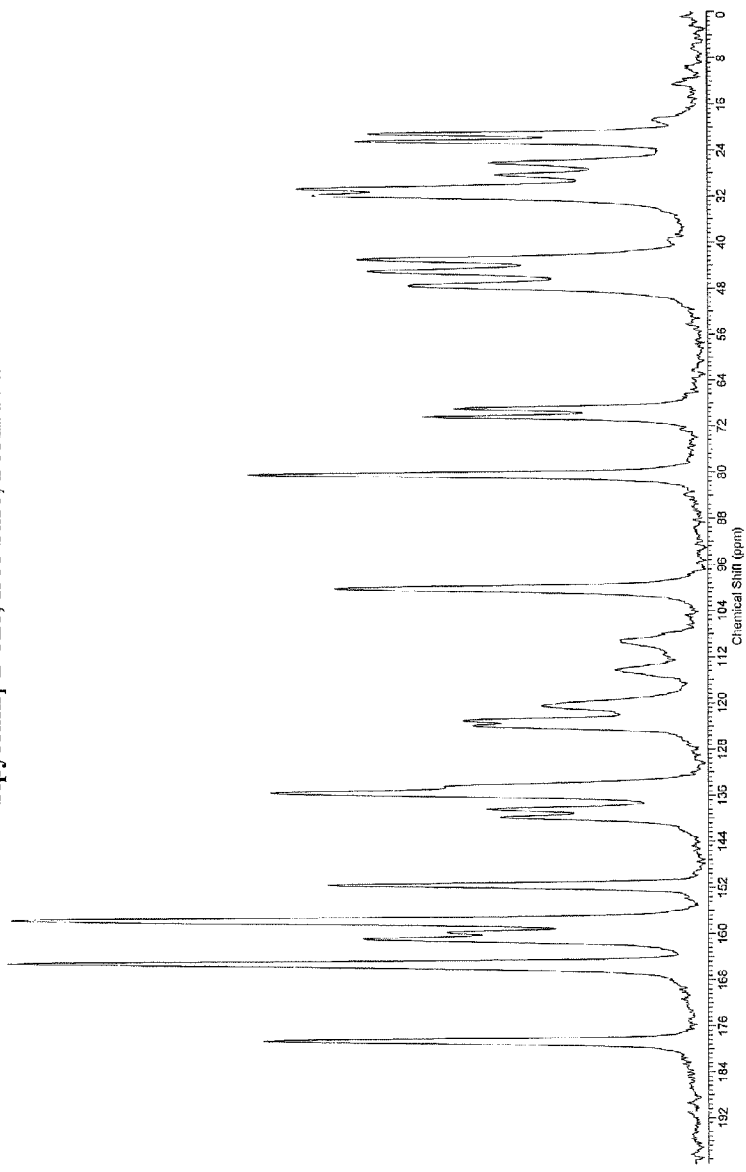

FIG. 10. Solid state nuclear magnetic resonance spectra (ssNMR) of (R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one, Form N-2.

Figure 11:
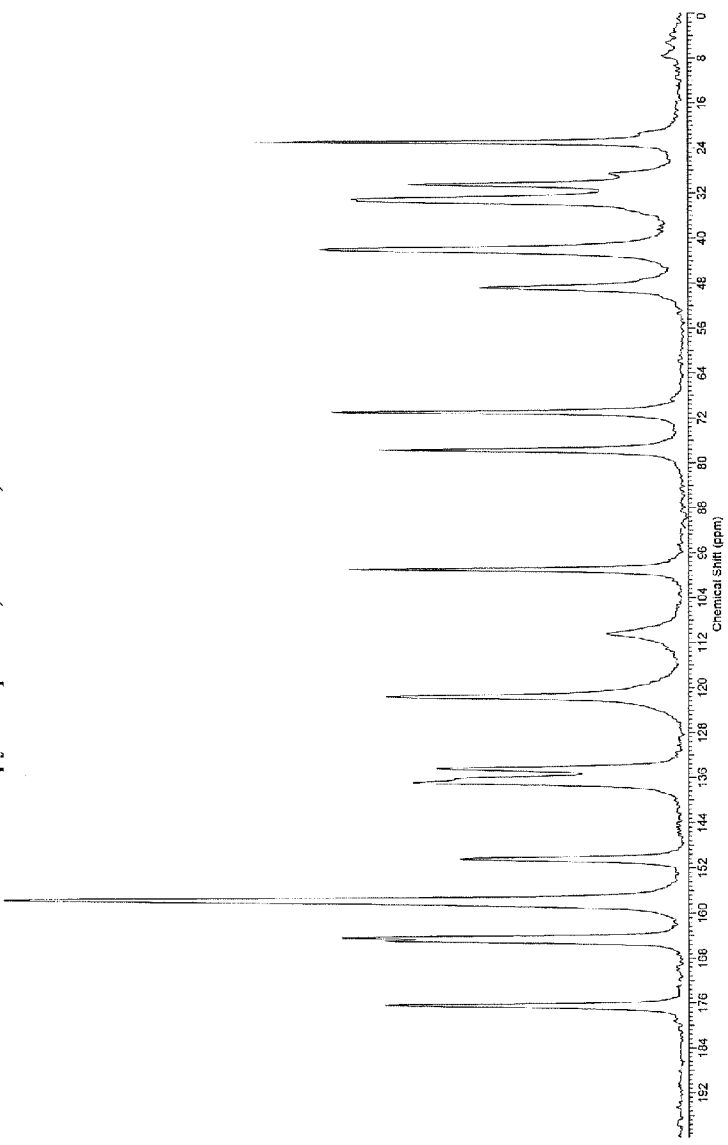

FIG. 11. ssNMR of (R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one, Form H2-3.

DETAILED DESCRIPTION

In one embodiment, the present invention provides a compound of Formula I:

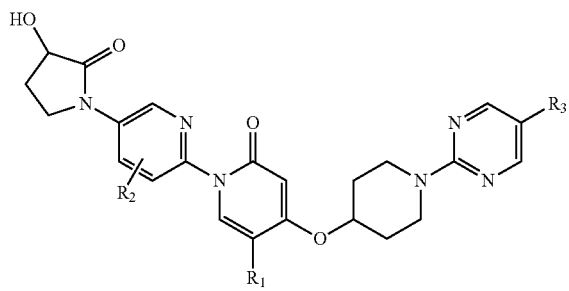

I enantiomer, diastereomer, tautomer, or salt thereof wherein:
$R_1$ is hydrogen or halo;
$R_2$ is $(C_1-C_{10})$alkyl; and
$R_3$ is halo or $(C_1-C_{10})$alkyl.

In one embodiment, the present invention provides a compound of Formula Ia:

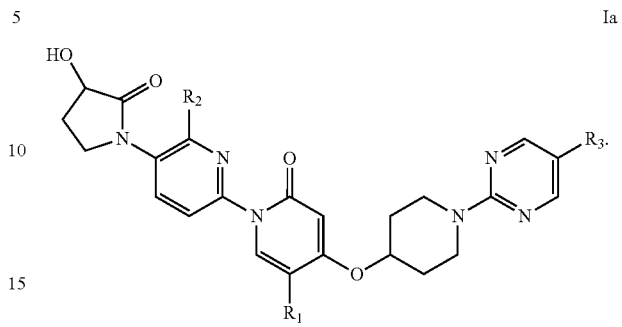

Ia

The terms "Formula I", "Formula Ia" and all embodiments thereof shall include enantiomers, diastereomers, solvates and salts thereof (particularly enantiomers, diastereomers and pharmaceutically acceptable salts thereof).

In another embodiment, the present invention provides a compound of Formula I or Ia, or an enantiomer, a diastereomer, or a pharmaceutically acceptable salt thereof, wherein $R_2$ is $(C_1-C_7)$alkyl.

In yet another embodiment, the present invention provides a compound of Formula I or Ia, or an enantiomer, a diastereomer, or a pharmaceutically acceptable salt thereof, wherein $R_2$ is $(C_1-C_6)$alkyl.

In still yet another embodiment, the present invention provides a compound of Formula I or Ia, or an enantiomer, a diastereomer, or a pharmaceutically acceptable salt thereof, wherein $R_2$ is $(C_1-C_5)$alkyl.

In one embodiment, the present invention provides a compound of Formula I or Ia, or an enantiomer, a diastereomer, or a pharmaceutically acceptable salt thereof, wherein:
$R_1$ is hydrogen or halo;
$R_2$ is $(C_1-C_5)$alkyl; and
$R_3$ is halo or $(C_1-C_7)$alkyl.

In another embodiment, the present invention provides a compound of Formula I or Ia, or an enantiomer, a diastereomer, or a pharmaceutically acceptable salt thereof, wherein:
$R_1$ is hydrogen or halo;
$R_2$ is methyl or ethyl; and
$R_3$ is halo or $(C_1-C_6)$alkyl.

In yet another embodiment, the present invention provides a compound of Formula I or Ia, or an enantiomer, a diastereomer, or a pharmaceutically acceptable salt thereof, wherein:
$R_1$ is hydrogen or Cl;
$R_2$ is methyl or ethyl; and
$R_3$ is halo or $(C_1-C_5)$alkyl.

In still yet another embodiment, the present invention provides a compound of Formula I or Ia, or an enantiomer, a diastereomer, or a pharmaceutically acceptable salt thereof, wherein:
$R_1$ is hydrogen or Cl;
$R_2$ is methyl or ethyl; and
$R_3$ is Cl or $(C_1-C_3)$alkyl.

In one embodiment, the present invention provides a compound of Formula I or Ia, or an enantiomer, a diastereomer, or a pharmaceutically acceptable salt thereof, wherein:
$R_1$ is hydrogen or Cl;
$R_2$ is methyl; and
$R_3$ is Cl or $(C_1-C_3)$alkyl.

In another embodiment, the present invention provides a compound of Formula I or Ia, or an enantiomer, a diastereomer, or a pharmaceutically acceptable salt thereof, wherein:
$R_1$ is hydrogen or halo;
$R_2$ is $(C_1-C_5)$alkyl; and
$R_3$ is halo or $(C_1-C_3)$alkyl.

In yet another embodiment, the present invention provides a compound of Formula I or Ia, or an enantiomer, a diastereomer, or a pharmaceutically acceptable salt thereof, wherein:
$R_1$ is hydrogen or halo;
$R_2$ is methyl or ethyl; and
$R_3$ is halo or $(C_1-C_3)$alkyl.

In still yet another embodiment, the present invention provides a compound of Formula I or Ia, or an enantiomer, a diastereomer, or a pharmaceutically acceptable salt thereof, wherein:
$R_1$ is hydrogen or Cl;
$R_2$ is methyl or ethyl; and
$R_3$ is halo or $(C_1-C_3)$alkyl.

In one embodiment, the present invention provides a compound of Formula I or Ia, or an enantiomer, a diastereomer, or a pharmaceutically acceptable salt thereof, wherein:
$R_1$ is hydrogen or Cl;
$R_2$ is methyl or ethyl; and
$R_3$ is Cl or $(C_1-C_3)$alkyl.

In another embodiment, the present invention provides a compound of Formula I or Ia, or an enantiomer, a diastereomer, or a pharmaceutically acceptable salt thereof, wherein:
$R_1$ is hydrogen or Cl;
$R_2$ is methyl; and
$R_3$ is Cl or $(C_1-C_3)$alkyl.

In another embodiment, the present invention provides a compound of Formula I or Ia, or an enantiomer, a diastereomer, or a pharmaceutically acceptable salt thereof, wherein the compound is selected from one of the examples, preferably Examples 1-4, more preferably, Examples 1 and 4.

For each of the embodiments described in this application, further and more particular values of the terms used in each of the embodiments may be selected from the following definitions; these values may be used individually in any of the embodiments or in any combination. It is noted that for any occurrences of "=O", these may be used with suitable accommodation in the bond structure at that site as will be appreciated by those skilled in the art.

In one embodiment, the present invention relates to methods of modulating the activity of the GPR119 G protein-coupled receptor comprising administering to a mammalian patient, for example, a human patient, in need thereof a therapeutically effective amount of a compound of Formula I or Ia, preferably, a compound selected from one of the examples, more preferably Examples 1-4, even more preferably, Examples 1 and 4, alone, or optionally, in combination with another compound of the present invention and/or at least one other type of therapeutic agent.

In one embodiment, the present invention relates to a method for preventing, modulating, or treating the progression or onset of diseases or disorders associated with the activity of the GPR119 G protein-coupled receptor comprising administering to a mammalian patient, for example, a human patient, in need of prevention, modulation, or treatment a therapeutically effective amount of a compound of Formula I or Ia, preferably, a compound selected from one of the examples, more preferably Examples 1-4, even more preferably, Examples 1 and 4, alone, or, optionally, in combination with another compound of the present invention and/or at least one other type of therapeutic agent.

Examples of diseases or disorders associated with the activity of the GPR119 G protein-coupled receptor that can be prevented, modulated, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dislipidemia, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy and glaucoma.

In another embodiment, the present invention relates to a method for preventing, modulating, or treating the progression or onset of diabetes, hyperglycemia, obesity, dyslipidemia, hypertension and cognitive impairment comprising administering to a mammalian patient, for example, a human patient, in need of prevention, modulation, or treatment a therapeutically effective amount of a compound of Formula I or Ia, preferably, a compound selected from one of the examples, more preferably Examples 1-4, even more preferably, Examples 1 and 4, alone, or, optionally, in combination with another compound of the present invention and/or at least one other type of therapeutic agent.

In another embodiment, the present invention relates to a method for preventing, modulating, or treating the progression or onset of diabetes, comprising administering to a mammalian patient, for example, a human patient, in need of prevention, modulation, or treatment a therapeutically effective amount of a compound of Formula I or Ia, preferably, a compound selected from one of the examples, more preferably Examples 1-4, even more preferably, Examples 1 and 4, alone, or, optionally, in combination with another compound of the present invention and/or at least one other type of therapeutic agent.

In yet another embodiment, the present invention relates to a method for preventing, modulating, or treating the progression or onset of hyperglycemia comprising administering to a mammalian patient, for example, a human patient, in need of prevention, modulation, or treatment a therapeutically effective amount of a compound of Formula I or Ia, preferably, a compound selected from one of the examples, more preferably Examples 1-4, even more preferably, Examples 1 and 4, alone, or, optionally, in combination with another compound of the present invention and/or at least one other type of therapeutic agent.

In still yet another embodiment, the present invention relates to a method for preventing, modulating, or treating the progression or onset of obesity comprising administering to a mammalian patient, for example, a human patient, in need of prevention, modulation, or treatment a therapeutically effective amount of a compound of Formula I or Ia, preferably, a compound selected from one of the examples, more preferably Examples 1-4, even more preferably, Examples 1 and 4, alone, or, optionally, in combination with another compound of the present invention and/or at least one other type of therapeutic agent.

In one embodiment, the present invention relates to a method for preventing, modulating, or treating the progression or onset of dyslipidemia comprising administering to a mammalian patient, for example, a human patient, in need of prevention, modulation, or treatment a therapeutically effective amount of a compound of Formula I or Ia, preferably, a compound selected from one of the examples, more preferably Examples 1-4, even more preferably, Examples 1 and 4, alone, or, optionally, in combination with another compound of the present invention and/or at least one other type of therapeutic agent.

In another embodiment, the present invention relates to a method for preventing, modulating, or treating the progression or onset of hypertension comprising administering to a mammalian patient, for example, a human patient, in need of prevention, modulation, or treatment a therapeutically effective amount of a compound of Formula I or Ia, preferably, a compound selected from one of the examples, more preferably Examples 1-4, even more preferably, Examples 1 and 4, alone, or, optionally, in combination with another compound of the present invention and/or at least one other type of therapeutic agent.

In another embodiment, the present invention relates to a formulated product, for example a spray dried dispersion, wherein the selected formulation is made by combining (a) a compound of Formula I or Ia, preferably, a compound selected from one of the examples, more preferably Examples 1-4, even more preferably, Examples 1 and 4 (using any of the compound embodiments listed above), and (b) a dipeptidyl peptidase-IV (DPP4) inhibitor (for example, a member selected from saxagliptin, sitagliptin, vildagliptin, linagliptin, dutogliptin and alogliptin).

In another embodiment, the present invention relates to a formulated product, for example a spray dried dispersion, wherein the selected formulation is made by combining (a) a compound of Formula I or Ia, preferably, a compound selected from one of the examples, more preferably Examples 1-4, even more preferably, Examples 1 and 4 (using any of the compound embodiments listed above), and (b) a dipeptidyl peptidase-IV (DPP4) inhibitor, wherein the DPP4 inhibitor is saxagliptin.

The present invention provides, at least in part, crystalline forms of the compounds of Formula I. Preferred embodiments of crystalline forms of the present invention are crystalline forms of the free base of (R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one, in particular in a pharmaceutically acceptable form. In certain preferred embodiments, crystalline forms of the free base are in substantially pure form. Preferred embodiments of crystalline forms of the free base are disclosed in Examples 7a, 7b and 7c as the N-1, N-2, and H2-3 Forms. A more preferred embodiment of crystalline forms of the free base is disclosed in Example 7a, the N-1 Form.

In still yet an even further embodiment, the first crystalline form of Compound I contains at least about 90 wt. %, preferably at least about 95 wt. %, and more preferably at least about 99 wt. %, based on weight of the first crystalline form, Form N-1.

In a still further embodiment, a substantially pure first crystalline form has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, the substantially pure first crystalline form has substantially pure phase homogeneity with less than about 1% of the total peak area of the experimentally measured PXRD pattern arising from peaks that are absent from the simulated PXRD pattern.

Samples of the crystalline forms may be provided with substantially pure phase homogeneity, indicating the presence of a dominant amount of a single crystalline form and optionally minor amounts of one or more other crystalline forms. The presence of more than one crystalline form in a sample may be determined by techniques such as powder X-ray diffraction (PXRD) or solid state nuclear magnetic resonance spectroscopy (SSNMR). For example, the presence of extra peaks in the comparison of an experimentally measured PXRD pattern with a simulated PXRD pattern may indicate more than one crystalline form in the sample. The simulated PXRD may be calculated from single crystal X-ray data. See Smith, D. K., "A FORTRAN Program for Calculating X-Ray Powder Diffraction Patterns", Lawrence Radiation Laboratory, Livermore, Calif., UCRL-7196 (April 1963).

Procedures for the preparation of crystalline forms are known in the art. The crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture.

The various forms described herein may be distinguishable from one another through the use of various analytical techniques known to one of ordinary skill in the art. Such techniques include, but are not limited to, X-ray powder diffraction (PXRD) and/or thermogravimetric analysis (TGA). Specifically, the forms may be characterized and distinguished using single crystal X-ray diffraction, which is based on unit cell measurements of a single crystal of a given form at a fixed analytical temperature. A detailed description of unit cells is provided in Stout et al. Chapter 3, X-Ray Structure Determination: A Practical Guide, MacMillan Co., New York (1968), which is herein incorporated by reference. Alternatively, the unique arrangement of atoms in spatial relation within the crystalline lattice may be characterized according to the observed fractional atomic coordinates. Another means of characterizing the crystalline structure is by powder X-ray diffraction analysis in which the diffraction profile is compared to a simulated profile representing pure powder material, both run at the same analytical temperature, and measurements for the subject form characterized as a series of 2θ values (usually four or more).

Other means of characterizing the form may be used, such as solid state nuclear magnetic resonance (SSNMR) spectroscopy, differential scanning calorimetry (DSC) and gross examination of the crystalline or amorphous morphology. These parameters may also be used in combination to characterize the subject form.

One of ordinary skill in the art will appreciate that an X-ray diffraction pattern may be obtained with a measurement error that is dependent upon the measurement conditions employed. In particular, it is generally known that intensities in an X-ray diffraction pattern may fluctuate depending upon measurement conditions employed and the shape or morphology of the crystal. It should be further understood that relative intensities may also vary depending upon experimental conditions and, accordingly, the exact order of intensity should not be taken into account. Additionally, a measurement error of diffraction angle for a conventional X-ray diffraction pattern is typically about 0.2° or less, preferably about 0.1° (as discussed hereinafter), and such degree of measurement error should be taken into account as pertaining to the aforementioned diffraction angles. Consequently, it is to be understood that the crystal forms of the instant invention are not limited to the crystal forms that provide X-ray diffraction patterns completely identical to the X-ray diffraction patterns depicted in the accompanying Figures disclosed herein. Any crystal forms that provide X-ray diffraction patterns substantially identical to those disclosed in the accompanying Figures fall within the scope of the present invention. The ability to ascertain substantial identities of X-ray diffraction patterns is within the purview of one of ordinary skill in the art.

The presence of reaction impurities and/or processing impurities may be determined by analytical techniques known in the art, such as, for example, chromatography, nuclear magnetic resonance spectroscopy, mass spectrometry or infrared spectroscopy.

Crystals of drugs, including polymorphs, methods of preparation, and characterization of drug crystals are discussed in Byrn, S. R. et al., Solid-State Chemistry of Drugs, 2nd Edition, SSCI, West Lafayette, Ind. (1999).

For crystallization techniques that employ solvent, the choice of solvent or solvents is typically dependent upon one or more factors, such as solubility of the compound, crystallization technique, and vapor pressure of the solvent. Combinations of solvents may be employed; for example, the compound may be solubilized into a first solvent to afford a solution, followed by the addition of an antisolvent to decrease the solubility of the compound in the solution and to afford the formation of crystals. An "antisolvent" is a solvent in which the compound has low solubility. Suitable solvents for preparing crystals include polar and nonpolar solvents.

In one embodiment of the invention, a crystalline form of (R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one is provided in substantially pure form. This crystalline form may be employed in pharmaceutical compositions which may optionally include one or more other components selected, for example, from the group consisting of excipients, carriers, and one of other active pharmaceutical ingredients or active chemical entities of different molecular structures.

In one embodiment, the N-1, N-2 and H2-3 Forms are characterized by unit cell parameters set forth in Table 1.

In yet an even further embodiment, the N-1 Form is characterized by fractional atomic coordinates substantially as listed in Table 2.

In yet an even further embodiment, the N-2 Form is characterized by fractional atomic coordinates substantially as listed in Table 3.

In yet an even further embodiment, the H2-3 Form is characterized by fractional atomic coordinates substantially as listed in Table 4.

Figure 1:
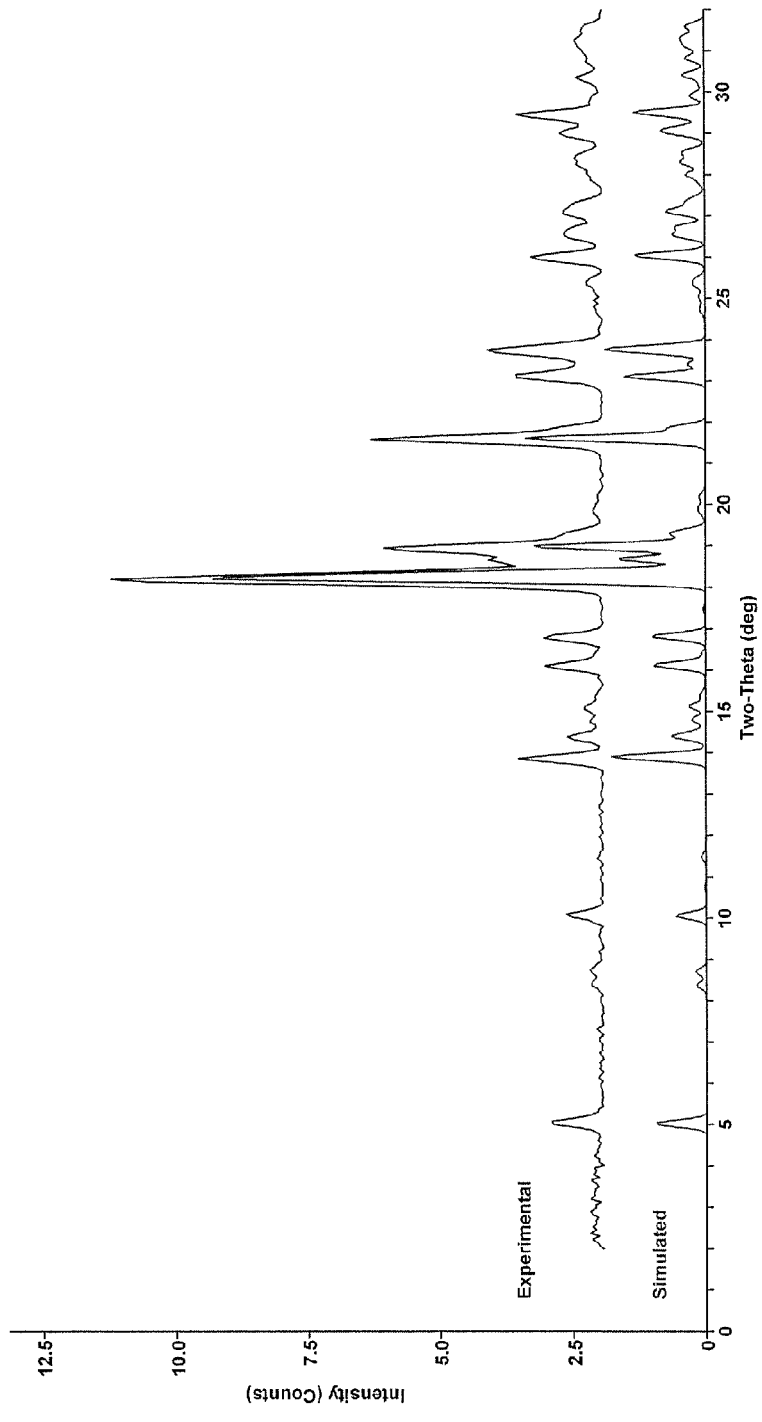
FIG. 1. Experimental and simulated powder X-ray diffraction patterns of (R)-5-chloro-4-((1-(5-chloropyrimidin-2-yl)

In another embodiment, the N-1 Form is characterized by a simulated PXRD pattern substantially in accordance with the pattern shown in FIG. 1 and/or by an observed PXRD pattern substantially in accordance with the pattern shown in FIG. 1.

In another embodiment, the N-2 Form is characterized by a simulated PXRD pattern substantially in accordance with the pattern shown in FIG. 2 and/or by an observed PXRD pattern substantially in accordance with the pattern shown in FIG. 2.

In another embodiment, the H2-3 Form is characterized by a simulated PXRD pattern substantially in accordance with the pattern shown in FIG. 3 and/or by an observed PXRD pattern substantially in accordance with the pattern shown in FIG. 3.

In a still further embodiment, the N-1 Form is characterized by a DSC thermogram substantially in accordance with that shown in FIG. 4.

In another embodiment, the N-2 Form is characterized by a DSC thermogram substantially in accordance with that shown in FIG. 5.

In yet another embodiment, the H2-3 Form is characterized by a DSC thermogram substantially in accordance with that shown in FIG. 6.

In still an even further embodiment, the N-1 Form exhibits a TGA thermogram substantially the same as shown in FIG. 7.

In still an even further embodiment, the N-2 Form exhibits a TGA thermogram substantially the same as shown in FIG. 8.

In still an even further embodiment, the H2-3 Form exhibits a TGA thermogram substantially the same as shown in FIG. 9.

In another embodiment, the N-1 Form is characterized by a solid state nuclear magnetic resonance spectra (ssNMR) substantially in accordance with the spectra shown in FIG. 10.

In another embodiment, the H2-3 Form is characterized by a solid state nuclear magnetic resonance spectra (ssNMR) substantially in accordance with the spectra shown in FIG. 11.

In one method to prepare crystals, (R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one is suspended and/or stirred in a suitable solvent to afford a slurry, which may be heated to promote dissolution. The term "slurry", as used herein, means a saturated solution of the free base, which may also contain an additional amount of the compound to afford a heterogeneous mixture of the compound and a solvent at a given temperature. Suitable solvents in this regard include, for example, polar aprotic solvents and polar protic solvents, and mixtures of two or more of these, as disclosed herein.

Seed crystals may be added to any crystallization mixture to promote crystallization. As will be clear to the skilled artisan, seeding is used as a means of controlling growth of a particular crystalline form or as a means of controlling the particle size distribution of the crystalline product. Accordingly, calculation of the amount of seeds needed depends on the size of the seed available and the desired size of an average product particle as described, for example, in Mullin, J. W. et al., "Programmed cooling of batch crystallizers", Chemical Engineering Science, 26:369-377 (1971). In general, seeds of small size are needed to effectively control the growth of crystals in the batch. Seeds of small size may be generated by sieving, milling, or micronizing of larger crystals, or by micro-crystallization of solutions. Care should be taken that milling or micronizing of crystals does not result in any change in crystallinity from the desired crystal form (i.e., change to amorphous or to another polymorph).

A cooled mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as SSNMR, DSC, PXRD, or the like, to assure formation of the preferred crystalline form of the product. The resulting crystalline form is typically produced in an amount of greater than about 70 weight % isolated yield, but preferably greater than 90 weight % based on the weight of (R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one originally employed in the crystallization procedure. The product may be co-milled or passed through a mesh screen to de-lump the product, if necessary.

Crystalline forms may be prepared directly from the reaction medium of the final process step for preparing (R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one. This may be achieved, for example, by employing in the final process step a solvent or mixture of solvents from which the free base may be crystallized. Alternatively, crystalline forms may be obtained by distillation or solvent addition techniques. Suitable solvents for this purpose include any of those solvents described herein, including protic polar solvents, such as alcohols, and aprotic polar solvents, such as ketones.

By way of general guidance, the reaction mixture may be filtered to remove any undesired impurities, inorganic salts, and the like, followed by washing with reaction or crystallization solvent. The resulting solution may be concentrated to remove excess solvent or gaseous constituents. If distillation is employed, the ultimate amount of distillate collected may vary, depending on process factors including, for example, vessel size, stirring capability, and the like. By way of general guidance, the reaction solution may be distilled to about $\frac{1}{10}$ the original volume before solvent replacement is carried out. The reaction may be sampled and assayed to determine the extent of the reaction and the wt % product in accordance with standard process techniques. If desired, additional reaction solvent may be added or removed to optimize reaction concentration. Preferably, the final concentration is adjusted to about 50 wt % at which point a slurry typically results.

It may be preferable to add solvents directly to the reaction vessel without distilling the reaction mixture. Preferred solvents for this purpose are those which may ultimately participate in the crystalline lattice, as discussed above in connection with solvent exchange. Although the final concentration may vary depending on desired purity, recovery and the like, the final concentration of the free base in solution is preferably about 4% to about 7%. The reaction mixture may be stirred following solvent addition and simultaneously warmed. By way of illustration, the reaction mixture may be stirred for about 1 hour while warming to about 70° C. The reaction is preferably filtered hot and washed with either the reaction solvent, the solvent added or a combination thereof. Seed crystals may be added to any crystallization solution to initiate crystallization.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I or Ia may display superior activity compared with the other. Thus, all of the stereochemistries are considered to be a part of the present invention. When required, separation of the racemic material can be achieved by high performance liquid chromatography (HPLC) using a chiral column or by a resolution using a resolving agent such as camphonic chloride as in Young, S. D. et al., *Antimicrobial Agents and Chemotherapy*, 2602-2605 (1995).

To the extent that compounds of Formula I or Ia, and salts thereof, may exist in their tautomeric form, all such tautomeric forms are contemplated herein as part of the present invention.

When any variable (e.g., =O) occurs more than one time in any constituent or formula for a compound, its definition at each occurrence is independent of its definition at every other occurrence. Thus, for example, if a group is shown to be substituted with (=O)$_{n1}$ and n1 is 0 or 1, then said group may optionally be substituted with up to one =O group. Also, combinations of substituents and/or variables are permissible only if such combinations result in stable compounds.

Combinations of substituents and/or variables are permissible only if such combinations result in stable compounds.

As used herein, "alkyl" is intended to include both branched and straight-chain saturated aliphatic hydrocarbon groups in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, the various branched chain isomers thereof.

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th Edition, Mack Publishing Company, Easton, Pa., p. 1418 (1985), the disclosure of which is hereby incorporated by reference.

Any compound that can be converted in vivo to provide the bioactive agent (i.e., a compound of Formula I) is a prodrug within the scope and spirit of the invention.

In addition, compounds of Formula I or Ia, preferably, a compound selected from one of the examples, more preferably Examples 1-4, even more preferably, Examples 1 and 4, are, subsequent to their preparation, preferably isolated and purified to obtain a composition containing an amount by weight equal to or greater than 99% of said compound ("substantially pure" compound), which is then used or formulated as described herein. Such "substantially pure" compounds of Formula I or Ia, preferably, a compound selected from one of the examples, more preferably Examples 1-4, even more preferably, Examples 1 and 4, are also contemplated herein as part of the present invention.

All stereoisomers of the compounds of the instant invention are contemplated, either in admixture or in pure or substantially pure form. The compounds of the present invention can have asymmetric centers at any of the sulfur or carbon atoms including any one of the R substituents and/or exhibit polymorphism. Consequently, compounds of the present invention can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^{2}$H and $^{3}$H, carbon such as $^{11}$C, $^{13}$C, and $^{14}$C, chlorine, such as $^{36}$Cl, fluorine such as $^{18}$F, iodine, such as $^{123}$I and $^{125}$I, nitrogen, such as $^{13}$N and $^{15}$N, oxygen, such as $^{15}$O, $^{17}$O, and $^{18}$O, phosphorus, such as $^{32}$P, and sulfur, such as $^{35}$S. Certain isotopically-labeled compounds of the invention, for example, those incorporating a radioactive isotope, are useful in drug and/or substrate tissue distribution studies. The radioactive isotopes tritium, $^{3}$H, and carbon-14, $^{14}$C, are particularly useful for this purpose in view of their ease of incorporation and ready means of detection. Substitution with heavier isotopes such as deuterium, $^{2}$H, may afford certain therapeutic advantages resulting from greater metabolic stability, for example, increase in vivo half-life or reduced dosage requirements, and hence may be preferred in some circumstances. Substitution with positron emitting isotopes, such as $^{11}$C, $^{18}$F, $^{15}$O, and $^{13}$N, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to modulate GPR119 or effective to treat or prevent various disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) modulating the disease-state, i.e., arresting it development; and/or (c) relieving the disease-state, i.e., causing regression of the disease state.

The names used herein to characterize a specific form, e.g., "N-1", should not be considered limiting with respect to any other substance possessing similar or identical physical and chemical characteristics, but rather it should be understood that these designations are mere identifiers that should be interpreted according to the characterization information also presented herein.

As used herein "polymorph" refers to crystalline forms having the same chemical composition but different spatial arrangements of the molecules, atoms, and/or ions forming the crystal.

As used herein "amorphous" refers to a solid form of a molecule, atom, and/or ions that is not crystalline. An amorphous solid does not display a definitive X-ray diffraction pattern.

The term "negligible weight loss", as employed herein, as characterized by TGA indicates the presence of a neat (non-solvated) crystal form.

Synthesis

The compounds of the present invention can be prepared in a number of ways well known to one skilled in the art of organic synthesis. The compounds of the present invention can be synthesized using the methods described below, together with synthetic methods known in the field of synthetic organic chemistry, or variations thereof, as appreciated by those skilled in the art. Preferred methods include, but are not limited to, those described below. All references cited herein are hereby incorporated in their entirety by reference.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the molecule must be compatible with the reagents and reactions proposed. Not all compounds of Formula I falling into a given class may be compatible with some of the reaction conditions required in some of the methods described. Such restrictions to the substituents, which are compatible with the reaction conditions, will be readily apparent to one skilled in the art and alternate methods must be used.

Scheme 1

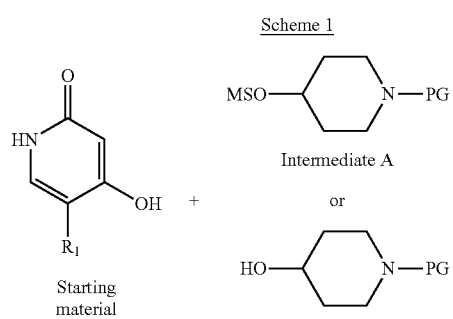

Intermediate A

Intermediate B

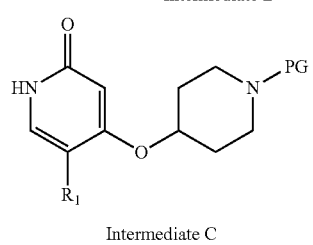

Intermediate C

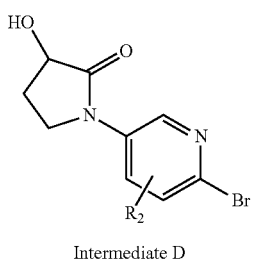

Intermediate D

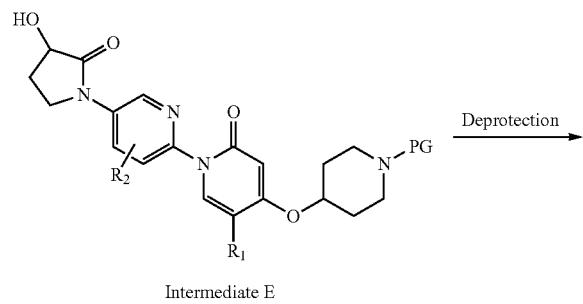

Intermediate E

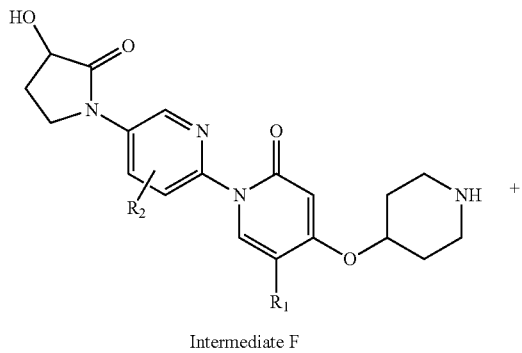

Intermediate F

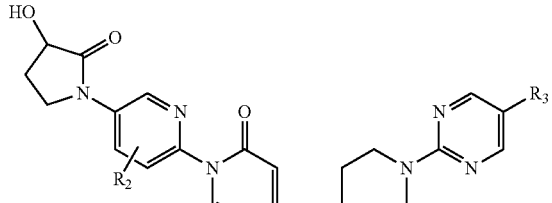

Intermediate G

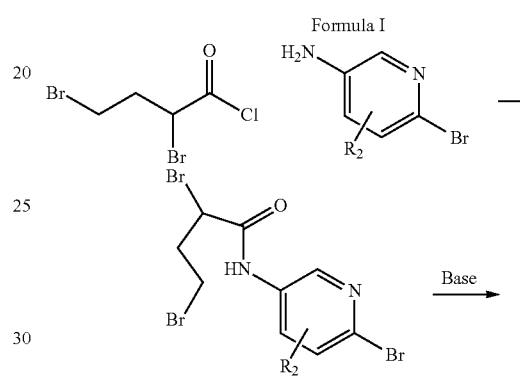

Formula I

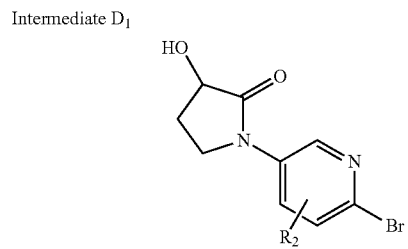

Intermediate D₁

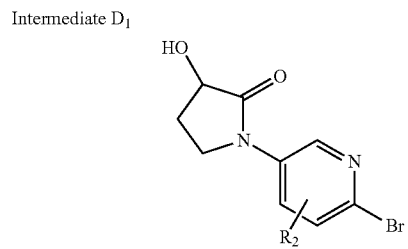

Intermediate D

Compounds of Formula I may be prepared by procedures depicted in Scheme 1. The appropriately substituted commercial pyridones can be reacted with intermediate A, obtained from commercial sources, in the presence of a base such as $K_2CO_3$ or sodium hydride in a suitable solvent such as DMF, THF, etc. or intermediate B, obtained from commercial sources, using Mitsunobu reaction conditions well known to one skilled in the art of organic synthesis to yield intermediate C. Coupling of intermediate C and intermediate D can be accomplished in the presence of a ligand such as but not limited to 8-hydroxyquinoline, CuI (I), and a base such as $K_2CO_3$ in a suitable solvent such as DMF, DMSO, etc., at an elevated temperature to yield intermediate E. Intermediate D can be synthesized by procedures depicted in Scheme 1 with a straight forward acetylation of the appropriately substituted commercial aminopyridines with 2,4-dibromobutyryl chloride, then cyclization and hydrolysis to intermediate D with base. Removal of the protecting group from intermediate E can be carried out with appropriate reagents well known to those skilled in the art (for specific details see Greene et al., *Protecting Groups in Organic Synthesis*, John Wiley & Sons Inc. (1991)). The deprotected product, intermediate F, can then be combined with intermediate G, which are commercially available or can be prepared by many methods known in the art, in the presence of a base, such as triethylamine or K$_2$CO$_3$, which are routine for those skilled in the art of organic synthesis to afford compounds of Formula I.

Scheme 2

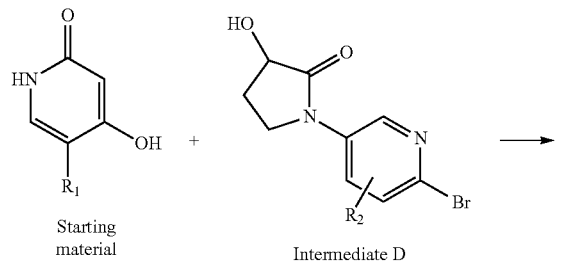

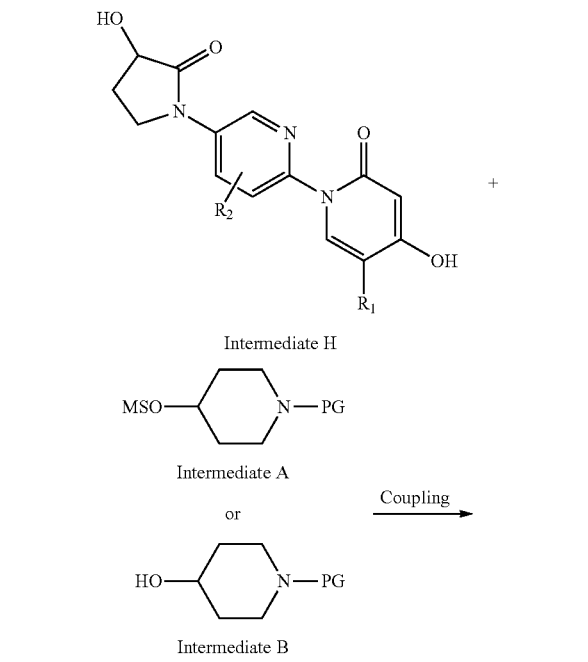

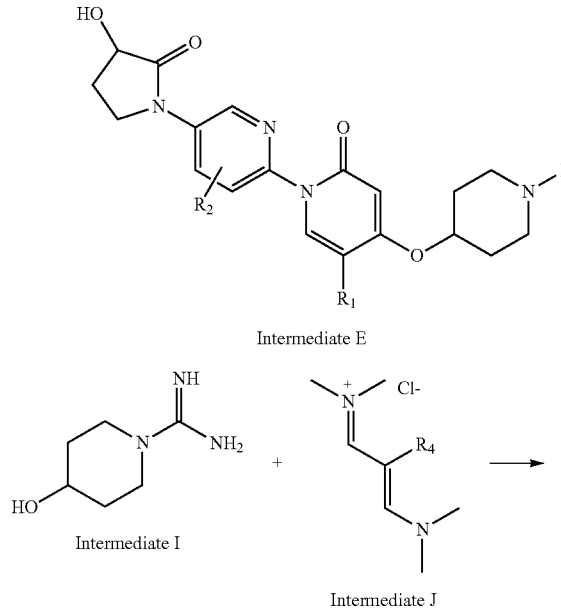

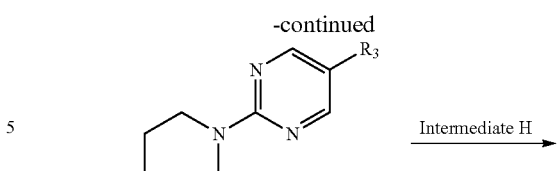

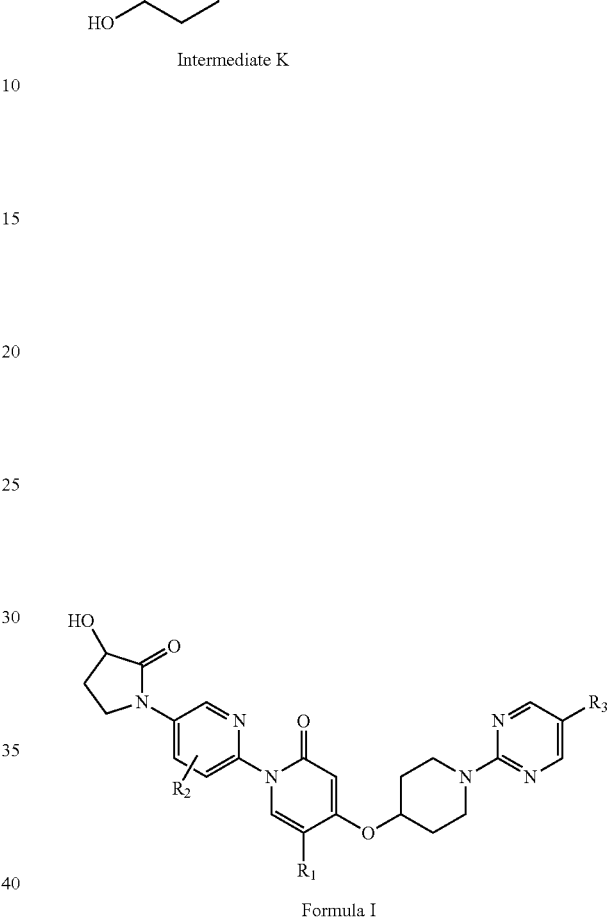

Alternatively, compounds of Formula I may be prepared by procedures depicted in Scheme 2. The appropriately substituted commercial pyridones can be reacted with intermediate D in the presence of a ligand such as but not limited to 1,10-phenanthroline, CuI (I), and a base such as K$_2$CO$_3$, in a suitable solvent such as DMF, DMSO, etc., at an elevated temperature to yield intermediate H. Coupling of the intermediate H and intermediates A or B can be accomplished using conditions described above for step 1 of Scheme 1 to yield intermediate E. Intermediate E can then be carried forward according to Scheme 1 to provide the final products of Formula I. Alternatively, compounds of Formula 1 may be obtained by coupling intermediate K with intermediate H using Mitsunobu reaction conditions well known to one skilled in the art of organic synthesis. Intermediate K can be synthesized by condensation of intermediate I (obtained according to procedures described by Bernatowicz et al., *JOC*, 57:2497 (1992)) and intermediate J (obtained according to procedures described by Yamanaka et al., *Tetrahedron Letters*, 37:1829 (1996)) in a solvent such as but not limited to DMF and a base such as but not limited to triethylamine.

Scheme 3

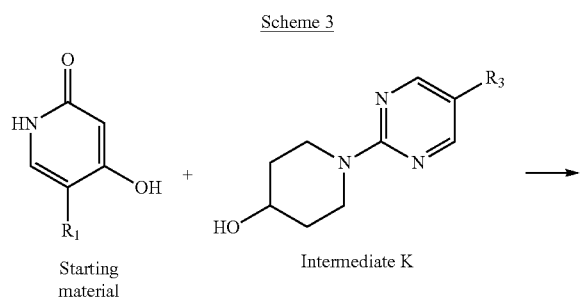

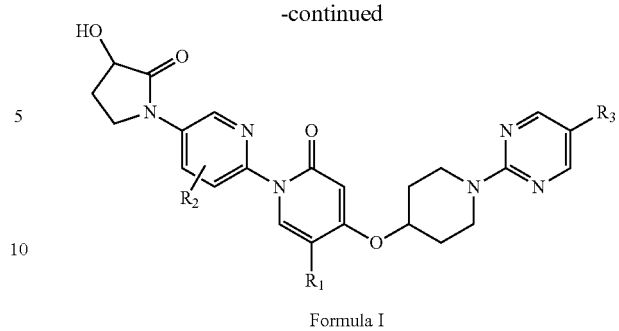

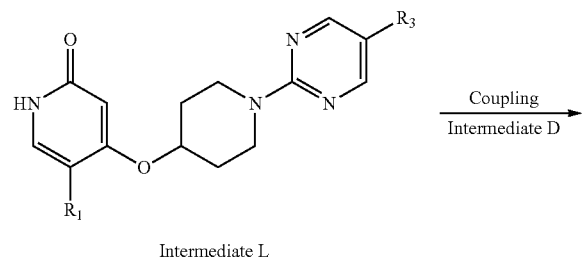

Alternatively, compounds of Formula I may be prepared by procedures depicted in Scheme 3. The appropriately substituted commercial pyridones can be reacted with intermediate K, described in Scheme 2, using Mitsunobu reaction conditions well known to one skilled in the art of organic synthesis to yield intermediate L. Coupling of intermediate L and intermediate D, described in Scheme 2, can be accomplished in the presence of a ligand such as but not limited to 8-hydroxyquinoline, CuI (I), and a base such as $K_2CO_3$ in a suitable solvent such as DMF, DMSO, etc., at an elevated temperature to provide the final products of Formula I.

Scheme 4

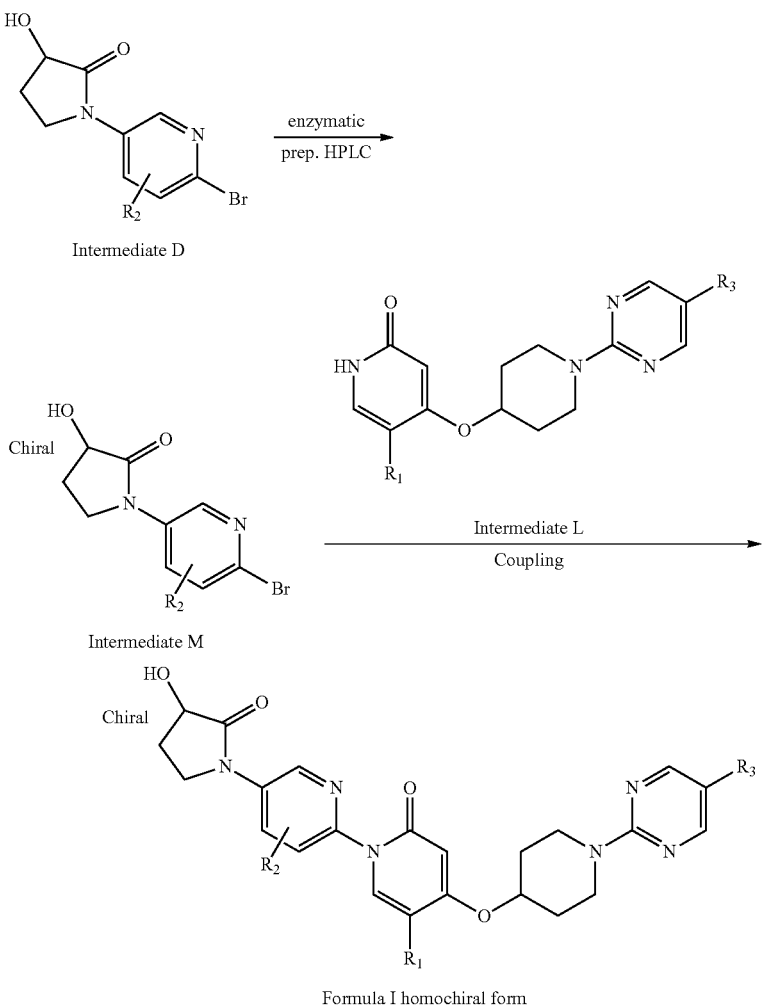

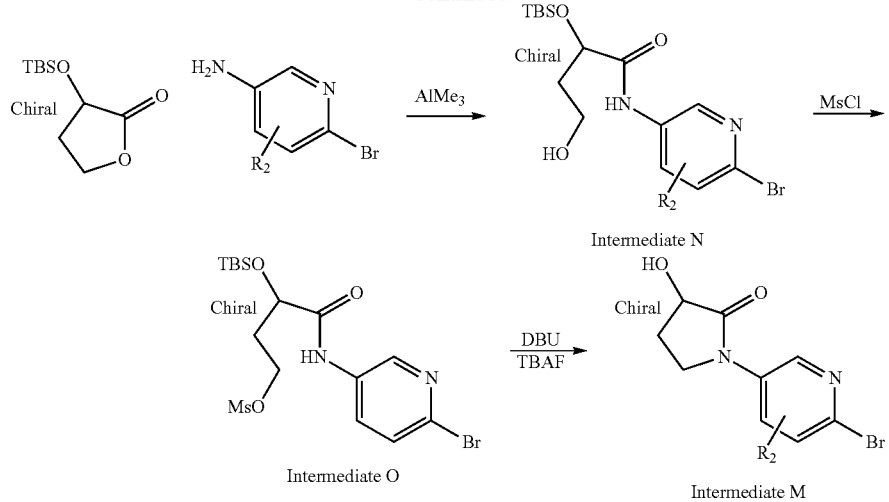

The homochiral compounds of Formula I can be obtained by enzymatic resolution or chiral separation of Formula I. Alternatively, they may also be prepared by procedures depicted in Scheme 4 by coupling of intermediate L and the homochiral material of intermediate D (named as intermediate M) in the presence of a ligand such as but not limited to 8-hydroxyquinoline, CuI (I), and a base such as $K_2CO_3$ in a suitable solvent such as DMF, DMSO, etc., at an elevated temperature. Intermediate M can be obtained by enzymatic resolution or chiral separation of intermediated D. Alternatively, intermediate M can be obtained synthetically by procedures depicted in Scheme 4. The TBS protected commercial hydroxylactone can be reacted with suitable aminopyridines, obtained from commercial sources, in the presence of a Lewis acid such as $AlMe_3$ in a suitable solvent such as DCM, THF, etc. to yield intermediate N. Mesylation of intermediate N with MsCl to yield intermediate O, which undergoes cyclization by treatment with a base such as DBU and followed by the deprotection of TBS group with TBAF to provide intermediate M.

EXAMPLES

The following Examples are offered as illustrative as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the Schemes and other methods disclosed herein or may be prepared using the same.

As appropriate, reactions were conducted under an atmosphere of dry nitrogen (or argon). For anhydrous reactions, DRISOLV® solvents from EM were employed. For other reactions, reagent grade or HPLC grade solvents were utilized. Unless otherwise stated, all commercially obtained reagents were used as received.

LC/MS measurements were obtained using a Shimadzu HPLC/Waters ZQ single quadrupole mass spectrometer hybrid system. Data for the peak of interest are reported from positive-mode electrospray ionization. NMR (nuclear magnetic resonance) spectra were typically obtained on Bruker or JEOL 400 MHz and 500 MHz instruments in the indicated solvents. All chemical shifts are reported in ppm from tetramethylsilane with the solvent resonance as the internal standard. $^1$H-NMR spectral data are typically reported as follows: chemical shift, multiplicity (s=singlet, br s=broad singlet, d=doublet, dd=doublet of doublets, t=triplet, q=quartet, sep=septet, m=multiplet, app=apparent), coupling constants (Hz), and integration.

One of skill in the art will recognize the standard abbreviations utilized herein, throughout the specification. For ease of reference, the abbreviations include, but are not necessarily limited to: sat.=saturated, HPLC=high-performance liquid chromatography, AP=area percent, KF=Karl-Fischer, RT=room temperature, mmol=millimoles, MS=mass spectroscopy, $CDCl_3$=chloroform, NMP=N-methylpyrrolidone, TEA=triethylamine, IPA=isopropyl alcohol, TFA=trifluoroacetic acid, HCl=hydrochloric acid, EtOAc=ethyl acetate, $CH_2Cl_2$=methylene chloride, THF=tetrahydrofuran, DMF=N,N-dimethylformamide, $SiO_2$=silica dioxide, NaOH=sodium hydroxide, DMSO=dimethylsulfoxide, °C.=degrees Celsius, g=gram or grams, mg=milligram or milligrams, mm=millimeter, mL (or ml)=milliliter or milliliters, h=hour or hours, M=molar, N=normal, min=minute or minutes, MHz=megahertz, tlc=thin layer chromatography, v/v=volume to volume ratio, and ca.=about.

"α", "β", "R" and "S" are stereochemical designations familiar to those skilled in the art.

Preparation of Intermediate 1

5-chloro-4-(piperidin-4-yloxy)pyridin-2(1H)-one hydrochloride

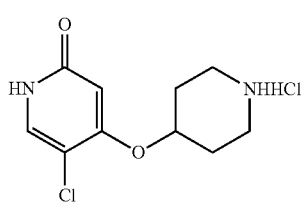

Step A: Preparation of tert-butyl 4-(5-chloro-2-oxo-1,2-dihydropyridin-4-yloxy)piperidine-1-carboxylate

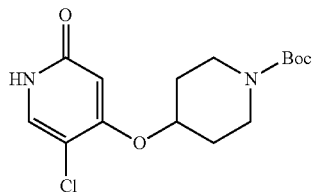 [SMILES: CC(C)(C)OC(=O)N1CCC(Oc2cc(=O)[nH]cc2Cl)CC1]

A 500 mL round bottom flask was charged with 5-chloro-4-hydroxypyridin-2(1H)-one (10 g, 68.7 mmol), t-butyl 4-hydroxypiperidine-1-carboxylate (16.59 g, 82 mmol), triphenylphosphine (27.0 g, 103 mmol) and DMF (200 ml). This mixture was stirred for 40 minutes to form a clear and homogeneous solution. The solution was then cooled to 0° C. and diisopropyl azodicarboxylate (16.23 mL, 82 mmol) was added drop-wise while maintaining the temperature below 20° C. during the addition. After the addition, the reaction mixture was allowed to warm to room temperature overnight. The reaction was then heated to 60° C. for 0.5 hours. After cooling the reaction mixture to room temperature, the DMF was distilled from the reaction under vacuum at 50° C. to yield brownish, viscous oil. The oil was dissolved in 300 mL of chloroform and then was washed with dilute sodium bicarbonate (pH 8-10) (3×50 mL). The chloroform layer was directly concentrated to afford a light yellow viscous oil, which was partitioned between 250 mL of diethyl ether and 70 mL of 1 N NaOH. The aqueous phase was extracted thoroughly with diethyl ether until LC/MS showed no triphenylphosphine oxide or other impurities in the aqueous layer. The aqueous layer was purged with nitrogen to remove residual ether and then acidified slowly with 1 N HCl (~70 mL) to pH 5 followed by cooling to 0° C. for 2 hours. The precipitates were collected by filtration, washed with ice water (2×20 mL), and air dried overnight. The light yellow solid was further vacuum dried at 40° C. to a constant weight to yield t-butyl 4-(5-chloro-2-oxo-1,2-dihydropyridin-4-yloxy)piperidine-1-carboxylate (13.2 g, 40.1 mmol, 58.4% yield) as a light yellow solid. $^1$H-NMR (CDCl$_3$, 400 MHz) δ 12.5 (br, s, 1H), 7.19 (s, 1H), 5.75 (s, 1H), 4.34-4.41 (m, 1H), 3.40-3.48 (m, 2H), 3.26-3.37 (m, 2H), 1.71-1.83 (m, 2H), 1.60-1.71 (m, 2H), 1.32 (s, 9H); MS m/e 329 (M+H$^+$), 273 (M+H$^+$-t-butyl).

Step B: Preparation of Intermediate 1

A 250 mL round bottom flask was charged with tert-butyl 4-(5-chloro-2-oxo-1,2-dihydropyridin-4-yloxy)piperidine-1-carboxylate (1.644 g, 5.0 mmol) and DCM (25 mL) and slurried for 15 minutes. 4N HCl in Dioxane (3.75 mL, 15.0 mmol) was then added at 0° C. and the reaction mixture was allowed to warm to room temperature and stirred overnight. EtOAc (25 mL) was added to the reaction mixture. The product was collected by filtration, thoroughly rinsed with ethyl acetate, and dried under vacuum overnight to yield Intermediate 1 (1.23 g, 91% yield) as a white solid. $^1$H NMR (400 MHz, MeOD) δ 8.12 (s, 1H), 6.65 (s, 1H), 5.02-5.34 (m, 1H), 3.33-3.47 (m, 4H), 2.23-2.42 (m, 2H), 2.07-2.22 (m, 2H); MS m/e 229 (M+H$^+$).

Preparation of Intermediate 2

5-Chloro-4-((1-(5-chloropyrimidin-2-yl)piperidin-4-yl)oxy)pyridin-2(1H)-one

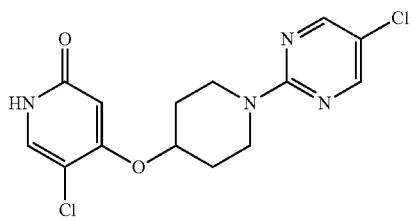 [SMILES: O=c1cc(OC2CCN(c3ncc(Cl)cn3)CC2)c(Cl)c[nH]1]

A 250 mL round bottom flask was charged with 5-chloro-4-(piperidin-4-yloxy)pyridin-2(1H)-one hydrochloride (3.0 g, 13.12 mmol), 5-chloro-2-iodopyrimidine (3.47 g, 4.43 mmol) and TEA (3.66 mL, 26.2 mmol) in CH$_3$CN (25 mL). The resulting suspension was heated at 70° C. under argon overnight. After cooling the reaction mixture to room temperature, the product was collected by filtration, thoroughly rinsed with methanol, and dried under vacuum overnight to yield Intermediate 2 (3.86 g, 84% yield) as a white solid. $^1$H NMR (400 MHz, CHLOROFORM-d) δ 12.48 (br s, 1H), 7.79-8.66 (m, 2H), 7.36 (s, 1H), 5.97 (s, 1H), 4.38-4.98 (m, 1H), 3.40-4.16 (m, 4H), 1.77-2.44 (m, 4H); MS (ESI) 341 (M+H).

Preparation of Intermediate 3

5-chloro-4-((1-(5-propylpyrimidin-2-yl)piperidin-4-yl)oxy)pyridin-2(1H)-one

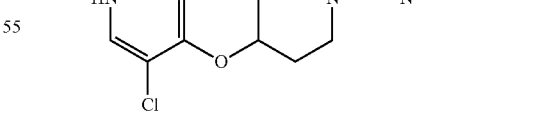

Following the same procedures as described in Intermediate 2, Intermediate 3 was prepared in 73% yield as a white solid by substituting 5-chloro-2-iodopyrimidine with 2-chloro-5-propylpyrimidine. $^1$H NMR (400 MHz, CHLOROFORM-d) δ 12.47-13.24 (m, 1H), 8.16 (s, 2H), 7.35 (s, 1H), 5.97 (s, 1H), 4.55-4.71 (m, 1H), 3.95-4.18 (m, 2H), 3.65-3.91 (m, 2H), 2.31-2.48 (m, 2H), 1.97-2.13 (m, 2H), 1.82-1.97 (m, 2H), 1.58 (d, J=7.58 Hz, 2H), 0.94 (t, J=7.33 Hz, 3H); MS (ESI) 349 (M+H).

Preparation of Intermediate 4

1-(6-bromo-2-methylpyridin-3-yl)-3-hydroxypyrrolidin-2-one

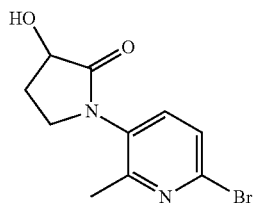

Step A: Preparation of 3-bromo-1-(6-bromo-2-methylpyridin-3-yl)pyrrolidin-2-one

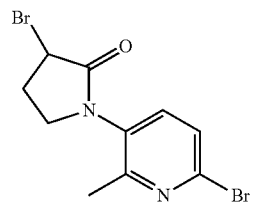

A 500 mL round-bottom flask was charged with 6-bromo-2-methylpyridin-3-amine (8.15 g, 43.6 mmol), THF (180 mL) and triethylamine (9.72 mL, 69.7 mmol). The mixture was cooled to 0° C. and 2,4 dibromobutanoyl chloride (6.39 mL, 48.4 mmol) in THF (45 mL) was added dropwise into the reaction mixture over 30 min. A LC/MS analysis indicated the consumption of the starting material in 1 hour at room temperature. To the reaction mixture was added tetrabutylammonium bromide (0.702 g, 2.179 mmol), followed by 20 mL of 5 M aq KOH solution dropwise. The reaction mixture was stirred at room temperature under argon overnight. A LC/MS analysis confirmed the reaction was complete. Ethyl acetate (50 mL) was added to the reaction. The organic layer was separated and washed with water (50 mL), brine (50 mL), dried over MgSO$_4$, filtered and concentrated to a dark solid (18.5 g), which was used directly to next step. MS (ESI) 334 (M+H).

Step B: Preparation of 1-(6-bromo-2-methylpyridin-3-yl)-2-oxopyrrolidin-3-yl acetate

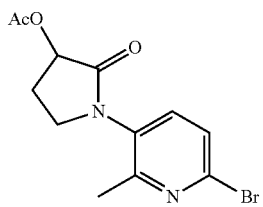 [SMILES: CC(=O)OC1CCN(c2ccc(Br)nc2C)C1=O]

A 500 mL round-bottom flask was charged with crude 3-bromo-1-(6-bromo-2-methylpyridin-3-yl)pyrrolidin-2-one from step A (18.5 g), THF (50 mL), 18-Crown-6 (576 mg, 2.18 mmol) and KOAc (12.84 g, 131 mmol). The mixture was heated at 70° C. under argon overnight. After cooling the reaction mixture to room temperature, ethyl acetate (50 mL) was added. The organic layer was separated and washed with water (50 mL), brine (50 mL), dried over MgSO$_4$, filtered and concentrated to a dark solid, which was purified by flash chromatography (silica gel, 20-100% ethyl acetate/hexane) to give 1-(6-bromo-2-methylpyridin-3-yl)-2-oxopyrrolidin-3-yl acetate (8.9 g, 65% yield for two steps) as white solid. $^1$H NMR (400 MHz, CHLOROFORM-d) δ 7.38 (q, J=8.3 Hz, 3H), 5.43 (t, J=8.2 Hz, 1H), 3.47-4.03 (m, 3H), 2.62-2.90 (m, 1H), 2.38-2.56 (m, 4H), 2.06-2.32 (m, 5H); MS (ESI) 314 (M+H).

Step C: Preparation of Intermediate 4

A 250 mL round bottom flask was charged with 1-(6-bromo-2-methylpyridin-3-yl)-2-oxopyrrolidin-3-yl acetate (7.5 g, 23.95 mmol) and K$_2$CO$_3$ (4.30 g, 31.1 mmol) in methanol (25 mL). The resulting suspension was stirred at room temperature under argon for 2 hours. Ethyl acetate (50 mL) and water (25 mL) were added to the reaction. The organic layer was separated. The aq. layer was extracted with ethyl acetate (50 mL×4). The combined organic phases were dried over MgSO$_4$, filtered and concentrated to a tan solid, which was thoroughly rinsed with ether, and dried under vacuum overnight to yield Intermediate 4 (5.2 g, 76% yield) as a white solid. $^1$H NMR (400 MHz, CHLOROFORM-d) δ 7.30-7.44 (m, 2H), 4.45-4.67 (m, 1H), 3.53-3.81 (m, 3H), 2.56-2.71 (m, 1H), 2.44 (s, 3H), 2.14-2.30 (m, 1H); MS (ESI) 272 (M+H).

Preparation of Intermediate 5

4-((1-(5-chloropyrimidin-2-yl)piperidin-4-yl)oxy)pyridin-2(1H)-one

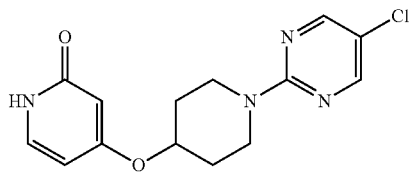 [SMILES: O=c1cc(OC2CCN(c3ncc(Cl)cn3)CC2)cc[nH]1]

Step A: Preparation of tert-butyl 4-(2-oxo-1,2-dihydropyridin-4-yloxy)piperidine-1-carboxylate A 250 mL round bottom flask was charged with 4-hydroxypyridin-2(1H)-one (6.13 g, 55.1 mmol), tert-butyl 4-(methylsulfonyloxy)piperidine-1-carboxylate (12.83 g, 45.9 mmol) (prepared according to the procedure described in patent application WO-2009/012275), K$_2$CO$_3$ (14.60 g, 106 mmol) and DMSO (56 mL). The mixture was heated to 100° C. for 3 hours and then allowed to cool to room temperature overnight. The resulting mixture was diluted with H$_2$O (300 mL) and extracted with EtOAc (2×150 mL). The organic layers were combined and concentrated in vacuo to a white solid. The solid was purified by flash chromatography (SiO$_2$, 0-100% EtOAc in CH$_2$Cl$_2$ and then SiO$_2$, 0-10% MeOH in CH$_2$Cl$_2$) to yield tert-butyl 4-(2-oxo-1,2-dihydropyridin-4-yloxy)piperidine-1-carboxylate (6.05 g, 45% yield) as a white solid. $^1$H NMR (400 MHz, CHLOROFORM-d) δ 12.34 (br. s., 1H) 7.21 (d, J=7.28 Hz, 1H) 5.96 (dd, J=7.28, 2.51 Hz, 1H) 5.87 (d, J=2.26 Hz, 1H) 4.35-4.58 (m, 1H) 3.59-3.80 (m, 2H) 3.17-3.41 (m, 2H) 1.87-2.08 (m, 2H) 1.65-1.87 (m, 2H) 1.47 (s, 9H). MS (ESI) 295 (M+H).

Step B: Preparation of 4-(piperidin-4-yloxy)pyridin-2(1H)-one hydrochloride

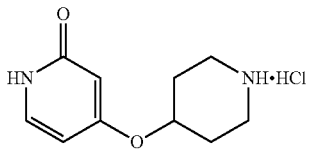

A 100 mL round bottom flask was charged with tert-butyl 4-(2-oxo-1,2-dihydropyridin-4-yloxy)piperidine-1-carboxylate (1.36 g, 4.62 mmol) and hydrogen chloride (37% in H$_2$O, 4 mL). The mixture was stirred at room temperature for 15 min and then concentrated in vacuo to yield 4-(piperidin-4-yloxy)pyridin-2(1H)-one hydrochloride (1.07 g, 100% yield) as a white solid. $^1$H NMR (400 MHz, DMSO-d6) δ 9.30 (br. s., 2H) 7.64 (d, J=7.28 Hz, 1H) 6.37 (dd, J=7.28, 2.51 Hz, 1H) 6.28 (d, J=2.51 Hz, 1H) 4.57-4.96 (m, 1H) 3.11-3.36 (m, 2H) 2.85-3.11 (m, 2H) 2.00-2.29 (m, 2H) 1.64-1.98 (m, 2H). MS (ESI) 195 (M+H).

Step C: Preparation of Intermediate 5

A 100 mL round bottom flask was charged with 4-(piperidin-4-yloxy)pyridin-2(1H)-one hydrochloride (1.80 g, 6.11 mmol), DMF (12 mL), diisopropylethylamine (2.4 mL, 14 mmol) and 5-chloro-2-iodopyrimidine (1.33 g, 5.55 mmol). The mixture was stirred at room temperature overnight. The mixture was then heated to 100° C. for 4 hours. After the reaction mixture was allowed to cool to room temperature, it was stirred for 1 day at room temperature. The reaction mixture was concentrated in vacuo to a yellow oil. The oil was dissolved in EtOAc (150 mL) and washed with NaHCO$_3$ (150 ml). After separation, the aqueous layer was extracted with CH$_2$Cl$_2$ (3×100 mL). The organic layers were combined and concentrated in vacuo to a yellow solid. To the solid was added CH$_2$Cl$_2$ and the resulting slurry was heated to reflux. After cooling to room temperature the solvent was decanted. The resulting solid was slurried one more time with CH$_2$Cl$_2$. After decanting of the CH$_2$Cl$_2$, the solid was dried in vacuo to yield intermediate 5 (0.814 g, 57% yield) as an off-white solid. $^1$H NMR (400 MHz, DMSO-d6) δ 11.07 (br. s., 1H), 8.41 (s, 2H), 7.23 (d, J=7.15 Hz, 1H), 5.70-5.93 (m, 2H), 4.68 (tt, J=3.85, 7.97 Hz, 1H), 4.07-4.23 (m, 2H), 3.43-3.59 (m, 2H), 1.91-2.05 (m, 2H), 1.50-1.69 (m, 2H). MS (ESI) 307 (M+H).

Example 1

5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one

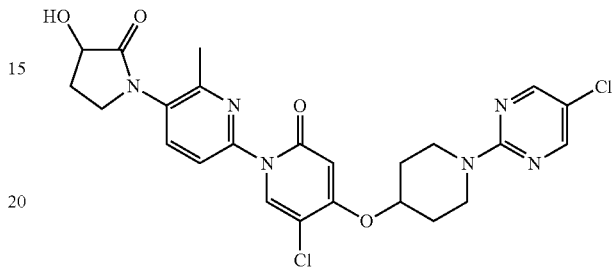

Intermediate 2 (1.23 g, 3.61 mmol) was charged into a 20 mL microwave vial with DMSO (15 mL) and Intermediate 4 (1.08 g, 3.97 mmol), quinolin-8-ol (209 mg, 1.44 mmol), copper (I) iodide (275 mg, 1.44 mmol) and K$_2$CO$_3$ (648 mg, 4.69 mmol) were added. The mixture was degassed with argon for 10 minutes and heated at 120° C. in a microwave reactor for 5 hours. The reaction mixture was quenched into 100 mL of water. Solids was collected by filtration and further washed with water (2×20 mL) and MeOH (2×5 mL), then dried under vacuum overnight. The crude solid product was purified by flash chromatography (silica gel, 0-10% methanol/DCM) to give Example 1 (1.2 g, 63% yield) as an off-white solid. $^1$H NMR (400 MHz, CHLOROFORM-d) δ 8.24 (s, 2H), 8.03-8.07 (m, 1H), 7.83-7.91 (m, 1H), 7.55-7.66 (m, 1H), 6.01 (s, 1H), 4.62-4.76 (m, 1H), 4.45-4.59 (m, 1H), 3.95-4.05 (m, 2H), 3.84-3.94 (m, 2H), 3.64-3.79 (m, 2H), 2.91 (d, J=2.20 Hz, 1H), 2.58-2.76 (m, 1H), 2.48 (s, 3H), 2.17-2.33 (m, 1H), 1.85-2.13 (m, 4H); MS (ESI) 531 (M+H).

Example 2

5-chloro-5'-(3-hydroxy-2-oxopyrrolidin-1-yl)-6'-methyl-4-((1-(5-propylpyrimidin-2-yl)piperidin-4-yl)oxy)-2H-[1,2'-bipyridin]-2-one

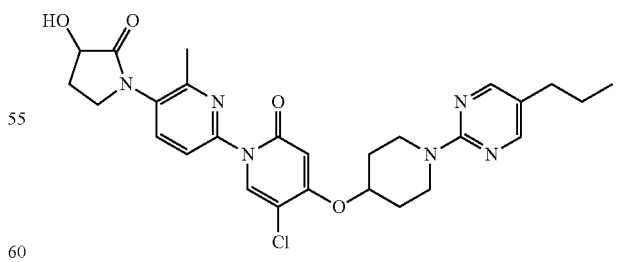

Following the same procedures as described in Example 1, Example 2 was prepared in 54% yield as a white solid by substituting Intermediate 2 with Intermediate 3. $^1$H NMR (400 MHz, CHLOROFORM-d) δ 8.09-8.22 (m, 2H), 7.99-8.09 (m, 1H), 7.76-7.92 (m, 1H), 7.52-7.67 (m, 1H), 5.86-6.15 (m, 1H), 4.60-4.76 (m, 1H), 4.42-4.60 (m, 1H), 3.98-

4.18 (m, 2H), 3.77-3.88 (m, 2H), 3.64-3.76 (m, 2H), 2.77-2.86 (m, 1H), 2.60-2.73 (m, 1H), 2.48 (s, 3H), 2.36-2.44 (m, 2H), 2.18-2.31 (m, 1H), 2.00-2.12 (m, 2H), 1.83-1.99 (m, 2H), 1.56-1.64 (m, 2H), 0.86-1.05 (m, 3H); MS (ESI) 539 (M+H).

Example 3

(S)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one

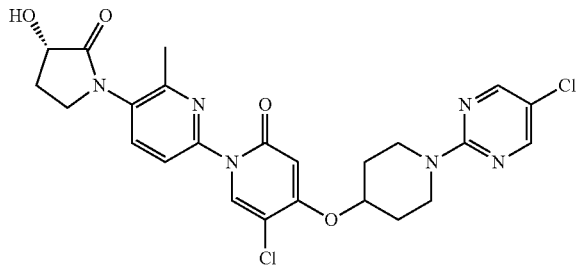 [SMILES: Cc1nc(-n2cc(Cl)c(OC3CCN(c4ncc(Cl)cn4)CC3)cc2=O)ccc1N1CC[C@H](O)C1=O]

Example 1 (40 mg) was subjected to a chiral separation by OD column with 50% methanol/ethanol 1:1 and 50% Heptanes. 18 mg (45%) of first eluting peak was obtained as Example 3. ¹H NMR (400 MHz, CHLOROFORM-d) δ 8.24 (s, 2H), 7.99-8.11 (m, 1H), 7.82-7.94 (m, 1H), 7.53-7.68 (m, 1H), 6.01 (s, 1H), 4.63-4.75 (m, 1H), 4.47-4.59 (m, 1H), 3.95-4.07 (m, 2H), 3.82-3.95 (m, 2H), 3.62-3.80 (m, 2H), 2.84-2.98 (m, 1H), 2.58-2.77 (m, 1H), 2.48 (s, 3H), 2.14-2.36 (m, 1H), 1.76-2.12 (m, 4H); MS (ESI) 531 (M+H).

Example 4

(R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one

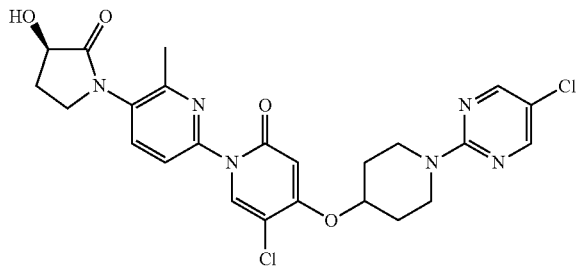 [SMILES: Cc1nc(-n2cc(Cl)c(OC3CCN(c4ncc(Cl)cn4)CC3)cc2=O)ccc1N1CC[C@@H](O)C1=O]

Example 1 (40 mg) was subjected to a chiral separation by OD column with 50% methanol/ethanol 1:1 and 50% Heptanes. 20 mg (50%) of second eluting peak was obtained as Example 4. ¹H NMR (400 MHz, CHLOROFORM-d) δ 8.24 (s, 2H), 8.00-8.10 (m, 1H), 7.79-7.93 (m, 1H), 7.51-7.72 (m, 1H), 5.95-6.07 (m, 1H), 4.61-4.75 (m, 1H), 4.44-4.58 (m, 1H), 3.95-4.07 (m, 2H), 3.82-3.95 (m, 2H), 3.61-3.80 (m, 2H), 2.79 (s, 1H), 2.58-2.72 (m, 1H), 2.48 (s, 3H), 2.15-2.33 (m, 1H), 1.85-2.12 (m, 4H); MS (ESI) 531 (M+H).

Alternatively, Example 4 was prepared as follows:

Step A: (R)-1-(6-bromo-2-methylpyridin-3-yl)-3-hydroxypyrrolidin-2-one

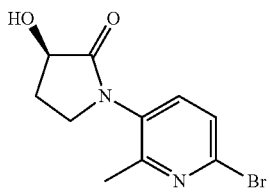

To a jacketed 5.0 liter glass reactor was added 2.150 liter of acetonitrile and 250 mL of water (10%, 27.78 moles, ~87 molar equivalent to acetate). The temperature was set to 25° C. Then, to the same reactor was added 1-(6-bromo-2-methylpyridin-3-yl)-2-oxopyrrolidin-3-yl acetate (50 g, 0.160 moles, 20 g/L), followed by 100 mL of acetonitrile The reaction mixture was stirred for 10 min at 90 rpm until complete dissolution. To the reaction mixture added 12.5 g of Novozym 435 (Enzyme to substrate 1:4) with continuous stirring under same reaction conditions. The temperature of the reaction was maintained at 25° C. during the course of the reaction. The reaction was stopped after 28 h, and the Novozym 435 was filtered. The reaction mixture was concentrated to dryness 30° C. to yield a viscous brownish liquid. The reaction mixture was taken out in 75 ml dichloromethane and stirred it at room temperature for 1 h. To the reaction mixture was added 100 g of silica gel, and slurry was then allowed to dry under pressure. A Column was packed with ~400 g of silica gel in heptanes and slurry was loaded into column with heptane. The column was run using 50% ethyl acetate-heptane until all the undesired chiral acetate was recovered. After the removal of acetate, the column was eluted with pure ethyl acetate and the (R)-1-(6-bromo-2-methylpyridin-3-yl)-3-hydroxypyrrolidin-2-one containing fractions were combined. The mixture was concentrated down to 50 mL under pressure at 20° C., stirred for 30 min, filtered, and washed with heptane. 16.042 g of (R)-1-(6-bromo-2-methylpyridin-3-yl)-3-hydroxypyrrolidin-2-one was obtained, as off-white solid, AP 99.4, ee 99.9% in 37% yield.

Step B: Example 4

To a nitrogen flushed vessel was added K₃PO₄ (625 g, 2.94 mol, 1.25 equiv), Intermediate 2 (800 g, 2.34 mol, 1.0 equiv), (R)-1-(6-bromo-2-methylpyridin-3-yl)-3-hydroxypyrrolidin-2-one (735 g, 2.71 mol, 1.15 equiv) and CuI (45.6 g, 0.239 mol, 0.1 equiv). The vessel was then evacuated and backfilled with nitrogen (3×). Then, DMF (3.9 L) and dimethylethylene diamine (100 mL, 0.934 mol, 0.4 equiv) was added under nitrogen and the vessel was again evacuated and backfilled with nitrogen (2×), with slow agitation. The vessel was heated to 66° C. (jacket temperature 70° C.). The contents were agitated at this temperature for 3-5 h. After the reaction was judged to be complete by HPLC the contents were cooled to 30° C. Once at this temperature DMF (1.6 L) was added to the reaction mixture. Holding the reaction stream at 30° C., 3.5 L was drained and added to a larger vessel preheated to hold an internal temperature of 30-35° C. (jacket 40° C.). Then, DCM (13.6 L) was added to the mixture and agitated. Once a fluid mixture was observed 26% w/w aqueous NH₄Cl (2.8 L) was added and the contents were agitated for 15-25 min. Agitation was stopped and the layers separated. The organic phase was drained and washed again with 26% w/w aqueous NH₄Cl (2.8 L) and agitated for 15-25 min. Agitation was stopped and the organic layer was transferred to a carboy (Batch 1). The remaining reaction stream (~3.25-3.5 L) was added to the larger vessel and was subjected to above work-up procedure. The second organic layer was transferred and stored in a carboy (Batch 2). Both batches were then subjected to carbon treatment, separately. Batch 1 was added to the larger vessel and the vessel was heated to 35° C. (jacket 42° C.). Once a homogenous solution was observed the stream was passed through a CUNO 4 cell, 8" housing (Darco G60) directly into a carboy. Batch 2 was then subjected to the same carbon treatment procedure. Then Batches 1 and 2 were polish filtered (1-10 μm) back into a clean vessel and processed according to Method 2, Example 7a set forth below.

Example 5

5'-(3-hydroxy-2-oxopyrrolidin-1-yl)-6'-methyl-4-((1-(5-propylpyrimidin-2-yl)piperidin-4-yl)oxy)-2H-[1,2'-bipyridin]-2-one

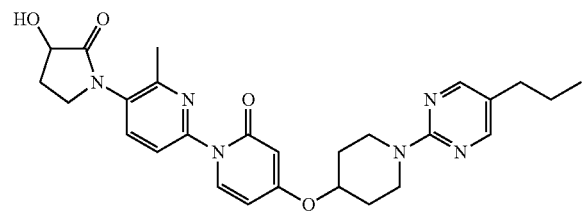 [SMILES: CCCc1cnc(N2CCC(Oc3ccn(-c4ccc(N5CCC(O)C5=O)c(C)n4)c(=O)c3)CC2)nc1]

A 25 mL round bottom flask was charged with 4-(1-(5-propylpyrimidin-2-yl)piperidin-4-yloxy)pyridin-2(1H)-one (116 mg, 0.369 mmol) (prepared according to the procedure described in patent application WO-2009/012275), Intermediate 4 (120 mg, 0.443 mmol), quinolin-8-ol (21.4 mg, 0.148 mmol), potassium carbonate (66.3 mg, 0.480 mmol), copper (I) iodide (28.1 mg, 0.148 mmol) and DMSO (3 mL). The mixture was heated under Ar to 140° C. for 5 hours and then allowed to cool to room temperature overnight. The resulting mixture was diluted with EtOAc (100 mL) and washed with H₂O (100 mL). The organic layer was concentrated in vacuo to a brown oil, which was purified by flash chromatography (SiO₂, 0 to 70% Acetone in CH₂Cl₂) to give example 5 (73.2 mg, 39% yield) as an off-white solid. ¹H NMR (400 MHz, DMSO-d6) δ 8.22 (s, 2H), 7.82 (dd, J=8.1, 5.5 Hz, 2H), 7.64 (d, J=8.4 Hz, 1H), 6.09 (dd, J=7.8, 2.6 Hz, 1H), 6.02 (d, J=2.5 Hz, 1H), 5.75 (d, J=5.7 Hz, 1H), 4.69-4.84 (m, 1H), 4.28-4.38 (m, 1H), 4.11-4.26 (m, 2H), 3.57-3.74 (m, 2H), 3.40-3.54 (m, 2H), 2.40-2.47 (m, 1H), 2.31-2.40 (m, 5H), 1.91-2.07 (m, 3H), 1.45-1.65 (m, 4H), 0.87 (t, J=7.3 Hz, 3H). MS (ESI) 505 (M+H).

Example 6

Preparation of 4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one

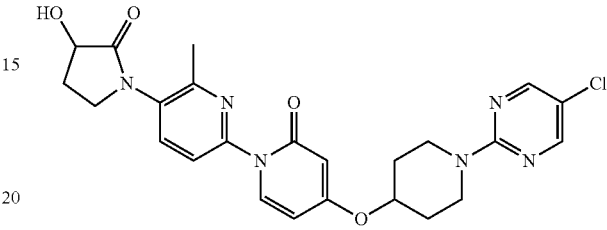

Example 6 was prepared according to procedures described in Example 5, substituting 4-(1-(5-propylpyrimidin-2-yl)piperidin-4-yloxy)pyridin-2(1H)-one with Intermediate 5. The solid obtained after flash chromatography was slurried with MeOH while heated to reflux, after cooling to room temperature the MeOH was decanted and the solid was dried in vacuo to yield example 6 in 68% yield as a white solid. ¹H NMR (400 MHz, DMSO-d6) δ 8.43 (s, 1H), 7.84 (dd, J=6.78, 8.03 Hz, 1H), 7.65 (d, J=8.28 Hz, 1H), 6.12 (dd, J=2.51, 7.78 Hz, 1H), 6.04 (d, J=2.76 Hz, 1H), 4.75-4.84 (m, 1H), 4.30-4.38 (m, 1H), 4.13-4.24 (m, 2H), 3.61-3.73 (m, 2H), 3.55 (ddd, J=3.39, 9.35, 13.11 Hz, 2H), 2.43-2.49 (m, 1H), 2.37 (s, 3H), 1.93-2.10 (m, 3H), 1.58-1.71 (m, 2H). MS (ESI) 497 (M+H).

Example 7

Crystal Forms of (R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one Various crystal forms of (R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one, free base were prepared and characterized as described below.

Procedures for Characterizing the Forms

Single Crystal Data

Data were collected on a Bruker-Nonius (BRUKER AXS, Inc., 5465 East Cheryl Parkway Madison, Wis. 53711 USA) CAD4 serial diffractometer. Unit cell parameters were obtained through least-squares analysis of the experimental diffractometer settings of 25 high-angle reflections. Intensities were measured using Cu Kα radiation (λ=1.5418 Å) at a constant temperature with the θ-2θ variable scan technique and were corrected only for Lorentz-polarization factors. Background counts were collected at the extremes of the scan for half of the time of the scan. Alternately, single crystal data were collected on a Bruker-Nonius Kappa CCD 2000 system using Cu Kα radiation (λ=1.5418 Å). Indexing and processing of the measured intensity data were carried out with the HKL2000 software package (Otwinowski, Z. et al. in Macromolecular Crystallography, Vol. 276, pp. 307-326, Carter, W. C., Jr. et al., eds., Academic, NY (1997)) in the Collect program suite. (Collect Data collection and processing user interface: Collect: Data collection software, R. Hooft, Nonius B. V., 1998.) Alternately, single crystal data were collected on a Bruker-AXS APEX2 CCD system using Cu Kα radiation (λ=1.5418 Å). Indexing and processing of the measured intensity data were carried out with the APEX2 software package/program suite (APEX2 Data collection and processing user interface: APEX2 User Manual, v1.27; BRUKER AXS, Inc., 5465 East Cheryl Parkway Madison, Wis. 53711 USA).

When indicated, crystals were cooled in the cold stream of an Oxford cryo system (Oxford Cryosystems Cryostream cooler: Cosier, J. et al., J. Appl. Cryst., 19:105 (1986)) during data collection.

The structures were solved by direct methods and refined on the basis of observed reflections using either the SDP software package with minor local modifications (SDP, Structure Determination Package, Enraf-Nonius, Bohemia N.Y. 11716. Scattering factors, including f' and f", in the SDP software were taken from the "International Tables for Crystallography", Vol. IV, Tables 2.2A and 2.3.1, Kynoch Press, Birmingham, England (1974)), or the crystallographic packages MAXUS (maXus solution and refinement software suite: Mackay, S. et al., maXus: a computer program for the solution and refinement of crystal structures from diffraction data) or SHELXTL[4]. The derived atomic parameters (coordinates and temperature factors) were refined through full matrix least-squares. The function minimized in the refinements was $\Sigma_w(|F_O|-|F_C|)^2 \cdot R$ is defined as $\Sigma||F_O|-|F_C||/\Sigma|F_O|$ while $R_w = [\Sigma_w(|F_O|-|F_C|)^2/\Sigma_w|F_O|^2]^{1/2}$ where w is an appropriate weighting function based on errors in the observed intensities. Difference maps were examined at all stages of refinement. Hydrogens were introduced in idealized positions with isotropic temperature factors, but no hydrogen parameters were varied.

X-Ray Powder Diffraction Data (PXRD)

PXRD data were obtained using a Bruker C2 GADDS. The radiation was Cu Kα (40 KV, 40 mA). The sample-detector distance was 15 cm. Powder samples were placed in sealed glass capillaries of 1 mm or less in diameter; the capillary was rotated during data collection. Data were approximately collected for 2≤2θ≤35° with a sample exposure time of at least 1000 seconds. The resulting two-dimensional diffraction arcs were integrated to create a traditional 1-dimensional PXRD pattern with a step size of 0.05 degrees 2θ in the approximate range of 2 to 35 degrees 2θ.

Differential Scanning Calorimetry (DSC)

DSC experiments were performed in a TA INSTRUMENTS® model Q2000, Q1000 or 2920. The sample (about 2-10 mg) was weighed in an aluminum pan and recorded accurately recorded to a hundredth of a milligram, and transferred to the DSC. The instrument was purged with nitrogen gas at 50 mL/min. Data were collected between room temperature and 300° C. at 10° C./min heating rate. The plot was made with the endothermic peaks pointing down.

Thermal Gravimetric Analysis (TGA)

TGA experiments were performed in a TA INSTRUMENTS® model Q5000, Q500 or 2950. The sample (about 4-30 mg) was placed in a platinum pan previously tared. The weight of the sample was measured accurately and recorded to a thousandth of a milligram by the instrument. The furnace was purged with nitrogen gas at 100 mL/min. Data were collected between room temperature and 300° C. at 10° C./min heating rate.

Solid State Nuclear Magnetic Resonance Spectroscopy (ss-NMR)

All solid-state C-13 NMR measurements were made with a Bruker AV III instrument operating at a proton frequency of 400.13 MHz. Solid samples were spun at 13 KHz in a 4 mm $ZrO_2$ rotor. The contact time was 3 milliseconds and was ramped from 50 to 100%. The relaxation delay was maintained at 20 seconds. Proton decoupling was applied using a TPPM sequence with a 4 microsecond pulse (62.5 KHz nominal band width). The spectral sweep width was 300 ppm centered at 100 ppm. 4096 data points were acquired and zero filled to 8192 prior to apodization with 20 Hz line broadening. Typically 2096 free induction decays were co-added. The spectra were referenced indirectly to TMS using 3-methylglutaric acid.

Hybrid PXRD Patterns

"Hybrid" simulated powder X-ray patterns were generated as described in the literature (Yin. S.; Scaringe, R. P.; DiMarco, J.; Galella, M. and Gougoutas, J. Z., *American Pharmaceutical Review*, 2003, 6, 2, 80). The room temperature cell parameters were obtained by performing a cell refinement using the CellRefine.xls program. Input to the program includes the 2-theta position of ca. 10 reflections, obtained from the experimental room temperature powder pattern; the corresponding Miller indices, hkl, were assigned based on the single-crystal data collected at low temperature. A new (hybrid) PXRD was calculated (by either of the software programs, Alex or LatticeView) by inserting the molecular structure determined at low temperature into the room temperature cell obtained in the first step of the procedure. The molecules are inserted in a manner that retains the size and shape of the molecule and the position of the molecules with respect to the cell origin, but, allows intermolecular distances to expand with the cell.

Preparation and Analysis of the Forms

Form Preparation, DSC and TGA Characterization

Example 7a, Form N-1: Method 1: 1 g of Example 4 was dissolved in 10 mL of NMP in a scintillation vial with magnetic stirring at 50° C. Upon dissolution, EtOH was added dropwise until the solution became cloudy (approx 10 mL), indicating the formation of a precipitate. The vial was removed from the heating block and then cooled to room temperature. Once at the prescribed temperature, additional EtOH was added until total volume of EtOH was 20 mL. The resulting slurry was aged overnight and then isolated on a Buchner funnel and washed 2× with 5 mL EtOH. The resulting samples were dried in vacuum oven at 50° C. overnight to provide Example 7a. Method 2: Polish filtered (1-10 µm) rich organic (~5:1 DCM: DMF) was added to a vessel. The contents of the vessel were heated to 35-38° C. (jacket 45-50° C.) under dynamic nitrogen to obtain a homogenous solution. The DCM was removed by reduced pressure (600-20 mbar) distillation, holding the pot temperature between 25-42° C., not exceeding 45° C. An off-white slurry was observed with the loss of ~5 vol of DCM. The distillation was continued until <10% DCM remained. The resulting slurry was cooled to 25° C. and polished filtered SDA 3A ethanol was added slowly (1-1.5 h addition) and the slurry was agitated for 12-24 h at 10-25° C. An off-white solid was isolated on a Nutsche filter, washing the filter cake with ethanol (1-2 L). The off-white solid was dried under reduced pressure at 40° C. for 48 h to afford Example 7a (930-975 g, 75-79%). Form N-1 free base was characterized by a PXRD pattern which matches the simulated pattern generated from the single crystal structure data. Form N-1 was characterized by a DSC thermogram having an endothermic event typically ca. 253° C., at higher temperatures other events may ensue. Form N-1 was characterized by a TGA curve having negligible weight loss at up to ca. 150° C. and in agreement with the single-crystal structure.

Example 7b, Form N-2: 1 g of Example 4 was dissolved in 10 mL of NMP in a scintillation vial with magnetic stirring at 50° C. Upon dissolution, 5 mL EtOH was added dropwise and a few mg of seeds of N-2 form were added; if the seeds did not dissolve, more seeds were added until ~100 mg of seeds (10% seed load) were added. The vial was removed from the heating block and cooled to room temperature. Precipitation was noticed and additional EtOH was added until the total volume of EtOH was 20 mL. The resulting slurry was aged overnight and then isolated on a Buchner funnel and washed 2× with 5 mL EtOH. The resulting samples were dried in vacuum oven at 50° C. overnight to provide Example 7b. Form N-2 free base was characterized by a PXRD pattern which matches the simulated pattern generated from the single crystal structure data. Form N-2 was characterized by a DSC thermogram having an endothermic event typically ca. 290° C. Form N-2 was characterized by a TGA curve having negligible weight loss at up to ca. 200° C. and in agreement with the single-crystal structure. The N-1 and N-2 forms were enantiotropically related with the N-1 form being more stable at room temperature and a transition temperature in the 50-60° C. range.

Example 7c, Form H2-3: 500 mg of Example 4 was dissolved in 16 mL of 90:10 THF:H$_2$O at 40° C. with magnetic stirring. Water, 25 mL, was added slowly, and precipitation occurred. The sample was removed from the heating block and cooled to room temperature. The resulting solid was isolated on Buchner funnel at dried under vacuum at room temperature to provide Example 7c. Form H2-3 free base was characterized by a PXRD pattern which matches the simulated pattern generated from the single crystal structure data. Form H2-3 was characterized by a DSC thermogram having an endothermic event typically in the range ca. 25-125° C., at higher temperatures other events may ensue. Form H2-3 was characterized by a TGA curve having a 6.4% weight loss at up to ca. 125° C. but a lower weight loss is often observed. This is in agreement with the less than ideal occupancy factors associated with the water molecules in the single crystal structure.

TABLE 2

Fractional Atomic Coordinates for Example 7a, Form N-1, at T = 25° C.

| Atom | x | y | z | Atom | x | y | z |
|---|---|---|---|---|---|---|---|
| C11 | 0.1710 | 0.9584 | 0.6435 | C33 | 0.6477 | 0.4470 | 0.2808 |
| C12 | 0.1819 | 0.1828 | 0.4216 | C48 | 0.1950 | −0.1926 | −0.0205 |
| N6 | 0.7516 | 1.2393 | 0.9395 | C40 | 0.1565 | 0.0065 | 0.1747 |
| N4 | 0.5672 | 0.9121 | 0.7909 | C31 | 0.4661 | 0.5088 | 0.3304 |
| N5 | 0.4649 | 1.0594 | 0.8664 | C44 | 0.6541 | −0.2130 | 0.0588 |
| N3 | 0.3435 | 0.3202 | 0.6826 | C29 | 0.8291 | 0.6251 | 0.2674 |
| N2 | 0.1028 | 0.3113 | 0.6070 | C47 | 0.2152 | −0.3190 | −0.0412 |
| N1 | 0.4732 | 0.2605 | 0.5687 | C32 | 0.8498 | 0.4816 | 0.2858 |
| O2 | 0.7693 | 0.7404 | 0.8589 | C30 | 0.4567 | 0.6511 | 0.3107 |
| O1 | 0.3241 | 0.6925 | 0.6947 | C25 | 0.7654 | 0.7696 | 0.5023 |
| O3 | 0.7226 | 1.4048 | 0.8366 | C27 | 0.9280 | 0.7237 | 0.4534 |
| O4 | 0.9464 | 1.4996 | 0.9270 | C26 | 0.5681 | 0.7720 | 0.4902 |
| C15 | 0.6264 | 0.9943 | 0.8289 | H4 | 0.9048 | 1.5650 | 0.8961 |
| C18 | 0.7125 | 1.1513 | 0.9028 | H12 | 0.6092 | 0.6183 | 0.7882 |
| C12 | 0.5608 | 0.7055 | 0.7767 | H17 | 1.0132 | 1.0915 | 0.8622 |
| C19 | 0.5081 | 1.1379 | 0.9030 | H13 | 0.3734 | 1.0513 | 0.7289 |
| C17 | 0.8758 | 1.0827 | 0.8634 | H22 | 0.6500 | 1.4934 | 0.9684 |
| C13 | 0.4218 | 0.9640 | 0.7405 | H9 | 0.3819 | 0.5278 | 0.7722 |
| C21 | 0.7488 | 1.3612 | 0.9032 | H3 | 0.5450 | 0.1940 | 0.4770 |
| C10 | 0.4154 | 0.7561 | 0.7274 | H16 | 0.9388 | 0.9528 | 0.7993 |
| C14 | 0.6408 | 0.7821 | 0.8110 | H8A | 0.6658 | 0.5098 | 0.6776 |
| C4 | 0.3059 | 0.2981 | 0.6162 | H8B | 0.5168 | 0.5280 | 0.6161 |
| C11 | 0.3483 | 0.8910 | 0.7077 | H2 | −0.0645 | 0.2811 | 0.5388 |
| C22 | 0.7794 | 1.4337 | 0.9576 | H7A | 0.0366 | 0.5550 | 0.7484 |
| C9 | 0.3535 | 0.5550 | 0.7190 | H7B | 0.1100 | 0.5561 | 0.6620 |
| C3 | 0.4331 | 0.2253 | 0.5099 | H5A | 0.1938 | 0.3433 | 0.7841 |
| C16 | 0.8322 | 1.0012 | 0.8258 | H5B | 0.0409 | 0.3565 | 0.7251 |
| C8 | 0.5351 | 0.4926 | 0.6694 | H6A | 0.6536 | 0.3104 | 0.6537 |
| C2 | 0.0726 | 0.2762 | 0.5468 | H6B | 0.5808 | 0.3113 | 0.7397 |
| C7 | 0.1475 | 0.5202 | 0.7131 | H24A | 0.8794 | 1.1397 | 1.0360 |
| C5 | 0.1700 | 0.3778 | 0.7314 | H24B | 0.6391 | 1.1986 | 1.0522 |
| C6 | 0.5451 | 0.3481 | 0.6884 | H20A | 0.1997 | 1.2164 | 0.9226 |
| C24 | 0.7706 | 1.2130 | 1.0214 | H20B | 0.3485 | 1.2937 | 0.9405 |
| C20 | 0.3244 | 1.2101 | 0.9445 | H20C | 0.3074 | 1.1665 | 0.9972 |
| C1 | 0.2319 | 0.2333 | 0.4960 | H23A | 0.7472 | 1.3593 | 1.0737 |
| C23 | 0.8284 | 1.3328 | 1.0294 | H23B | 0.9762 | 1.3183 | 1.0345 |
| C13 | 0.8258 | 0.0422 | 0.3570 | H8 | 0.2671 | −0.5854 | 0.0695 |
| C14 | 0.8181 | 0.8173 | 0.5785 | H35 | 0.3918 | 0.3840 | 0.2123 |
| N12 | 0.2270 | −0.2293 | 0.0595 | H38 | 0.6164 | −0.0507 | 0.2736 |
| N10 | 0.4274 | 0.0892 | 0.2108 | H41 | −0.0304 | −0.0775 | 0.1378 |
| N9 | 0.6554 | 0.6792 | 0.3176 | H46 | 0.0324 | −0.4225 | 0.0439 |
| N11 | 0.5215 | −0.0596 | 0.1366 | H33 | 0.6186 | 0.4745 | 0.2278 |
| N7 | 0.5248 | 0.7411 | 0.4302 | H48A | 0.3009 | −0.1461 | −0.0511 |
| N8 | 0.8935 | 0.6899 | 0.3928 | H48B | 0.0573 | −0.1406 | −0.0275 |
| O5 | 0.6781 | 0.3092 | 0.3044 | H40 | 0.0518 | 0.0566 | 0.2005 |
| O6 | 0.2234 | 0.2633 | 0.1441 | H31A | 0.3356 | 0.4912 | 0.3222 |
| O7 | 0.2670 | −0.4051 | 0.1567 | H31B | 0.4848 | 0.4738 | 0.3836 |

TABLE 1

Unit Cell Parameters

| Example | Form | T (° C.) | a(Å) | b(Å) | c(Å) | α° | β° | γ° | Z' |
|---|---|---|---|---|---|---|---|---|---|
| 7a | N-1 | 25 | 6.6000(3) | 11.1360(4) | 18.3761(7) | 74.624(2) | 79.720(2) | 76.844(2) | 2 |
| 7b | N-2 | 25 | 11.131(2) | 11.1918(9) | 20.800(3) | 90 | 101.623(4) | 90 | 2 |
| 7c | H2-3 | −70 | 4.4255(2) | 12.9992(4) | 44.459(2) | 90 | 90 | 90 | 1 |
| 7c | H2-3 | RT | 4.4689 | 12.9385 | 44.6887 | 90 | 90 | 90 | 1 |

| Example | Form | Vm | sg | R | dcalc |
|---|---|---|---|---|---|
| 7a | N-1 | 629 | P1 | .035 | 1.403 |
| 7b | N-2 | 635 | P2$_1$ | .056 | 1.391 |
| 7c | H2-3 | 639 | P2$_1$2$_1$2$_1$ | .044 | 1.474 |
| 7c | H2-3 (RT) | 646 | P2$_1$2$_1$2$_1$ | | 1.458 |

The variables used in Table 1 above are defined below:
Z' = number of drug molecules per asymmetric unit;
Vm = V(unit cell)/(Z drug molecules per cell);
sg = space group;
R = residual index (I > 3sigma(I)); and
dcalc = calculated crystal density.

TABLE 2-continued

Fractional Atomic Coordinates for Example 7a, Form N-1, at T = 25° C.

| Atom | x | y | z | Atom | x | y | z |
|---|---|---|---|---|---|---|---|
| O8 | 0.3091 | -0.5321 | 0.0331 | H44A | 0.7799 | -0.1817 | 0.0563 |
| C35 | 0.4379 | 0.2965 | 0.2238 | H44B | 0.6256 | -0.2061 | 0.0084 |
| C39 | 0.3655 | 0.0094 | 0.1727 | H44C | 0.6720 | -0.3003 | 0.0863 |
| C43 | 0.4740 | -0.1364 | 0.0993 | H29A | 0.9584 | 0.6462 | 0.2740 |
| C42 | 0.2694 | -0.1448 | 0.0988 | H29B | 0.8044 | 0.6606 | 0.2148 |
| C36 | 0.6492 | 0.1099 | 0.2921 | H47A | 0.1112 | -0.3134 | -0.0737 |
| C38 | 0.5717 | 0.0368 | 0.2610 | H47B | 0.3536 | -0.3434 | -0.0675 |
| C41 | 0.1086 | -0.0723 | 0.1375 | H32A | 0.9600 | 0.4466 | 0.2503 |
| C37 | 0.3505 | 0.2212 | 0.1897 | H32B | 0.8884 | 0.4454 | 0.3367 |
| C28 | 0.6933 | 0.7027 | 0.3824 | H30A | 0.4235 | 0.6870 | 0.2591 |
| C45 | 0.2301 | -0.3534 | 0.0918 | H30B | 0.3465 | 0.6896 | 0.3448 |
| C46 | 0.1799 | -0.4137 | 0.0333 | H27 | 1.0652 | 0.7157 | 0.4623 |
| C34 | 0.5836 | 0.2463 | 0.2716 | H26 | 0.4573 | 0.7961 | 0.5256 |

TABLE 3

Fractional Atomic Coordinates for Example 7b, Form N-2, at T = 25° C.

| Atom | x | y | Z | Atom | x | y | z |
|---|---|---|---|---|---|---|---|
| C11 | 0.6560 | 1.0350 | 0.1194 | C30 | 0.2222 | 0.9685 | 0.2318 |
| N5 | 0.6016 | 1.2835 | 0.3433 | C32 | 0.2346 | 0.8380 | 0.2159 |
| C15 | 0.5085 | 1.2202 | 0.3129 | C47 | -0.0493 | -0.2515 | 0.4458 |
| O1 | 0.6378 | 0.8159 | 0.1893 | 08 | -0.1026 | -0.3544 | 0.4172 |
| O3 | 0.5052 | 1.6579 | 0.3424 | C45 | -0.1258 | -0.0560 | 0.4604 |
| C12 | 0.7710 | 0.2114 | -0.0389 | C29 | 0.0112 | 0.9698 | 0.1740 |
| C19 | 0.5771 | 1.3823 | 0.3751 | C41 | -0.1265 | 0.1135 | 0.3414 |
| O2 | 0.5006 | 1.0035 | 0.3666 | C27 | 0.3140 | 1.1595 | 0.0833 |
| C4 | 0.6682 | 0.3930 | 0.1286 | C31 | 0.0162 | 0.8403 | 0.1557 |
| C13 | 0.5353 | 1.0047 | 0.3133 | C44 | 0.2001 | 0.0350 | 0.4185 |
| N4 | 0.5411 | 1.1132 | 0.2816 | C25 | 0.2341 | 1.1816 | 0.0265 |
| N6 | 0.4315 | 1.5240 | 0.4062 | C46 | -0.1432 | -0.1821 | 0.4753 |
| C18 | 0.4579 | 1.4198 | 0.3742 | H28 | 0.5846 | 1.1956 | 0.2044 |
| C11 | 0.6100 | 1.0224 | 0.1936 | H38A | 0.8023 | 0.6691 | 0.2526 |
| C14 | 0.5795 | 1.1212 | 0.2235 | H38B | 0.7749 | 0.6408 | 0.1770 |
| N3 | 0.6358 | 0.4459 | 0.1822 | H41 | 0.3280 | 1.1958 | 0.2902 |
| C10 | 0.6052 | 0.9079 | 0.2238 | H43 | 0.5671 | 0.8281 | 0.3009 |
| N2 | 0.5776 | 0.3751 | 0.0756 | H50A | 0.5424 | 0.6427 | 0.1175 |
| C8 | 0.7440 | 0.6323 | 0.2172 | H50B | 0.4462 | 0.6722 | 0.1612 |
| C16 | 0.3902 | 1.2458 | 0.3113 | H51 | 0.5971 | 0.6943 | 0.2524 |
| C24 | 0.4533 | 1.6350 | 0.3858 | H52A | 0.7581 | 1.4045 | 0.4124 |
| C12 | 0.5695 | 0.9023 | 0.2812 | H52B | 0.6748 | 1.4552 | 0.4585 |
| C7 | 0.5245 | 0.6342 | 0.1611 | H52C | 0.6887 | 1.5259 | 0.3953 |
| C9 | 0.6218 | 0.6932 | 0.2098 | H57A | 0.2989 | 1.6794 | 0.4966 |
| C20 | 0.6842 | 1.4478 | 0.4138 | H57B | 0.4405 | 1.6546 | 0.5201 |
| N1 | 0.7846 | 0.3634 | 0.1336 | H59 | 0.5546 | 0.3127 | -0.0130 |
| C22 | 0.3722 | 1.6511 | 0.4829 | H60A | 0.3818 | 1.4650 | 0.4897 |
| C1 | 0.7291 | 0.2857 | 0.0270 | H60B | 0.2688 | 1.5086 | 0.4360 |
| C2 | 0.6127 | 0.3237 | 0.0255 | H61 | 0.4738 | 1.8680 | 0.4190 |
| C21 | 0.3541 | 1.5239 | 0.4558 | H64 | 0.2832 | 1.3702 | 0.3413 |
| O4 | 0.4749 | 1.8198 | 0.4488 | H66A | 0.4908 | 0.4882 | 0.2196 |
| C17 | 0.3642 | 1.3488 | 0.3422 | H66B | 0.4576 | 0.4576 | 0.1442 |
| C5 | 0.5168 | 0.4975 | 0.1781 | H67 | 0.3212 | 1.7554 | 0.4003 |
| C23 | 0.3985 | 1.7250 | 0.4262 | H68 | 0.8934 | 0.2851 | 0.0842 |
| C3 | 0.8126 | 0.3087 | 0.0822 | H69A | 0.8069 | 0.4583 | 0.2337 |
| C6 | 0.7295 | 0.4992 | 0.2321 | H69B | 0.7073 | 0.4908 | 0.2747 |
| C13 | 0.1418 | 0.4371 | 0.1143 | H12 | 0.0723 | 0.6424 | 0.3003 |
| C14 | 0.2766 | 1.2569 | -0.0374 | H34 | 0.0828 | 0.7755 | 0.2488 |
| C36 | 0.0718 | 0.5682 | 0.2801 | H39 | 0.0752 | 0.2759 | 0.2009 |
| O6 | 0.0181 | 0.4643 | 0.3693 | H44 | 0.0564 | 1.1682 | -0.0122 |
| C43 | 0.0888 | 0.0918 | 0.3782 | H46 | -0.1702 | 0.2593 | 0.2851 |
| C42 | -0.0302 | 0.0512 | 0.3756 | H48A | 0.1985 | 0.9758 | 0.2740 |
| O7 | 0.0461 | -0.1889 | 0.3568 | H48B | 0.3007 | 1.0079 | 0.2348 |
| C39 | 0.0144 | 0.2492 | 0.3122 | H49A | 0.2918 | 0.7996 | 0.2512 |
| O5 | 0.1236 | 0.6552 | 0.1845 | H49B | 0.2665 | 0.8304 | 0.1760 |
| N9 | 0.1298 | 1.0276 | 0.1811 | H53 | 0.0219 | -0.2714 | 0.4802 |
| C37 | 0.0418 | 0.4644 | 0.3141 | H55 | -0.0584 | -0.3841 | 0.3944 |
| N12 | -0.0519 | -0.0562 | 0.4102 | H56A | -0.2042 | -0.0175 | 0.4442 |
| N10 | 0.0426 | 0.3571 | 0.2804 | H56B | -0.0838 | -0.0139 | 0.4992 |
| C28 | 0.1655 | 1.0744 | 0.1279 | H62A | -0.0475 | 1.0109 | 0.1405 |
| C34 | 0.0994 | 0.5621 | 0.2196 | H62B | -0.0172 | 0.9761 | 0.2150 |
| C48 | -0.0126 | -0.1647 | 0.3984 | H63 | -0.2063 | 0.0874 | 0.3401 |
| C33 | 0.1103 | 0.7770 | 0.2069 | H65 | 0.3950 | 1.1837 | 0.0868 |

TABLE 3-continued

Fractional Atomic Coordinates for Example 7b, Form N-2, at T = 25° C.

| Atom | x | y | Z | Atom | x | y | z |
|---|---|---|---|---|---|---|---|
| N11 | 0.1086 | 0.1901 | 0.3455 | H70A | 0.0382 | 0.8332 | 0.1131 |
| C38 | 0.0742 | 0.3501 | 0.2208 | H70B | -0.0637 | 0.8038 | 0.1532 |
| N8 | 0.0797 | 1.0965 | 0.0748 | H71A | 0.2639 | 0.0936 | 0.4296 |
| C26 | 0.1151 | 1.1506 | 0.0252 | H71B | 0.2276 | -0.0284 | 0.3939 |
| C35 | 0.1041 | 0.4483 | 0.1899 | H71C | 0.1805 | 0.0031 | 0.4580 |
| C40 | -0.1056 | 0.2149 | 0.3088 | H74A | -0.2258 | -0.2077 | 0.4560 |
| N7 | 0.2836 | 1.1058 | 0.1341 | H74B | -0.1294 | -0.1945 | 0.5224 |

TABLE 4

Fractional Atomic Coordinates for Example 7c, Form H2-3, at T = -70 ° C.

| Atom | x | y | Z | Atom | x | y | z |
|---|---|---|---|---|---|---|---|
| C11 | -0.3484 | 1.1939 | 0.0264 | C22 | 0.8992 | -0.1621 | 0.2297 |
| C12 | 0.1163 | 0.3703 | 0.0614 | O1W | 0.9830 | -0.3847 | 0.1910 |
| N1 | 0.2346 | 0.9630 | 0.0208 | O2W | 1.1510 | -0.3122 | 0.1660 |
| N2 | 0.1885 | 1.0082 | 0.0728 | O3W | 0.6030 | -0.4051 | 0.1991 |
| N6 | 0.8425 | 0.0028 | 0.2107 | H4 | 0.7461 | -0.2927 | 0.2229 |
| N4 | 0.6010 | 0.3339 | 0.1350 | H9 | 0.7826 | 0.6500 | 0.0760 |
| N3 | 0.4955 | 0.8742 | 0.0575 | H16 | 0.4383 | 0.3086 | 0.1911 |
| N5 | 0.8228 | 0.1727 | 0.1441 | H12 | 0.7647 | 0.5719 | 0.1218 |
| O1 | 0.4065 | 0.5619 | 0.0748 | H7A | 0.5074 | 0.7171 | 0.1155 |
| O4 | 0.7169 | -0.2493 | 0.2361 | H7B | 0.2225 | 0.7370 | 0.0946 |
| O2 | 0.9071 | 0.4374 | 0.1628 | H5A | 0.4619 | 0.8949 | 0.1020 |
| O3 | 0.6299 | -0.1269 | 0.1824 | H5B | 0.7777 | 0.8486 | 0.0920 |
| C9 | 0.5634 | 0.6604 | 0.0727 | H2 | -0.0895 | 1.1226 | 0.0802 |
| C19 | 0.8844 | 0.0922 | 0.1622 | H14 | 0.3328 | 0.2517 | 0.1079 |
| C4 | 0.3025 | 0.9510 | 0.0501 | H6A | 0.8396 | 0.8043 | 0.0366 |
| C16 | 0.5513 | 0.2522 | 0.1841 | H6B | 0.5598 | 0.8255 | 0.0152 |
| C13 | 0.7424 | 0.4275 | 0.1404 | H3 | -0.0111 | 1.0469 | -0.0063 |
| C12 | 0.6754 | 0.5069 | 0.1193 | H8A | 0.6112 | 0.6492 | 0.0268 |
| C7 | 0.4438 | 0.7373 | 0.0952 | H8B | 0.2911 | 0.6928 | 0.0364 |
| C15 | 0.6597 | 0.2497 | 0.1554 | H20A | 0.9482 | -0.0476 | 0.1423 |
| C5 | 0.5592 | 0.8457 | 0.0885 | H20B | 1.2197 | -0.0155 | 0.1635 |
| C2 | -0.0055 | 1.0813 | 0.0650 | H20C | 1.1845 | 0.0361 | 0.1315 |
| C14 | 0.4159 | 0.3175 | 0.1109 | H24A | 0.8962 | 0.0723 | 0.2516 |
| C6 | 0.6185 | 0.8032 | 0.0355 | H24B | 1.2035 | 0.0257 | 0.2385 |
| C1 | -0.0893 | 1.0993 | 0.0357 | H17 | 0.5432 | 0.1695 | 0.2225 |
| C11 | 0.3502 | 0.3927 | 0.0916 | H23A | 1.0749 | -0.1068 | 0.2694 |
| C18 | 0.7744 | 0.0891 | 0.1914 | H23B | 0.7221 | -0.0846 | 0.2660 |
| C3 | 0.0408 | 1.0366 | 0.0140 | H22 | 1.1057 | -0.1849 | 0.2243 |
| C8 | 0.5081 | 0.6959 | 0.0407 | H11A | 0.9585 | -0.4427 | 0.1821 |
| C10 | 0.4870 | 0.4914 | 0.0958 | H11B | 0.8757 | -0.3384 | 0.1823 |
| C20 | 1.0762 | 0.0089 | 0.1487 | H22A | 1.0040 | -0.3284 | 0.1779 |
| C24 | 0.9852 | 0.0148 | 0.2404 | H22B | 1.2510 | -0.2621 | 0.1738 |
| C21 | 0.7681 | -0.0968 | 0.2041 | H33A | 0.6918 | -0.4516 | 0.1888 |
| C17 | 0.6123 | 0.1700 | 0.2025 | H33B | 0.4609 | -0.3775 | 0.1888 |
| C23 | 0.9150 | -0.0876 | 0.2552 | | | | |

Characteristic powder X-ray diffraction peak positions (degrees 2θ±0.1)@ RT for Examples 7a, b and c based on a high quality pattern collected with a diffractometer (CuKα) with a spinning capillary with 2θ calibrated with a NIST or other suitable standard.

TABLE 5a

| Exp 7a | Exp 7b | Exp 7c |
|---|---|---|
| 5.0 | 4.3 | 4.0 |
| 10.1 | 8.7 | 7.1 |
| 11.5 | 11.5 | 9.1 |
| 13.9 | 15.3 | 13.7 |
| 14.4 | 16.0 | 15.5 |
| 16.1 | 17.7 | 17.3 |
| 18.2 | 20.0 | 20.3 |
| 21.6 | 20.6 | 22.5 |
| 26.0 | | 23.3 |

The Carbon 13 SSNMR chemical shifts for Examples 7a and 7c are substantially as tabulated in Table 5b.

TABLE 5b

Carbon-13 SSNMR Chemical Shifts for Examples 7a and 7c

| N-1 | H2-3 |
|---|---|
| 21 | 23 |
| 23 | 31 |
| 26 | 33 |
| 28 | 42 |
| 31 | 49 |
| 32 | 71 |
| 43 | 78 |
| 45 | 99 |
| 48 | 111 |
| 69 | 122 |
| 71 | 135 |
| 81 | 137 |
| 100 | 151 |
| 109 | 158 |
| 114 | 165 |
| 121 | 165 |
| 123 | 177 |
| 124 | |
| 136 | |
| 139 | |
| 140 | |
| 152 | |
| 158 | |
| 160 | |
| 161 | |
| 165 | |
| 179 | |

Assay(s) for GPR119 G Protein-Coupled Receptor Activity

The in vitro modulation of recombinant human GPR119 was determined as follows.
Tet-Inducible cAMP Assay A human-mouse chimeric GPR119 expression construct encoding 3 copies of the FLAG epitope tag, the first 198 amino acids of human GPR119 and the C-terminal 137 amino acids of the mouse receptor was cloned into a tetracycline inducible vector pcDNA5/FRT/TO (Invitrogen #V6520-20), which includes a hygromycin-resistance marker. Tightly controlled receptor expression was achieved by stable integration of this construct into the genome of a specific host cell line, Flp-In-T-Rex-HEK293, expressing the tetracycline repressor (Invitrogen). Once a stable hygromycin-resistant cell line was generated, the cells were maintained at 37° C. in a humidified 5% $CO_2$ atmosphere in culture medium consisting of Dulbecco's modified Eagle's medium (DMEM; Invitrogen #11960) supplemented with 2 mM L-glutamine, 10% fetal bovine serum, 200 µg/ml hygromycin B, and 15 µg/ml blasticidin.

Forty-eight hours prior to the cAMP accumulation assay, cells stably expressing the chimeric human/mouse GPR119 construct were seeded at a density of $4 \times 10^3$ cells/well in 384 well poly-D-lysine coated solid white plates (BD #35-6661) and grown at 37° C. in a humidified 5% $CO_2$ atmosphere in culture medium supplemented with 1 µg/ml tetracycline to induce expression of the receptor. On the day of the assay, medium was removed and cells were incubated for 50 min. at 37° C. in a humidified 5% $CO_2$ atmosphere in 20 µl/well of assay buffer (phosphate-buffered saline with $Ca^{2+}$ and $Mg^{2+}$, 12 mM glucose, 0.1 mM isobutyl-methyl-xanthine, 0.1% fatty-acid free bovine serum albumin) with the desired concentration of compound added from a concentrated stock dissolved in dimethyl sulfoxide (DMSO) to give a final concentration of 1% DMSO in the assay. cAMP accumulation was measured using the CisBio homogeneous time resolved fluorescence (HTRF) assay kit (#62AM2PEC) following the manufacturer's protocol. Briefly, 10 µl each of the cAMP-HTRF fluorescence detection reagents were added to each well, and the samples were incubated for 40 min. at room temperature. Fluorescence was excited at 320 nm and measured at 665 and 620 nm using the Envision instrument (Perkin Elmer), the fluorescence ratio of 665/620 was calculated and converted to nanomolar concentrations of cAMP in each well by interpolation from a cAMP standard curve. The concentration-response curves and $EC_{50}$ values were calculated with a four parameter logistic curve fit equation utilizing Excel/XLfit software (Microsoft and IDBS). The $EC_{50}$ value was calculated as the concentration of agonist which increased the cAMP concentration to a value halfway between the baseline and the maximum.

Compounds of the present invention were tested in the Tet-inducible cAMP assay described immediately above and the results shown in Table 6 below were obtained.

TABLE 6

| Example | GPR119 $EC_{50}$ (nM) |
|---|---|
| 1 | 2 |
| 2 | 4 |
| 3 | 4 |
| 4 | 3 |
| 5 | 16 |
| 6 | 10 |

Mouse Oral Glucose Tolerance Test

Twenty four (24) male C57BL/6J mice (8-10 weeks old, average weight 28 g) were randomized into 4 groups (1 mouse/cage) of 6 mice per group based on fed plasma glucose and body weight. Prior to initiating the study, mice were fasted overnight and the next morning they were weighed and placed in the experimental lab. After 30 min in the environment, the mice were bled via tail tip at −60 min and immediately given their first oral administration of vehicle (40% PEG400, 10% Cremophor EL, 50% water) or compound solutions (5 ml/kg). At time 0 the mice were bled and given 50% glucose (2 g/kg) to initiate the oral glucose tolerance test (oGTT). The mice were bled 30, 60 and 120 min after the glucose load. Blood samples were drawn into potassium EDTA, placed on ice during the study and subsequently centrifuged for 10 min at 3000 rpm at 4° C. Plasma samples were diluted 11-fold for glucose analysis in the COBAS MIRA® System (Roche Diagnostics). Area under the curve was calculated from the plasma glucose time course data using the trapezoid rule with fasting plasma glucose as the baseline (GraphPad Prism Software). The statistical significance of the changes in the glucose AUCs resulting from the different treatments was determined by one-way ANOVA followed by Dunnett's test using the vehicle group as the control (JMP software, release 5.1.2).

Find below in Table 7 data for compared compounds (See WO 2009/012275 A1). The comparative data shows the unexpected significant reduction in plasma glucose at significantly lower doses of the compounds of the present invention.

TABLE 7

Comparative In vivo Data

| Compound | Minimally efficacious Dose (mg/kg) | Glucose Lowering (%) |
|---|---|---|
| Example 3 WO 2009/012275 A1 | 30 | −29% |
| Example 142 WO 2009/012275 A1 | 1 | −33% |
| Example 190 WO 2009/012275 A1 | 10 | −18% |
| Example 224 WO 2009/012275 A1 | 0.3 | −30% |
| Example 229 WO 2009/012275 A1 | 1 | −20% |
| Example 265 WO 2009/012275 A1 | 3 | −25% |
| Example 268 WO 2009/012275 A1 | 3 | −23% |
| Example 1 Present Invention | 0.03 | −36% |
| Example 2 Present Invention | 0.03 | −19% |
| Example 3 Present Invention | 0.03 | −26% |
| Example 4 Present Invention | 0.03 | −39% |
| Example 5 Present Invention | 0.1 | −21% |

Metabolic Stability in Liver Microsomes Test

Human liver microsomes were purchased from BD-Biosciences (Woburn, Mass.). The test compound was received as a 3.5 mM stock solution in 100 percent dimethyl sulfoxide ("DMSO", Sigma Aldritch). The compound solution was diluted to create a 50 µM acetonitrile ("ACN", Sigma Aldritch) solution containing 1.4% DMSO, which is then used as a 100-fold stock for incubation with microsomes. The test compound, β-nicotinamide adenine dinucleotide phosphate ("NADPH", AppliChem Inc.) and liver microsome solutions are combined for incubation in three steps:

1) 450 µl of liver microsome suspension, protein concentration of 1.1 mg/ml in 100 mM sodium (+)/phosphate ("NaP$_i$", pH 7.4, Sigma Aldritch) buffer, 5 mM magnesium chloride ("MgCl$_2$, Sigma Aldritch) buffer, is pre-warmed at 37° C.;

2) 5 µl of 50 µM test compound (98.6% ACN, 1.4% DMSO) is added to the same tube and pre-incubated at 37° C. for 5 minutes; and 3) The reaction is initiated by the addition of 50 µl of pre-warmed 10 mM NADPH solution in 100 mM NaP$_i$, pH 7.4.

Reaction components are mixed well and then 65 µl are immediately transferred into 130 µl quench/stop solution (zero-time point, T$_0$). The reactions are incubated at 37° C. for 5, 10, 15, 30 and 45 minutes and at each time-point a 65 µl aliquot is transferred into 130 µl of quench solution. ACN containing Internal Standard (100 ng/ml), is used as the quench solution to terminate metabolic reactions. The quenched mixtures are centrifuged at 1500 rpm (~500×g) in an Allegra X-12 centrifuge, SX4750 rotor (Beckman Coulter Inc., Fullerton, Calif.) for fifteen minutes to pellet denatured microsomes. A volume of 90 µl of supernatant extract, containing the mixture of parent compound and its metabolites, is then transferred to a separate 96-well plate for LC/MS-MS analysis to determine the percent of parent compound that is remaining in the mixture. Peak integration is performed on all samples using the Hepatic Clearance Calculator of QuickCalc by Gubbs, Inc. The percent remaining calculation is performed by comparing the LC-MS/MS peak areas from the samples at each time point to those from the T$_0$ samples for each compound. T$_{1/2}$ values are calculated from linear regression of the LN (% Remaining) over time, and the slope of that regression (Kel) is used to calculate T$_{1/2}$, using the following equation: T$_{1/2}$=−0.693/Kel.

Find below in Table 8 data for compared compounds (See WO 2009/012275 A1). Generally, the comparative data shows the unexpected improvement in metabolic stability of the compounds of the present invention.

TABLE 8

Additional comparative In vitro Data

| Compound | Human Liver Microsome Half-life (minutes) |
|---|---|
| Example 142 WO 2009/012275 A1 | 33 |
| Example 151 WO 2009/012275 A1 | 71 |
| Example 190 WO 2009/012275 A1 | 122 |
| Example 224 WO 2009/012275 A1 | 4 |
| Example 229 WO 2009/012275 A1 | 30 |
| Example 265 WO 2009/012275 A1 | 47 |
| Example 268 WO 2009/012275 A1 | 59 |
| Example 1 Present Invention | 94 |
| Example 2 Present Invention | 120 |
| Example 3 Present Invention | 78 |
| Example 4 Present Invention | 97 |
| Example 5 Present Invention | 76 |
| Example 6 Present Invention | 101 |

Aqueous Solubility Assay

Approximately 0.75 mg of accurately weighed test compound was added to 1 mL of a pH 6.5 phosphate buffer (50 mM Potassium Phosphate Buffer) to make solutions with a nominal targeted concentration of 1 mM. The vial was then rotated on an orbital shaker at room temperature for 18-24 h. After equilibration time had been met, the test solution was centrifuge filtered through a 0.45 um membrane (Millipore Ultrafree Centrifugal Filters, Durapore PVDF 0.45 um). The filtrate was then analyzed by an Agilent HP1100 HPLC/UV at multiple wavelengths using diode array detection (e.g. 210, 230, 254 and 280 nm) against a previously generated calibration curve to determine compound concentration.

FaSSIF Solubility Assay

Approximately 5-10 mg of accurately weighed test compound was transferred to a glass vial containing 4 mL of a FaSSIF buffer (PharesAG, prepared according to manufactures protocol). The vial was then rotated at 37° C. for 24 h. After equilibration time had been met, the test solution was centrifuge filtered through a 0.45 um PTFE membrane filter. The filtrate was then analyzed by HPLC/UV against a set of standard injections to determine compound concentration.

Find below in Table 9 data for compared compounds (See WO 2011/127106 A1). Generally, the comparative data shows the unexpected improvement in solubility, aqueous, FaSSIF and/or both, of the compounds of the present invention.

TABLE 9

Comparative Solubility Data

| Compound | Aqueous Solubility (µg/mL) | FaSSIF Solubility (µg/mL) |
|---|---|---|
| Example 5 WO 2011/127106 A1 | <0.4 | 0.3 |
| Example 1 Present Invention | 4 | |
| Example 2 Present Invention | 1 | |
| Example 3 Present Invention | 1 | |
| Example 4 Present Invention | 2 | 11 |
| Example 5 Present Invention | 3 | |
| Example 6 Present Invention | 7 | |

Compound Bioavailability Assays

Male Sprague-Dawley rats (270-350 g) were used in the pharmokinetic studies. Two (2) groups of animals (N=3 per group) were fasted overnight and one group received test compound as an IV infusion dose (1 mg/kg over 10 minutes) via a jugular vein in PEG-400/propylene glycol/ethanol (50:40:10) or Cremophor-EL/PEG400/water (10:40:50, v/v/v). The other group received test compound by oral gavage (2 or 5 mg/kg) as either nano-suspension in Pluronic F-108/polyvinylpyrrolidinone/water (1:2.5:96.5, v/v/v) or in Methocel A4M/Tween 80/water (0.5:0.1:99.4, v/v/v) as suspension (partical size: d50=0.960 µm; d90=4.4 µm) for oral dosing. Serial blood samples (0.3 mL) were collected into K3EDTA-containing tubes predose and at 0.17 (IV only) 0.25, 0.5, 1, 2, 4, 6, 8, 24, 48, and 72 hours post dose. Plasma samples, obtained by centrifugation at 4° C. (1500-2000×g), were stored at 20° C. until analysis by LC/MS/MS.

Data Analysis

Pharmacokinetic parameters were obtained by non-compartmental analysis of plasma concentration vs. time data (KINETICA™ software, Version 5.0, Thermo Fisher Scientific Corporation, Philadelphia, Pa.). The peak concentration (Cmax) and time for Cmax (Tmax) were recorded directly from experimental observations. The area under the curve from time zero to the last sampling time [AUC(0-T)] and the area under the curve from time zero to infinity [AUC(INF)] were calculated using a combination of linear and log trapezoidal summations. The total plasma clearance (CLTp), steady-state volume of distribution (Vss), apparent elimination half-life (T HALF), and mean residence time (MRT) were estimated after IV administration. Estimations of AUC and T-HALF were made using a minimum of 3 timepoints with quantifiable concentrations. The total blood clearance (CLTb) was calculated as the CLTp divided by the blood-to-plasma concentration ratio. The absolute oral bioavailability (F) in rats was estimated as the ratio of dose-normalized area under the curve from time zero to infinity [AUC(INF)] values following oral and IV doses. The absolute oral bioavailability (F) in dogs was estimated as the ratio of dose-normalized area under the curve from time zero to the last sampling time [AUC(0-T)] following oral and IV doses.

Find below in Table 10 data for compared compounds (See WO 2011/127106 A1). Generally, the comparative data shows the unexpected improvement in bioavailability of the compounds of the present invention.

TABLE 10

Comparative Bioavailability Data

| Compound | Rat Bioavailability |
|---|---|
| Example 5 WO 2011/127106 A1 | 33% at 5 mg/kg as a nanosuspension |
| Example 3 Present Invention | 120% at 5 mg/kg as a microsuspension |
| Example 4 Present Invention | 122% at 2 mg/kg as a microsuspension |

Compound Electrophysiology Assays

Recombinant ion channels (hERG, sodium [SCN5A], and L-type calcium [$Ca_v1.2$]) stably expressed in human embryonic kidney cells (HEK293) are used as test systems, and each system is tested using 2-3 replicates in the conventional patch clamp assay.

Ion channel membrane current recordings are made with a Multiclamp 700 series integrating patch-clamp amplifier (Axon Instruments, Foster City, Calif.) using the whole-cell variant of the patch-clamp technique.

Cells expressing hERG, sodium [SCN5A], or L-type calcium [$Ca_v1.2$] channels are placed in a plexiglass bath chamber, mounted on the stage of an inverted microscope, and perfused continuously with bath solution.

The hERG bath solution, which replaces the cell culture media during experiments, contains (in mM): 140 NaCl, 4 KCl, 1.8 $CaCl_2$, 1 $MgCl_2$, 10 glucose, 10 HEPES (pH 7.4, NaOH). Borosilicate glass pipettes have tip resistances of 2 to 4 MΩ when filled with an internal solution containing (in mM): 130 KCl, 1 $MgCl_2$, 1 $CaCl_2$, 5 ATP-$K_2$, 10 EGTA, 10 HEPES (pH 7.2, KOH).

Initially, a current-voltage relationship is generated in the control bath solution using the following voltage protocol. hERG currents are elicited by 2 second step depolarizations applied from a holding potential of −80 mV to test potentials ranging from −70 mV to +60 mV. The voltage steps are applied in 20 second intervals. Tail currents are elicited upon repolarization to −65 mV for 3 seconds. While still perfusing with control bath solution, the voltage protocol is switched to one where repetitive test pulses (0.05 Hz) are applied from a holding potential of −80 mV to +20 mV for 2 seconds. Tail currents are elicited following the test pulses by stepping the voltage to −65 mV for 3 seconds. After recording the steady-state current for 2 to 5 minutes in the absence of test article (control), the bath solution is switched to one containing the lowest concentration of test article to be used. The peak tail current is monitored until a new steady-state in the presence of test article was achieved. This is followed by the application of the next higher concentration of test article to be tested, and is repeated until all concentrations of test article have been evaluated. Effects of test article on hERG channel are calculated by measuring inhibition of peak tail currents. Percent inhibition of tail currents is plotted as a function of test article concentration to quantify hERG channel inhibition. Test article effects are calculated using tail currents because there are no endogenous tail currents in plasmid-transfected control HEK293 cells.

The sodium current bath solution contains (in mM): 70 NaCl, 70 NMDG, 4 KCl, 1.8 $CaCl_2$, 1 $MgCl_2$, 10 glucose, 10 HEPES (pH 7.4, NaOH). The patch pipette filling solution used in sodium experiments contains (in mM): 130 KCl, 1 $MgCl_2$, 1 $CaCl_2$, 5 ATP-$K_2$, 10 EGTA, 10 HEPES (pH 7.2, KOH).

For determining steady state inhibition, sodium currents are elicited every 5 seconds (0.2 Hz) using the following voltage protocol. Cells are held at a potential of −90 mV and stepped to −20 mV for 45 ms. The peak sodium current in response to the depolarizing step to −20 mV is monitored in the control buffer and after application of test article until a new steady state in the presence of the test article is achieved. To assess the rate dependent inhibition of the sodium currents, trains of voltage steps at frequencies of 1 and 4 Hz (30 sweeps each) are applied to the cell prior to application of test article (control) and after steady state inhibition by test article, as determined at 0.2 Hz frequency. The voltage waveform used in the rate dependence experiments is the same as the waveform used for evaluating steady state inhibition at 0.2 Hz stimulation frequency. Rate dependent inhibition is calculated by comparing the 30th voltage sweep in presence of test article to the 30th voltage sweep under control conditions at each frequency tested.

The L-type calcium current bath solution contains (in mM): 103 NaCl, 30 BaCl$_2$, 4 CsCl, 1 MgCl$_2$, 10 glucose, 10 HEPES (pH 7.35, NaOH). Borosilicate glass pipettes had tip resistances of 2-4 MΩ when filled with an internal solution containing (in mM): 20 CsCl, 20 TEA chloride, 82 glutamate, 3 ATP-Mg, 0.5 NaH$_2$PO$_4$, 3 Na$_2$-creatine PO$_4$, 11 EGTA, 10 HEPES (pH 7.25, CsOH). The bath and the pipette solution in the L-type calcium channel assay minimize current rundown over time.

L-type calcium currents are elicited by 200 ms step depolarizations applied from a holding potential of −50 mV to a test potential of +30 mV. The voltage steps are applied in 5 second intervals (0.2 Hz) and the peak inward current is recorded. After recording the steady state current for 2-5 minutes in the absence of test article, the bath solution is switched to one containing the lowest concentration of the test article to be tested. The peak inward current is monitored until a new steady-state in the presence of test article is achieved.

Compounds are tested in 3 cells at each concentration in each ion channel assay. Currents are sampled at rates at least 2 times the low pass filter rate. The flow rate is kept constant throughout the experiments. All currents were recorded at room temperature ~25° C. IC50 values are calculated using the sigmoidal concentration-response equation $Y=A+((B-A)/(1+((C/X)^D)))$ in XLfit where A and B are the minimum and maximum % inhibition, C is the IC50 and D is the slope factor.

Find below in Table 11 data for compared compounds (See WO 2011/127106 A1). Generally, the comparative data shows the unexpected improvement in cardiac channel liability of the compounds of the present invention.

TABLE 11

Comparative Electrophysiology Data

| Compound | hERG % Inhibition | Na % Inhibition | Ca % Inhibition |
|---|---|---|---|
| Example 5 WO 2011/127106 A1 | 67% @ 3 µM | 51% @ 10 µM @ 1 Hz; 56% @ 10 µM @ 4 Hz | 57% @ 10 µM |
| Example 3 Present Invention | 33% @ 30 µM | 14% @ 10 µM @ 1 Hz; 23% @ 10 µM @ 4 Hz | 9% @ 10 µM |
| Example 4 Present Invention | 40% @ 30 µM | 6% @ 10 µM @ 1 Hz; 7% @ 10 µM @ 4 Hz | 7% @ 10 µM |

Surprisingly, it was discovered that the compounds of the present invention possess beneficial pharmacological characteristics, such as, the combination of potent GPR119 efficacy, improved bioavailability, improved solubility, and a decrease in the potential for adverse side-effects, for example, cardiac channel liability and in vivo glucose reduction compounds in comparison to compounds know in the art. See Tables 5, 6, 7, 8, 9 and 10. For example, see Example 4 of the present invention and Example 5 of WO 2011/127106 A1. For example, Example 4 of the present invention has an aqueous solubility of 2 µg/mL, a FaSSIF solubility of 11 µg/mL, a rat bioavailability of 122% at 2 mg/kg as a microsuspension, and a sodium channel percent inhibition of 6% @ 10 µM @ 1 Hz and 7% @ 10 µM @ 4 Hz. In comparison, Example 5 of Example 5 of WO 2011/127106 A1 is about five times less aqueous soluble (<0.4 µg/mL), about four times less FaSSIF soluble (0.3 µg/mL), about four times less bioavailable (33% at 5 mg/kg as a nanosuspension), and about five times more likely to inhibit sodium channel activity (percent inhibition of 51% @ 10 µM @ 1 Hz and 56% @ 10 µM @ 4 Hz).

Utilities and Combinations

A. Utilities

The compounds of the present invention possess activity as agonists of the GPR119 receptor, and, therefore, may be used in the treatment of diseases associated with GPR119 receptor activity. Via the activation of GPR119 receptor, the compounds of the present invention may preferably be employed to increase insulin production, increase GLP-1 secretion, increase GIP secretion or a combination thereof.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, insulin resistance, hyperinsulinemia, retinopathy, neuropathy, nephropathy, wound healing, atherosclerosis and its sequelae (acute coronary syndrome, myocardial infarction, angina pectoris, peripheral vascular disease, intermittent claudication, myocardial ischemia, stroke, heart failure), Metabolic Syndrome, hypertension, obesity, dyslipidemia, hyperlipidemia, hypertriglyceridemia, hypercholesterolemia, low HDL, high LDL, vascular restenosis, peripheral arterial disease, lipid disorders, bone disease (including osteoporosis), PCOS, HIV protease associated lipodystrophy, and glaucoma, and treatment of side-effects related to diabetes, lipodystrophy and osteoporosis from corticosteroid treatment.

Metabolic Syndrome or "Syndrome X" is described in Ford et al., *J. Am. Med. Assoc.*, 287:356-359 (2002) and Arbeeny et al., *Curr. Med. Chem.—Imm., Endoc. & Metab. Agents*, 1:1-24 (2001).

B. Combinations

The present invention includes within its scope pharmaceutical compositions comprising, as an active ingredient, a therapeutically effective amount of at least one of the compounds of Formula I, Formula Ia, preferably, a compound selected from one of the examples, more preferably Examples 1-4, even more preferably, Examples 1 and 4, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, appetite suppressants, treatments for heart failure, treatments for peripheral arterial disease and anti-inflammatory agents.

Examples of suitable anti-diabetic agents for use in combination with the compounds of the present invention include insulin and insulin analogs (e.g., LysPro insulin, inhaled formulations comprising insulin); glucagon-like peptides; sulfonylureas and analogs (e.g., chlorpropamide, glibenclamide, tolbutamide, tolazamide, acetohexamide, glypizide, glyburide, glimepiride, repaglinide, meglitinide); biguanides (e.g., metformin, phenformin, buformin); alpha2-antagonists and imidazolines (e.g., midaglizole, isaglidole, deriglidole, idazoxan, efaroxan, fluparoxan); other insulin secretagogues (e.g., linogliride, insulinotropin, exendin-4, N,N-dimethyl-N'-[2-(4-morpholinyl)phenyl]guanidine (E)-2-butenedioate salt (BTS-675820), (−)-N-(trans-4-isopropylcyclohexanecarbonyl)-D-phenylalanine (A-4166)); thiazolidinediones and PPAR-gamma agonists (e.g., ciglitazone, pioglitazone, troglitazone, rosiglitazone); PPAR-alpha agonists e.g., fenofibrate, gemfibrozil); PPAR alpha/gamma dual agonists (e.g., muraglitazar, peliglitazar, aleglitazar); SGLT2 inhibitors (e.g., 3-(benzo[b]furan-5-yl)-2',6'-dihydroxy-4'-methyl-propiophenone-2'-O-(6-O-methoxycarbonyl)-β-d-glucopyranoside (T-1095 Tanabe Seiyaku), phlorizin, TS-033 (Taisho), dapagliflozin (BMS), sergiflozin (Kissei), AVE 2268 (Sanofi-Aventis)), canagliflozin; 11-beta-hydroxysteriod dehydrogenase type I inhibitors (e.g., AMG221, INCB13739); dipeptidyl peptidase-IV (DPP4) inhibitors (e.g., saxagliptin, sitagliptin, vildagliptin, alogliptin, linagliptin, dutogliptin and denagliptin); glucagon-like peptide-1 (GLP-1) receptor agonists (e.g., Exenatide (Byetta), NN2211 (Liraglutide, Novo Nordisk), AVE0010 (Sanofi-Aventis), R1583 (Roche/Ipsen), SUN E7001 (Daiichi/Santory), GSK-716155 (GSK/Human Genome Sciences) and Exendin-4 (PC-DAC™); aldose reductase inhibitors (e.g., those disclosed in WO 99/26659); R×R agonists (e.g., reglitazar (JTT-501), 5-[[6-[(2-fluorophenyl)methoxy]-2-naphthalenyl]methyl]-2,4-thiazolidinedione (MCC-555), 5-[[3-(5,6,7,8-tetrahydro-3,5,5,8,8-pentamethyl-2-naphthalenyl)-4-(trifluoromethoxy)-phenyl]methylene]-2,4-thiazolidinedione (MX-6054), DRF2593, farglitazar, (±)-5-[(2,4-dioxothiazolidin-5-yl)methyl]-2-methoxy-N-[[(4-trifluoromethyl)phenyl]-methyl]benzamide (KRP-297), 6-[1-(5,6,7,8-tetrahydro-3,5,5,8,8-pentamethyl-2-naphthalenyl)cyclopropyl]-3-pyridinecarboxylic acid (LG100268)); fatty acid oxidation inhibitors (e.g., clomoxir, etomoxir; α-glucosidase inhibitors: precose, acarbose, miglitol, emiglitate, voglibose, 2,6-dideoxy-2,6-imino-7-O-β-D-glucopyranosyl-D-glycero-L-gulo-heptitol (MDL-25,637), camiglibose); beta-agonists (e.g., methyl ester [4-[(2R)-2-[[(2R)-2-(3-chlorophenyl)-2-hydroxyethyl]amino]propyl]phenoxy]-acetic acid (BRL 35135), 2-[4-[(2S)-2-[[(2S)-2-(3-chlorophenyl)-2-hydroxyethyl]amino]propyl]phenoxy]-acetic acid (BRL 37344), 4-[(3R)-3-[bis[(2R)-2-hydroxy-2-phenylethyl]amino]butyl]-benzamide (Ro 16-8714), 2-[4-[2-[[(2S)-2-hydroxy-3-phenoxypropyl]amino]ethoxy] phenoxy]-N-(2-methoxyethyl)-acetamide (ICI D7114), 5-[(2R)-2-[[(2R)-2-(3-chlorophenyl)-2-hydroxyethyl] amino]propyl]-3-benzodioxole-2,2-dicarboxylic acid, disodium salt (CL 316,243), TAK-667, AZ40140); phosphodiesterase inhibitors, both cAMP and cGMP type (e.g., sildenafil, 9-((1S,2R)-2-fluoro-1-methylpropyl)-2-methoxy-6-(1-piperazinyl)purine hydrochloride (L-686398), L-386,398); amylin agonists (e.g., pramlintide); lipoxygenase inhibitors (e.g., masoprocal); somatostatin analogs (e.g., lanreotide, seglitide, octreotide); glucagon antagonists (e.g., BAY 276-9955); insulin signaling agonists, insulin mimetics, PTP1B inhibitors (e.g., 2-[2-(1,1-dimethyl-2-propenyl)-1H-indol-3-yl]-3,6-dihydroxy-5-[7-(3-methyl-2-butenyl)-1H-indol-3-yl]-2,5-cyclohexadiene-1,4-dione (L-783281), TER17411, TER17529); gluconeogenesis inhibitors (e.g., GP3034); somatostatin analogs and antagonists; antilipolytic agents (e.g., nicotinic acid, acipimox, N-cyclohexyl-2'-O-methyl-adenosine (WAG 994)); glucose transport stimulating agents (e.g., 4-chloro-α-[(4-methylphenyl)sulfonyl]-benzeneheptanoic acid (BM-130795)); glucose synthase kinase inhibitors (e.g., lithium chloride, CT98014, CT98023); galanin receptor agonists; Chemokine receptor antagonist CCR2/5 (e.g., NCB3284, MK-0812, INCB8696, maraviroc (Pfizer) and vicriviroc); thyroid receptor agonists (e.g., KB-2115 (KaroBio)); glucokinase activators (e.g., RO-27-4375, RO-28-1675 (Roche), 6-[[3-[(1S)-2-methoxy-1-methylethoxy]-5-[(1S)-1-methyl-2-phenylethoxy]benzoyl] amino]-3-pyridinecarboxylic acid (GKA-50 AstraZeneca)); GPR40 modulators (e.g., (S)-4-(dimethylamino)-3-(4-((4-methyl-2-p-tolylthiazol-5-yl)methoxy)phenyl)-4-oxobutanoic acid, 6-chloro-2-(4-chlorobenzylthio)-1-(4-(methoxymethoxy)phenyl)-1H-benzo[d]imidazole, TAK-875, CNX011, and P1736).

Examples of suitable lipid lowering agents and anti-atherosclerotic agents for use in combination with the compounds of the present invention include one or more MTP/ApoB secretion inhibitors (e.g., dirlopatide, N-(2,2,2-trifluoroethyl)-9-[4-[4-[[[4'-(trifluoromethyl)[1,1'-biphenyl]-2-yl]carbonyl]-amino]-1-piperidinyl]butyl]-9H-fluorene-9-carboxamide, methanesulfonate, CP-741952 (Pfizer), SLx-4090 (Surface Logix)); HMG CoA reductase inhibitors (e.g., atorvastatin, rosuvastatin, simvastatin, pravastatin, lovastatin, fluvastatin); squalene synthetase inhibitors, PPAR alpha agonists and fibric acid derivatives (e.g., fenofibrate, gemfibrozil); ACAT inhibitors; lipoxygenase inhibitors; cholesterol absorption inhibitors (e.g., ezetimibe); thyroid receptor agonists (e.g., as set forth above); Ileal Na+/bile acid cotransporter inhibitors (e.g., compounds as disclosed in Drugs of the Future, 24:425-430 (1999); upregulators of LDL receptor activity (e.g., (3R)-3-[(13R)-13-hydroxy-10-oxotetradecyl]-5,7-dimethoxy-1(3H)-isobenzofuranone (Taisho Pharmaceutical Co. Ltd.) and (3α, 4α,5α)-4-(2-propenyl)-cholestan-3-ol (Eli Lilly); bile acid sequestrants (e.g., WELCHOL®, COLESTID®, LoCholest and QUESTRAN®; and fibric acid derivatives, such as Atromid, LOPID® and Tricot); cholesterol ester transfer protein inhibitors (e.g., torcetrapib and (2R)-3-{[3-(4-chloro-3-ethyl-phenoxy)-phenyl]-[[3-(1,1,2,2-tetrafluoroethoxy)phenyl]methyl]amino}-1,1,1-trifluoro-2-propanol); nicotinic acid and derivatives thereof (e.g., niacin, acipimox); PCSK9 inhibitors; LxR agonists (e.g., those disclosed in U.S. Patent Application Publication Nos. 2003/01814206, 2005/

0080111, and 2005/0245515); lipoxygenase inhibitors (e.g., such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al., "Attenuation of diet-induced atherosclerosis in rabbits with a highly selective 15-lipoxygenase inhibitor lacking significant antioxidant properties", *Brit. J. Pharmacology*, 120:1199-1206 (1997), and Cornicelli et al., "15-Lipoxygenase and its Inhibition: A Novel Therapeutic Target for Vascular Disease", *Current Pharmaceutical Design*, 5:11-20 (1999)).

Preferred hypolipidemic agents are pravastatin, lovastatin, simvastatin, atorvastatin, fluvastatin, cerivastatin, atavastatin, and rosuvastatin.

Examples of suitable anti-hypertensive agents for use in combination with the compounds of the present invention include beta adrenergic blockers, calcium channel blockers (L-type and T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors (e.g., aliskiren), ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan, and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopeptidase inhibitors (dual NEP-ACE inhibitors) (e.g., omapatrilat and gemopatrilat), nitrates, central alpha agonists (e.g., clonidine), alpha1 blockers (e.g., prazosine), arterial vasodilators (e.g., minoxidil), sympatolytics (e.g., resperine), renin inhibitors (e.g., Aliskiren (Novartis)).

Examples of suitable anti-obesity agents for use in combination with the compounds of the present invention include a cannabinoid receptor 1 antagonist or inverse agonist (e.g., rimonabant, (4S)-3-(4-chlorophenyl)-N-[(4-chlorophenyl) sulfonyl]-4,5-dihydro-N'-methyl-4-phenyl-1H-pyrazole-1-carboximidamide (SLV 319), CP-945598 (Pfizer), Surinabant (SR-147778, Sanofi-Aventis), N-[(1S,2S)-3-(4-chlorophenyl)-2-(3-cyanophenyl)-1-methylpropyl]-2-methyl-2-{[5-(trifluoromethyl)pyridin-2-yl] oxy}propanamide (Merck) and those discussed in Hertzog, D. L., *Expert Opin. Ther. Patents*, 14:1435-1452 (2004)); a beta 3 adrenergic agonist (e.g., rafabegron (AJ9677, Takeda/Dainippon), N-[4-[2-[[(2S)-3-[(6-amino-3-pyridinyl)oxy]-2-hydroxypropyl]amino]ethyl]phenyl]-4-(1-methylethyl)-benzenesulfonamide (L750355, Merck), or CP331648 (Pfizer), or other known beta 3 agonists, as disclosed in U.S. Pat. Nos. 5,541,204, 5,770,615, 5,491,134, 5,776,983, and 5,488,064, with rafabegron, N-[4-[2-[[(2S)-3-[(6-amino-3-pyridinyl)oxy]-2-hydroxypropyl]amino]ethyl]phenyl]-4-(1-methylethyl)-benzenesulfonamide, and CP331648 being preferred); a lipase inhibitor (e.g., orlistat or cetilistat, with orlistat being preferred); a serotonin and norepinephrine reuptake inhibitor (e.g., sibutramine, Abbott and tesofensine, Neurosearch) with sibutramine being preferred; a dopamine reuptake inhibitor (e.g., buprorion, GSK); or 5-HT$_{2C}$ agonist, (e.g., lorcaserin hydrochloride (Arena), WAY-163909 [(7bR,10aR)-1,2,3,4,8,9,10,10a-octahydro-7bH-cyclopenta-[b][1,4]diazepino[6,7,1hi]indole], with lorcaserin hydrochloride being preferred); 5-HT6 receptor antagonists (Suven, Biovitrum, Epix), anti-epileptics topiramate (Johnson & Johnson) and zonisamide, a ciliary neurotrophic factor agonist (e.g., AXOKINE® (Regeneron); brain-derived neurotrophic factor (BDNF), orexin antagonists, histamine receptor-3 (H3) modulators, melanin-concentrating hormone receptor (MCHR) antagonists (e.g., GSK-856464 (GlaxoSmithKline), T-0910792 (Amgen)); diacylglycerol acyltransferase (DGAT) inhibitors (e.g., BAY-74-4113 (Bayer), PF-04620110, and LCQ908); acetyl-CoA carboxylase (ACC) inhibitors (e.g., N-(4-(4-(4-isopropoxyphenoxy)phenyl)but-3-yn-2-yl)acetamide (A-80040, Abbott), (R)-anthracen-9-yl(3-(morpholine-4-carbonyl)-1,4'-bipiperidin-1'-yl) methanone (CP-640186, Pfizer)), SCD-1 inhibitors as described by Jiang et al., *Diabetes*, 53 (2004), (abs 653-p); amylin receptor agonists (e.g., compounds disclosed in WO 2005/025504); thyroid receptor agonists (e.g., as set forth above); growth hormone secretagogue receptor (GHSR) antagonists (e.g., A-778193 (Abbott), leptin and leptin mimetics (e.g., OB-3 (Aegis/Albany Medical College), leptin analogs A-100 and A-200 (Amgen), CBT-001452 (Cambridge Biotechnology), ML-22952 (Millennium)), PYY receptor agonist (e.g., AC-162352 (Amylin), PYY-3-36 (Emishere), PYY(3-36)NH2 (Unigene)), NPY-Y4 agonists (7™ Pharma WO 2005/089786(A2,A3)-1), NPY-5 antagonists (e.g., NPY5RA-972 (AstraZeneca), GW-594884A (GlaxoSmithKline), J-104870 (Banyu)); MTP/apoB secretion inhibitors (as set forth above), and/or an anorectic agent.

The anorectic agent which may be optionally employed in combination with compounds of the present invention include dexamphetamine, phentermine, phenylpropanolamine, or mazindol, with dexamphetamine being preferred.

Other compounds that can be used in combination with the compounds of the present invention include CCK receptor agonists (e.g., SR-27895B); galanin receptor antagonists; MCR-4 antagonists (e.g., N-acetyl-L-norleucyl-L-glutaminyl-L-histidyl-D-phenylalanyl-L-arginyl-D-tryptophyl-glycinamide, (HP-228); urocortin mimetics, CRF antagonists, and CRF binding proteins (e.g., mifepristone (RU-486), urocortin).

Further, the compounds of the present invention may be used in combination with HIV protease inhibitors, including but not limited to REYATAZ® and KALETRA®.

Examples of suitable memory enhancing agents, anti-dementia agents, or cognition promoting agents for use in combination with the compounds of the present invention include, but are not limited to ARICEPT®, razadyne, donepezil, rivastigmine, galantamine, memantine, tacrine, metrifonate, muscarine, xanomelline, deprenyl and physostigmine.

Examples of suitable anti-inflammatory agents for use in combination with the compounds of the present invention include, but are not limited to, NSAIDS, prednisone, acetaminophen, aspirin, codeine, fentanyl, ibuprofen, indomethacin, ketorolac, morphine, naproxen, phenacetin, piroxicam, sufentanyl, sunlindac, interferon alpha, prednisolone, methylprednisolone, dexamethazone, flucatisone, betamethasone, hydrocortisone, beclomethasone, REMICADE®, ORENCIA®, and ENBREL®.

The aforementioned patents and patent applications are incorporated herein by reference.

The above other therapeutic agents, when employed in combination with the compounds of the present invention may be used, for example, in those amounts indicated in the Physicians' Desk Reference, as in the patents set out above, or as otherwise determined by one of ordinary skill in the art.

Dosage and Formulation

The compounds of this disclosure can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, when used for the indicated effects, will range between about 0.001 to 1000 mg/kg of body weight, or between about 0.01 to 100 mg/kg of body weight per day, or alternatively, between about 1.0 to 20 mg/kg/day. Compounds of this invention may be administered in a single daily dose, or the total daily dosage may be administered in divided doses of two, three, or four times daily. In one embodiment, the daily oral dosage of the active ingredient is between 3 and 600 mg either administered once daily or in divided doses administered twice daily. Alternatively, the active ingredient may be administered in doses of 10-20 mg administered twice daily or 40 to 100 mg administered once daily. Alternatively, the active ingredient may be administered a dose of 12.5 mg twice a day or 75 mg once a day. Alternatively, the active ingredient may be administered in doses of 3, 10, 30, 100, 300, and 600 mg administered either once or twice a day.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Dispersion

A spray dried dispersion can be prepared for oral administration by methods know to one skilled in the art.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where two or more of the foregoing second therapeutic agents are administered with the compound of the examples, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the examples and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Additionally, certain compounds disclosed herein may be useful as metabolites of other compounds. Therefore, in one embodiment, compounds may be useful either as a substantially pure compound, which may also then be incorporated into a pharmaceutical composition, or may be useful as metabolite which is generated after administration of the prodrug of that compound. In one embodiment, a compound may be useful as a metabolite by being useful for treating disorders as described herein.

What is claimed is:

1. A compound of formula I

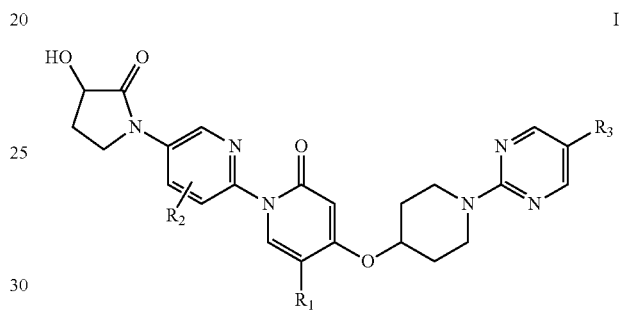

enantiomer, diastereomer, tautomer, or salt thereof wherein:

$R_1$ is hydrogen or halo;
$R_2$ is $(C_1-C_{10})$alkyl; and
$R_3$ is halo or $(C_1-C_{10})$alkyl.

2. The compound, enantiomer, diastereomer, tautomer, or salt thereof, of claim 1, wherein the compound is a compound of formula Ia

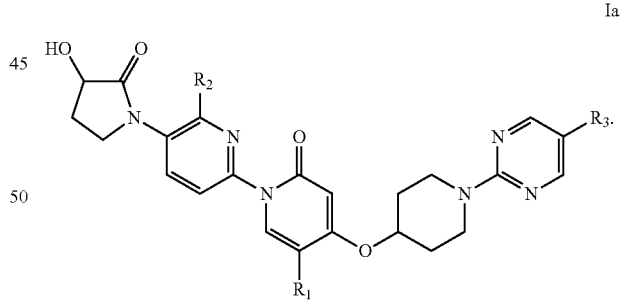

3. The compound, enantiomer, diastereomer, tautomer, or salt thereof, of claim 1, wherein:

$R_1$ is hydrogen or halo;
$R_2$ is $(C_1-C_5)$alkyl; and
$R_3$ is halo or $(C_1-C_7)$alkyl.

4. The compound, enantiomer, diastereomer, tautomer, or salt thereof, of claim 1, wherein;

$R_1$ is hydrogen or Cl;
$R_2$ is methyl or ethyl; and
$R_3$ is halo or $(C_1-C_5)$alkyl.

5. The compound, enantiomer, diastereomer, tautomer, or salt thereof, of claim 2, wherein:

R₁ is hydrogen or halo;
R₂ is (C₁-C₅)alkyl; and
R₃ is halo or (C₁-C₃)alkyl.

6. The compound, enantiomer, diastereomer, tautomer, or salt thereof, of claim 1, wherein the compound is selected from one of the following compounds:

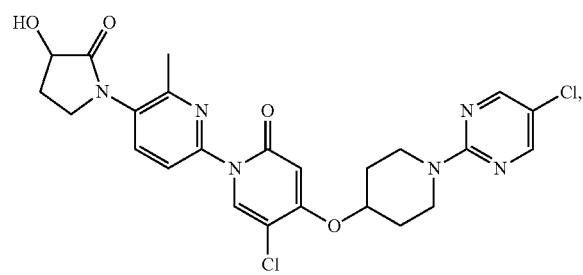

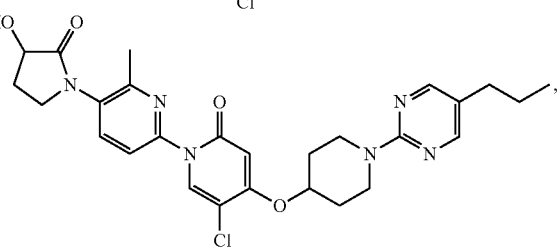

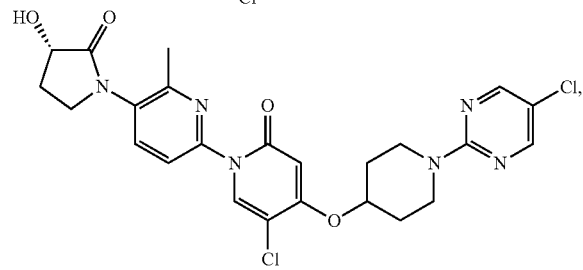

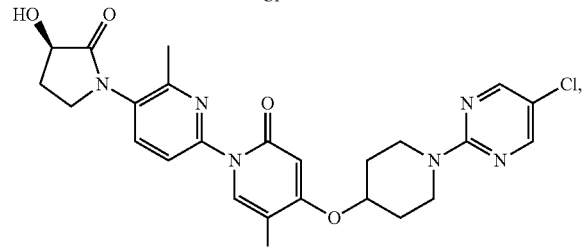

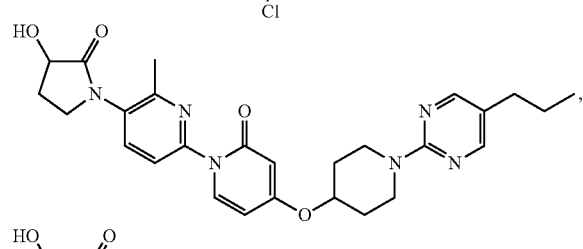

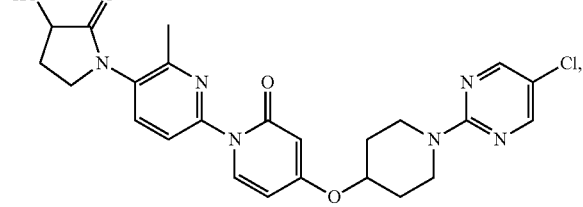

and (R)-5-chloro-4-((1-(5-chloropyrimidin-2-yl)piperidin-4-yl)oxy)-5'-(3-hydroxy-2-oxopyrrolidin-1-yl)-6'-methyl-2H-[1,2'-bipyridin]-2-one.

7. The compound, enantiomer, tautomer, or salt thereof, of claim 1, wherein the compound has the formula:

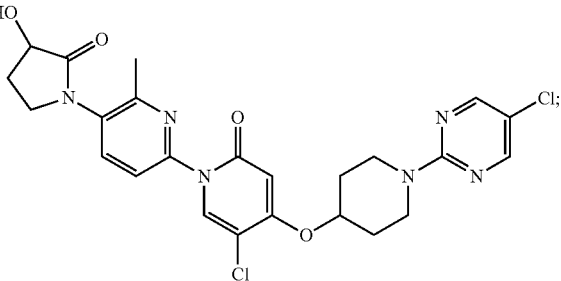

8. A compound or salt thereof, having the formula:

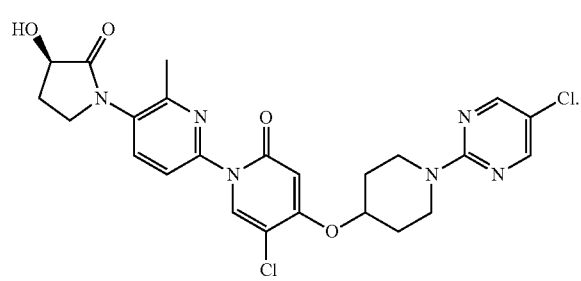 [SMILES: Cc1nc(-n2cc(Cl)c(OC3CCN(c4ncc(Cl)cn4)CC3)cc2=O)ccc1N1CC[C@@H](O)C1=O]

9. A compound or salt thereof, having the formula:

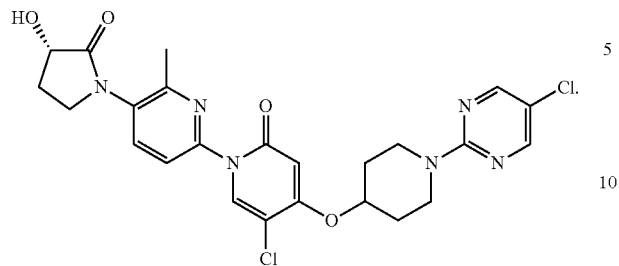

10. A pharmaceutical composition comprised of a therapeutically effective amount of a compound of claim 1, or an enantiomer, a diastereomer, or a pharmaceutically acceptable salt thereof, and optionally a pharmaceutically acceptable carrier.

11. The pharmaceutical composition of claim 10, further comprising a therapeutically effective amount of one or more other therapeutically active agents.

12. A pharmaceutical composition comprising a therapeutically effective amount of the compound of claim 1 and a therapeutically effective amount of a dipeptidyl peptidase-IV (DPP4) inhibitor.

13. The pharmaceutical composition of claim 12, wherein the dipeptidyl peptidase-IV (DPP4) inhibitor is saxagliptin.

* * * * *